(12) United States Patent
Ismagilov et al.

(10) Patent No.: US 9,464,319 B2
(45) Date of Patent: Oct. 11, 2016

(54) MULTIVOLUME DEVICES, KITS AND RELATED METHODS FOR QUANTIFICATION OF NUCLEIC ACIDS AND OTHER ANALYTES

(75) Inventors: Rustem F. Ismagilov, Chicago, IL (US); Feng Shen, Chicago, IL (US); Jason E. Kreutz, Chicago, IL (US); Wenbin Du, Chicago, IL (US); Bing Sun, Chicago, IL (US)

(73) Assignees: CALIFORNIA INSTITUTE OF TECHNOLOGY, Pasadena, CA (US); UNIVERSITY OF CHICAGO, Chicago, IL (US)

( * ) Notice: Subject to any disclaimer, the term of this patent is extended or adjusted under 35 U.S.C. 154(b) by 0 days.

(21) Appl. No.: 13/467,482

(22) Filed: May 9, 2012

(65) Prior Publication Data

US 2012/0329038 A1    Dec. 27, 2012

Related U.S. Application Data

(63) Continuation-in-part of application No. 13/440,371, filed on Apr. 5, 2012, and a continuation-in-part of application No. 13/257,811, filed as application No. PCT/US2010/028316 on Mar. 23, 2010.

(Continued)

(51) Int. Cl.
| | |
|---|---|
| *C12Q 1/68* | (2006.01) |
| *B01F 13/00* | (2006.01) |
| *B01L 3/00* | (2006.01) |

(52) U.S. Cl.
CPC ....... *C12Q 1/6851* (2013.01); *B01L 3/502738* (2013.01); *B01F 13/0094* (2013.01); *B01L 3/5025* (2013.01); *B01L 3/50851* (2013.01); *B01L 2200/027* (2013.01); *B01L 2200/0605* (2013.01); *B01L 2200/0642* (2013.01); *B01L 2300/045* (2013.01); *B01L 2300/049* (2013.01);

(Continued)

(58) Field of Classification Search
CPC .................. B01L 2200/027; B01L 3/502738; B01L 2300/0864; B01L 3/5025; B01F 13/00; B01F 13/0094
See application file for complete search history.

(56) References Cited

U.S. PATENT DOCUMENTS

| | | |
|---|---|---|
| 2,541,413 A | 2/1951 | Gorey |
| 3,787,290 A | 1/1974 | Kaye |

(Continued)

FOREIGN PATENT DOCUMENTS

| | | |
|---|---|---|
| CN | 2482070 Y | 3/2002 |
| CN | 1886644 A | 12/2006 |

(Continued)

OTHER PUBLICATIONS

Beer et al., "On-Chip Single-Copy Real-Time Reverse-Transcription PCR in Isolated Picoliter Droplets", Anal. Chem., 2008, 80, 1854-1858.

(Continued)

*Primary Examiner* — Jonathan Hurst
(74) *Attorney, Agent, or Firm* — Fenwick & West LLP

(57) ABSTRACT

Provided are devices comprising multivolume analysis regions, the devices being capable of supporting amplification, detection, and other processes. Also provided are related methods of detecting or estimating the presence nucleic acids, viral levels, and other biological markers of interest.

24 Claims, 17 Drawing Sheets

Related U.S. Application Data

(60) Provisional application No. 61/262,375, filed on Nov. 18, 2009, provisional application No. 61/162,922, filed on Mar. 24, 2009, provisional application No. 61/340,872, filed on Mar. 22, 2010, provisional application No. 61/518,601, filed on May 9, 2011, provisional application No. 61/516,628, filed on Apr. 5, 2011.

(52) U.S. Cl.
CPC . *B01L 2300/0803* (2013.01); *B01L 2300/0816* (2013.01); *B01L 2300/0864* (2013.01); *B01L 2400/0406* (2013.01); *B01L 2400/065* (2013.01); *B01L 2400/0644* (2013.01)

(56) References Cited

U.S. PATENT DOCUMENTS

| | | |
|---|---|---|
| 3,996,345 A | 12/1976 | Ullman et al. |
| 4,071,409 A | 1/1978 | Messing et al. |
| 4,755,363 A | 7/1988 | Fujita et al. |
| 4,853,336 A | 8/1989 | Saros et al. |
| 4,963,498 A | 10/1990 | Hillman et al. |
| 5,026,113 A | 6/1991 | DiCarlo et al. |
| 5,114,208 A | 5/1992 | Ikeda et al. |
| 5,169,942 A | 12/1992 | Johnson et al. |
| 5,185,099 A | 2/1993 | Delpuech et al. |
| 5,251,670 A | 10/1993 | Bates et al. |
| 5,264,570 A | 11/1993 | Johnson et al. |
| 5,478,893 A | 12/1995 | Ghosh et al. |
| 5,518,892 A * | 5/1996 | Naqui et al. ............ 435/29 |
| 5,656,493 A | 8/1997 | Mullis et al. |
| 5,686,315 A | 11/1997 | Pronovost et al. |
| 5,688,651 A | 11/1997 | Solomon |
| 5,707,850 A | 1/1998 | Cole |
| 5,725,017 A | 3/1998 | Elsberry et al. |
| 5,726,026 A | 3/1998 | Wilding et al. |
| 5,739,036 A | 4/1998 | Parris |
| 5,744,305 A | 4/1998 | Fodor et al. |
| 5,746,978 A | 5/1998 | Bienhaus et al. |
| 5,772,889 A | 6/1998 | Gjerde et al. |
| 5,773,258 A | 6/1998 | Birch et al. |
| 5,805,947 A | 9/1998 | Miyamoto et al. |
| 5,872,010 A | 2/1999 | Karger et al. |
| 5,948,624 A | 9/1999 | Rothschild et al. |
| 5,993,631 A | 11/1999 | Parton et al. |
| 5,997,636 A | 12/1999 | Gamarnik et al. |
| 6,013,166 A | 1/2000 | Heller |
| 6,130,098 A | 10/2000 | Handique et al. |
| 6,140,053 A | 10/2000 | Koster |
| 6,146,854 A | 11/2000 | Koster et al. |
| 6,168,948 B1 | 1/2001 | Anderson et al. |
| 6,171,785 B1 | 1/2001 | Higuchi |
| 6,180,372 B1 | 1/2001 | Franzen |
| 6,197,595 B1 | 3/2001 | Anderson et al. |
| 6,203,989 B1 | 3/2001 | Goldberg et al. |
| 6,274,726 B1 | 8/2001 | Laugharn, Jr. et al. |
| 6,277,648 B1 | 8/2001 | Colpan |
| 6,300,138 B1 | 10/2001 | Gleason et al. |
| 6,379,929 B1 | 4/2002 | Burns et al. |
| 6,391,624 B1 | 5/2002 | Megerle |
| 6,409,832 B2 | 6/2002 | Weigl et al. |
| 6,426,230 B1 | 7/2002 | Feistel |
| 6,436,292 B1 | 8/2002 | Petro |
| 6,451,610 B1 | 9/2002 | Gorman et al. |
| 6,465,640 B1 | 10/2002 | Hood |
| 6,500,617 B1 | 12/2002 | Stemmer et al. |
| 6,503,707 B1 | 1/2003 | Baxter-Lowe |
| 6,524,456 B1 | 2/2003 | Ramsey et al. |
| 6,548,256 B2 | 4/2003 | Lienau et al. |
| 6,550,497 B2 | 4/2003 | Thiele et al. |
| 6,565,813 B1 | 5/2003 | Garyantes |
| 6,567,492 B2 | 5/2003 | Kiselev et al. |
| 6,569,631 B1 | 5/2003 | Pantoliano et al. |
| 6,575,188 B2 | 6/2003 | Parunak |
| 6,606,618 B2 | 8/2003 | Delo |
| 6,632,653 B1 | 10/2003 | Astle |
| 6,638,408 B1 | 10/2003 | Speicher et al. |
| 6,702,256 B2 | 3/2004 | Killeen et al. |
| 6,705,357 B2 | 3/2004 | Jeon et al. |
| 6,716,642 B1 | 4/2004 | Wu et al. |
| 6,717,136 B2 | 4/2004 | Andersson et al. |
| 6,720,187 B2 | 4/2004 | Bedingham et al. |
| 6,737,026 B1 * | 5/2004 | Bergh ............ B01F 15/0264 422/129 |
| 6,797,056 B2 | 9/2004 | David |
| 6,808,934 B2 | 10/2004 | Mutz et al. |
| 6,821,770 B1 | 11/2004 | Hogan |
| 6,845,968 B2 | 1/2005 | Killeen et al. |
| 6,852,851 B1 | 2/2005 | Tooke et al. |
| 6,855,490 B2 | 2/2005 | Sompuram et al. |
| 6,858,439 B1 | 2/2005 | Xu et al. |
| 6,883,559 B2 | 4/2005 | Jeon et al. |
| 6,893,612 B2 | 5/2005 | Kacian et al. |
| 6,949,355 B2 | 9/2005 | Yamanishi et al. |
| 6,949,575 B2 | 9/2005 | Barta et al. |
| 6,994,749 B2 | 2/2006 | David |
| 7,003,104 B2 | 2/2006 | Lee |
| 7,015,041 B2 | 3/2006 | Santarsiero et al. |
| 7,101,663 B2 | 9/2006 | Godfrey et al. |
| 7,122,301 B2 | 10/2006 | Shvets et al. |
| 7,122,640 B2 | 10/2006 | Gjerde et al. |
| 7,126,626 B2 * | 10/2006 | Sawahara et al. ......... 348/14.02 |
| 7,129,091 B2 | 10/2006 | Ismagilov et al. |
| 7,135,180 B2 | 11/2006 | Truong-Le |
| 7,136,688 B2 | 11/2006 | Jung et al. |
| 7,169,601 B1 | 1/2007 | Northrup et al. |
| 7,235,216 B2 | 6/2007 | Kiselev et al. |
| 7,244,961 B2 | 7/2007 | Jovanovic et al. |
| 7,252,939 B2 | 8/2007 | Mori et al. |
| 7,294,308 B2 | 11/2007 | Kacian et al. |
| 7,294,466 B2 | 11/2007 | McMillan |
| 7,294,503 B2 | 11/2007 | Quake et al. |
| 7,297,485 B2 | 11/2007 | Bornarth et al. |
| 7,306,672 B2 | 12/2007 | Hansen et al. |
| 7,309,588 B2 | 12/2007 | Burg et al. |
| 7,314,070 B2 | 1/2008 | Jeon et al. |
| 7,319,003 B2 | 1/2008 | Cantor et al. |
| 7,329,485 B2 | 2/2008 | Zlotnick |
| 7,351,303 B2 | 4/2008 | Liu et al. |
| 7,375,190 B2 | 5/2008 | Cheng et al. |
| 7,413,712 B2 | 8/2008 | Liu et al. |
| 7,465,562 B2 | 12/2008 | Wangh et al. |
| 7,501,245 B2 | 3/2009 | Quake et al. |
| 7,556,776 B2 | 7/2009 | Fraden et al. |
| 7,595,871 B2 | 9/2009 | Weber |
| 7,608,399 B2 | 10/2009 | Reed et al. |
| 7,615,274 B2 | 11/2009 | Ehrfeld et al. |
| 7,629,165 B2 | 12/2009 | Wyatt et al. |
| 7,648,835 B2 | 1/2010 | Breidford et al. |
| 7,655,129 B2 | 2/2010 | Blackburn et al. |
| 7,683,035 B1 | 3/2010 | Erbacher et al. |
| 7,767,447 B2 | 8/2010 | Breidenthal et al. |
| 7,780,336 B2 | 8/2010 | Breidenthal et al. |
| 7,790,865 B1 | 9/2010 | Heath et al. |
| 7,846,333 B2 | 12/2010 | Pluester et al. |
| 7,851,207 B1 | 12/2010 | Sagripanti |
| 7,867,757 B2 | 1/2011 | Karlsen et al. |
| 7,871,813 B2 | 1/2011 | Wyatt et al. |
| 7,915,030 B2 | 3/2011 | Inoue et al. |
| 7,939,018 B2 | 5/2011 | Bedingham et al. |
| 7,939,249 B2 | 5/2011 | Parthasarathy et al. |
| 7,955,504 B1 | 6/2011 | Jovanovic et al. |
| 7,998,708 B2 | 8/2011 | Handique et al. |
| 8,043,811 B2 | 10/2011 | Danks et al. |
| 8,052,929 B2 | 11/2011 | Breidenthal et al. |
| 8,057,758 B2 | 11/2011 | Bedingham et al. |
| 8,097,222 B2 | 1/2012 | Scurati |
| 8,137,554 B2 | 3/2012 | Jovanovic et al. |
| 8,187,557 B2 | 5/2012 | Van Atta et al. |
| 8,211,367 B2 | 7/2012 | Wyatt et al. |
| 8,221,705 B2 | 7/2012 | Breidenthal et al. |
| 8,222,023 B2 | 7/2012 | Battrell et al. |
| 8,273,245 B2 | 9/2012 | Jovanovic et al. |

(56) References Cited

U.S. PATENT DOCUMENTS

| | | |
|---|---|---|
| 8,323,900 B2 | 12/2012 | Handique et al. |
| 8,362,219 B2 | 1/2013 | Gjerde et al. |
| 8,415,103 B2 | 4/2013 | Handique |
| 8,449,830 B2 | 5/2013 | Claussen et al. |
| 8,470,586 B2 | 6/2013 | Wu et al. |
| 8,480,976 B2 | 7/2013 | Breidenthal et al. |
| 8,491,178 B2 | 7/2013 | Breidenthal et al. |
| 8,574,833 B2 | 11/2013 | Jenison et al. |
| 8,615,368 B2 | 12/2013 | Light, II et al. |
| 8,637,250 B2 | 1/2014 | Jenison |
| 8,784,745 B2 | 7/2014 | Nelson et al. |
| 8,828,654 B2 | 9/2014 | Nelson et al. |
| 2001/0048900 A1 | 12/2001 | Bardell et al. |
| 2002/0008029 A1 | 1/2002 | Williams et al. |
| 2002/0012971 A1 | 1/2002 | Mehta |
| 2002/0017464 A1 | 2/2002 | Parce et al. |
| 2002/0022261 A1 | 2/2002 | Anderson et al. |
| 2002/0058332 A1 | 5/2002 | Quake et al. |
| 2002/0076825 A1 | 6/2002 | Cheng et al. |
| 2002/0125197 A1* | 9/2002 | Hager et al. ............... 210/739 |
| 2002/0147317 A1* | 10/2002 | Bentsen et al. ............... 536/8 |
| 2002/0155032 A1* | 10/2002 | Liu et al. .................. 422/100 |
| 2002/0172969 A1 | 11/2002 | Burns et al. |
| 2003/0022243 A1 | 1/2003 | Kondejewski et al. |
| 2003/0064414 A1 | 4/2003 | Benecky et al. |
| 2003/0190608 A1 | 10/2003 | Blackburn |
| 2003/0229376 A1 | 12/2003 | Sandhu |
| 2004/0005582 A1 | 1/2004 | Shipwash |
| 2004/0037813 A1 | 2/2004 | Simpson et al. |
| 2004/0072357 A1 | 4/2004 | Stiene et al. |
| 2004/0119070 A1* | 6/2004 | Roach et al. ................ 257/48 |
| 2004/0137458 A1 | 7/2004 | Archambault et al. |
| 2004/0181131 A1 | 9/2004 | Maynard et al. |
| 2004/0224419 A1 | 11/2004 | Zheng et al. |
| 2004/0228212 A1* | 11/2004 | de Goor et al. ............. 366/341 |
| 2004/0258571 A1 | 12/2004 | Lee et al. |
| 2005/0009582 A1 | 1/2005 | Vooi-Kia et al. |
| 2005/0019792 A1 | 1/2005 | McBride et al. |
| 2005/0087122 A1 | 4/2005 | Ismagilov et al. |
| 2005/0172476 A1 | 8/2005 | Stone et al. |
| 2005/0221339 A1 | 10/2005 | Griffiths et al. |
| 2006/0003439 A1 | 1/2006 | Ismagilov et al. |
| 2006/0078888 A1 | 4/2006 | Griffiths et al. |
| 2006/0078893 A1 | 4/2006 | Griffiths et al. |
| 2006/0094119 A1 | 5/2006 | Ismagilov et al. |
| 2006/0163385 A1 | 7/2006 | Link et al. |
| 2006/0188911 A1 | 8/2006 | Otomo et al. |
| 2006/0195047 A1 | 8/2006 | Freeman et al. |
| 2007/0003442 A1 | 1/2007 | Link et al. |
| 2007/0014695 A1 | 1/2007 | Yue et al. |
| 2007/0015545 A1 | 1/2007 | Leifer et al. |
| 2007/0026439 A1 | 2/2007 | Faulstich et al. |
| 2007/0052781 A1 | 3/2007 | Fraden et al. |
| 2007/0077547 A1 | 4/2007 | Shvets et al. |
| 2007/0092914 A1 | 4/2007 | Griffiths et al. |
| 2007/0093894 A1 | 4/2007 | Darouiche |
| 2007/0134739 A1 | 6/2007 | Holmquist et al. |
| 2007/0172954 A1 | 7/2007 | Ismagilov et al. |
| 2007/0184489 A1 | 8/2007 | Griffiths et al. |
| 2007/0195127 A1 | 8/2007 | Ahn et al. |
| 2007/0202525 A1 | 8/2007 | Quake et al. |
| 2008/0003142 A1 | 1/2008 | Link et al. |
| 2008/0003693 A1 | 1/2008 | Torres |
| 2008/0014589 A1 | 1/2008 | Link et al. |
| 2008/0058039 A1 | 3/2008 | Lee et al. |
| 2008/0107565 A1 | 5/2008 | Vivienne et al. |
| 2008/0108063 A1 | 5/2008 | Lucero et al. |
| 2008/0129736 A1 | 6/2008 | Sun et al. |
| 2008/0166793 A1 | 7/2008 | Beer et al. |
| 2008/0213215 A1 | 9/2008 | Krishnan et al. |
| 2008/0293045 A1 | 11/2008 | Piepenburg et al. |
| 2009/0010804 A1 | 1/2009 | Withrow, III et al. |
| 2009/0021728 A1 | 1/2009 | Heinz et al. |
| 2009/0035847 A1 | 2/2009 | Cho et al. |
| 2009/0053719 A1 | 2/2009 | Lo et al. |
| 2009/0057149 A1 | 3/2009 | Wegner et al. |
| 2009/0060797 A1 | 3/2009 | Mathies et al. |
| 2009/0062134 A1 | 3/2009 | Linton et al. |
| 2009/0068760 A1 | 3/2009 | Nelson et al. |
| 2009/0069194 A1 | 3/2009 | Ramakrishnan |
| 2009/0117620 A1 | 5/2009 | Fritchie et al. |
| 2009/0176280 A1 | 7/2009 | Hutchison, III et al. |
| 2009/0197248 A1 | 8/2009 | Griffiths et al. |
| 2009/0215050 A1 | 8/2009 | Jenison |
| 2009/0221096 A1 | 9/2009 | Torres |
| 2009/0298191 A1 | 12/2009 | Whitesides et al. |
| 2010/0022414 A1 | 1/2010 | Link et al. |
| 2010/0137152 A1 | 6/2010 | Gorfinkel et al. |
| 2010/0304387 A1 | 12/2010 | Jenison et al. |
| 2010/0308051 A1 | 12/2010 | Weber |
| 2011/0166044 A1 | 7/2011 | Jones et al. |
| 2011/0297866 A1 | 12/2011 | Weber |
| 2011/0303306 A1 | 12/2011 | Weber |
| 2011/0318728 A1 | 12/2011 | Phan et al. |
| 2012/0028342 A1 | 2/2012 | Ismagilov et al. |
| 2012/0264132 A1 | 10/2012 | Ismagilov et al. |
| 2013/0130226 A1 | 5/2013 | Lim et al. |
| 2013/0288348 A1 | 10/2013 | Breidenthal et al. |
| 2013/0331298 A1 | 12/2013 | Rea |
| 2014/0017730 A1 | 1/2014 | Hicke et al. |
| 2014/0038200 A1 | 2/2014 | Jenison et al. |
| 2014/0134619 A1 | 5/2014 | Jenison |
| 2014/0336064 A1 | 11/2014 | Ismagilov et al. |

FOREIGN PATENT DOCUMENTS

| | | |
|---|---|---|
| EP | 0816837 A1 | 1/1998 |
| EP | 1110084 B1 | 7/1999 |
| EP | 1036082 B1 | 5/2002 |
| EP | 0996547 B1 | 12/2002 |
| EP | 0808456 B1 | 5/2003 |
| EP | 0739240 B1 | 6/2004 |
| EP | 1287164 B1 | 10/2004 |
| EP | 1473084 A2 | 11/2004 |
| EP | 1080099 B1 | 2/2006 |
| EP | 1495119 B1 | 1/2007 |
| EP | 1641564 B1 | 10/2007 |
| EP | 1177318 B1 | 2/2008 |
| EP | 1173623 B1 | 6/2008 |
| EP | 1740722 B1 | 8/2008 |
| EP | 1382676 B1 | 5/2009 |
| EP | 1925678 B1 | 7/2009 |
| EP | 1380642 B1 | 3/2010 |
| EP | 1714134 B1 | 4/2010 |
| EP | 0875584 B1 | 9/2010 |
| EP | 1631685 B1 | 12/2010 |
| EP | 2305809 A2 | 4/2011 |
| EP | 1820552 B1 | 6/2011 |
| EP | 1679383 B1 | 7/2011 |
| EP | 1896180 B1 | 11/2011 |
| EP | 1630228 B1 | 1/2012 |
| EP | 2007905 B1 | 8/2012 |
| EP | 2016186 B1 | 1/2013 |
| EP | 1558934 B1 | 7/2013 |
| EP | 2276828 B1 | 7/2013 |
| GB | 2097692 A | 11/1982 |
| WO | WO 84/02000 A1 | 5/1984 |
| WO | WO 97/29508 A2 | 8/1997 |
| WO | WO 98/00231 A1 | 1/1998 |
| WO | WO 98/02237 A1 | 1/1998 |
| WO | WO 98/52691 A1 | 11/1998 |
| WO | WO 97/04297 A1 | 2/1999 |
| WO | WO 00/13014 A1 | 3/2000 |
| WO | WO 00/21666 A1 | 4/2000 |
| WO | WO 01/12327 A1 | 2/2001 |
| WO | WO 01/77683 A1 | 10/2001 |
| WO | WO 02/12856 A1 | 2/2002 |
| WO | WO 02/23163 A1 | 3/2002 |
| WO | WO 02/25243 A1 | 3/2002 |
| WO | WO 03/044221 A1 | 5/2003 |
| WO | WO 2004/038363 A2 | 5/2004 |
| WO | WO 2005/010169 A2 | 2/2005 |
| WO | WO 2005/016529 A1 | 2/2005 |
| WO | WO 2006/088876 A2 | 8/2006 |

(56) References Cited

FOREIGN PATENT DOCUMENTS

| WO | WO 2006/096571 A2 | 9/2006 |
|---|---|---|
| WO | WO 2006/101851 A2 | 9/2006 |
| WO | WO 2007/009082 A1 | 1/2007 |
| WO | WO 2007/021343 A2 | 2/2007 |
| WO | WO 2007/030501 A2 | 3/2007 |
| WO | WO-2007/044974 A2 | 4/2007 |
| WO | WO 2007/081385 A2 | 7/2007 |
| WO | WO 2007/081386 A2 | 7/2007 |
| WO | WO 2007/081387 A1 | 7/2007 |
| WO | WO 2007/089541 A2 | 8/2007 |
| WO | WO 2007/089777 A2 | 8/2007 |
| WO | WO 2007/133710 A2 | 11/2007 |
| WO | WO 2007/146923 A2 | 12/2007 |
| WO | WO 2008/002267 A1 | 1/2008 |
| WO | WO 2008/043041 A1 | 4/2008 |
| WO | WO 2008/048673 A2 | 4/2008 |
| WO | WO 2008/063227 A2 | 5/2008 |
| WO | WO 2008/069884 A2 | 6/2008 |
| WO | WO 2008/079274 A1 | 7/2008 |
| WO | WO 2008/097559 A2 | 8/2008 |
| WO | WO 2008/147382 A1 | 12/2008 |
| WO | WO 2009/002849 A2 | 12/2008 |
| WO | WO 2009/012420 A1 | 1/2009 |
| WO | WO 2009/013683 A1 | 1/2009 |
| WO | WO 2009/015390 A2 | 1/2009 |
| WO | WO 2009/018348 A1 | 2/2009 |
| WO | WO 2009/048673 A2 | 4/2009 |
| WO | WO 2009/070640 A2 | 6/2009 |
| WO | WO 2009/070742 A2 | 6/2009 |
| WO | WO 2009/071078 A1 | 6/2009 |
| WO | WO 2009/105648 A2 | 8/2009 |
| WO | WO 2009/149257 A1 | 12/2009 |
| WO | WO 2010/078420 A2 | 7/2010 |
| WO | WO 2010/083795 A1 | 7/2010 |
| WO | WO 2010/094249 A1 | 8/2010 |
| WO | WO 2011/109762 A1 | 9/2011 |
| WO | WO 2013/123238 A1 | 8/2013 |

OTHER PUBLICATIONS

Benner et al., "Synthetic Biology", Nat. Rev. Genet., Jul. 2005, 6, No. 7, 533-543.
Blainey et al., "Digital MDA for enumeration of total nucleic acid contamination", Nucleic Acids Res., 2011, 39, e19.
Brouzes et al., "Droplet microfluidic technology for single-cell high-throughput screening", Proc. Natl. Acad. Sci., 2009, 106, 14195-14200.
Chelliserrykattil et al., "Development of a Quantitative Real-Time Transcription-Mediated Amplification Assay for Simultaneous Detection of Multiple Nucleic Acid Analytes", J Mol. Diagn. 2009, 11, 680.
Cheng et al., "Research needs and challenges in the development of HIV diagnostic and treatment monitoring tests for use in resource-limited settings", Curr. Opin., HIV AIDS, 2008, 3, 495-503.
Choi et al., "Programmable in situ amplification for multiplexed imaging of mRNA expression," Nature Biotechnol, 2010, 28, 1208-1212.
Compton, "Nucleic acid sequence-based amplification", Nature, 1991, 350, 91-92.
de Baar et al., "One-tube real-time isothermal amplification assay to identify and distinguish human immunodeficiency virus type 1 subtypes A, B, and C and circulating recombinant forms AE and AG", J. Clin. Microbial., 2001, 39, 1895-1902.
Dean et al., "Comprehensive human genome amplification using multiple displacement amplification", Proc. Natl. Acad. Sci., 2002, 99, 5261-5266.
Dimov et al., "Integrated microfluidic tmRNA purification and real-time NASBA device for molecular diagnostics", Lab on a Chip, 2008, 8, 2071-2078.
Dirks et al., "Triggered Amplification by Hybridization Chain Reaction." Proceedings of the National Academy of Sciences of the United States of America, 2004, 101, No. 43, 15275-15278.
Du et al., "SlipChip", Lab Chip, 2009, 9, 2286-2292.
Esch et al., "Detection of Viable Cryptosporidium parvum Using DNA-Modified Liposomes in a Microfluidic Chip", Anal. Chern., 2001, 73, 2952-2958.
Fan et al., "Detection of Aneuploidy with Digital Polymerase Chain Reaction", Anal. Chern., 2007, 79, 7576-7579.
Fang et al., "Loop-Mediated Isothermal Amplification Integrated on Microfluidic Chips for Point-of-Care Quantitative Detection of Pathogens", Anal. Chern., 2010, 82, 3002-3006.
Genot et al, "Remote Toehold: A Mechanism for Flexible Control of DNA Hybridization Kinetics," JACS, 2011, 133 (7), 2177-2182.
Gibson et al., "A Novel Method for Real Time Quantitative RT-PCR", Genome Res., 1996, 6, 995-1001.
Graugnard et al., "Kinetics of DNA and Rna Hybridization in Serum and Serum-SDS", Nanotechnology, IEEE Transactions, 2010, 9, No. 5, 603-609.
Heid et al., "Real Time Quantitative PCR", Genome Res., 1996, 6, 986-994.
Hellyer et al., "Strand Displacement amplification: a versatile tool for molecular diagnostics", Expert Rev. Mol. Diagn., 2004, 4, 251-261.
Hill et al., "Direct Detection of Microorganisms in Clinical Specimens Using The Gen-Probe Transcription Meidated Amplification System", Clin. Chern., 1995, 41, S107.
International Patent Application No. PCT/US2008/071374: International Search Report dated Aug. 31, 2009, 7 pages.
International Patent Application No. PCT/US2010/028316: International Search Report dated May 10, 2010, 1 page.
Jarvius et al., "Digital quantification using amplified single-molecule detection", Nat. Methods, 2006, 3, 725-727.
Kalinina et al., "Nanoliter scale PCR with TaqMan detection", J. Nucleic Acids Res., 1997, 25, 1999-2004.
Kiss et al., "High-Throughput Quantitative Polymerase Chain Reaction in Picoliter Droplets", Anal. Chern., 2008, 80, 8975-8981.
Kreutz et al., "Theoretical Design and Analysis of Multivolume Digital Assays with Wide Dynamic Range Validated Experimentally with Microfluidic Digital PCR", Anal. Chern., 2011 83, 8158-8168.
Leng et al., "Agarose droplet microfluidics for highly parallel and efficient single molecule emulsion PCR", Lab on a Chip, 2010,10, 2841-2843.
Li et al., "A New Class of Homogeneous Nucleic Acid Probes Based on Specific Displacement Hybridization", Nucleic Acids Research, 2002, 30, No. e5.
Li et al., "Rational, modular adaptation of enzyme-free DNA circuits to multiple detection methods", Nucl. Acids Res., 2011, 1-13.
Li et al., "Dead-End Filling of SlipChip Evaluated Theoretically and Experimentally as a Function of the Surface Chemistry and the Gap Size between the Plates for Lubricated and Dry SlipChips", Langmuir, 2010, 26, 12465-12471.
Li et al., "Multiparameter Screening on SlipChip Used for Nanoliter Protein Crystallization Combining Free Interface Diffusion and Microbatch Methods", J. Am. Chern. Soc., 2009, 132, 112-119.
Li et al., "Protein Crystallization Using Microfluidic Technologies Based on Valves, Droplets, and Slip Chip", Annu. Rev. Biophys., 2010, 39, 139-158.
Li et al., "User-Loaded SlipChip for Equipment-Free Multiplexed Nanoliter-Scale Experiments", JACS, 2010, 132, 106-111.
Li et al., "Using a Multijunction Microfluidic Device to Inject Substrate into an Array of Performed Plugs without Cross-Contamination: Comapring Theory and Experiments", Anal. Chern., 2007, 79, 2756-2761.
Liu et al., "SlipChip for Immunoassays in Nanoliter Volumes", Anal. Chern., 2010, 82, 3276-3282.
Liu et al., "Solving the "World-to-Chip" Interface Problem with a Microfluidic Matrix", Anal. Chern., 2003, 75, 4718-4723.
Livak et al., "Analysis of Relative Gene Expression Data Using Real-Time Quantitative PCR and the $2^{-\Delta\Delta c}T$ Method", 2001, 25, 402-408.
Lizardi et al., "Mutation detection and single-molecule counting using isothermal rolling-circle amplification", Nature Genet., 1998, 19, 225-232.

(56) References Cited

OTHER PUBLICATIONS

Lo et al., "Digital PCR for the molecular detection of fetal chromosomal aneuploidy", Proc. Natl. Acad. Sci., 2007, 104, 13116-13121.
Lutz et al., "Microfluidic lab-on-a-foil for nucleic acid analysis based on isothermal recombinase polymerase amplification (RPA)", Lab on a Chip, 2010, 10, 887-893.
Mackay et al., "Real-time PCR in virology", Nucleic Acids Res., 2002, 30, 1292-1305.
Mazutis et al., "Droplet-Based Microfluidic Systems for High-Throughput Single DNA Molecule Isothermal Amplification and Analysis", Anal. Chem., 2009, 81, 4813-4821.
Nacht et al., "Molecular characteristics of non-small cell lung cancer", Proc. Natl. Acad. Sci., 2001, 98, 15203-15208.
Notomi et al., "Loop-mediated isothermal amplification of DNA", Nucleic Acids Res., 2000, 28, 7 pages.
Ottesen et al., "Microfluidic Digital PCR Enables Multigene Analysis of Individual Environmental Bacteria", Science, 2006, 314, 1464-1467.
Piche et al., "Optimization of in Vitro Transcription and Full-Length cDNA Synthesis Using the T4 Bacteriophage Gene 32 Protein", J Biomol. Tech., 2005, 16, 239-247.
Picuri et al., "Universal Translators for Nucleic Acid Diagnosis" Journal of the American Chemical Society, 2009, 131, No. 26, 9368-9377.
Piepenburg et al., "DNA Detection Using Recombination Proteins", PLoS Bioi. 2006, 4, 1115-1121.
Preiser et al., "HIV-1 Viral Load Assays for Resource-Limited Settings: Clades Matter", PLoS Med., 2006, 3, e538.
Qian et al., "Scaling up Digital Circuit Computation with DNA Strand Displacement Cascades" Science, 2011, 332, No. 6034, 1196-1201.
Seelig et al., "Enzyme-Free Nucleic Acid Logic Circuits," Science, Dec. 8, 2006, 1585-1588.
Shamoo et al., "Crystal structure of a replication fork single-stranded DNA binding protein (T4 gp32) complexed to DNA", Nature, 1995, 376, 362-366.
Shen et al., "Digital Isothermal Quantification of Nucleic Acids via Simultaneous Chemical Initiation of Recombinase Polymerase Amplification Reactions on SlipChip", Analytical Chemistry, 2011, 83, 3533-3540.
Shen et al., "Digital PCR on a SlipChip", Lab on a Chip, 2010, 10, 2666-2672.
Shen et al., "Multiplexed Quantification of Nucleic Acids with Large Dynamic Range Using Multivolume Digital RT-PCR on a Rotational SlipChip Tested with HIV and Hepatitis C Viral Load", JACS, 2011, 133, 17705-17712.
Shen et al., "Nanoliter Multiplex PCR Arrays on a SlipChip", Analytical Chemistry, 2010, 82, 4606-4612.
Song et al., "A Microfluidic System for Controlling Reaction Networks in Time", Angew. Chem.-Int. Edit., 2003, 42, 768-772.
Sundberg et al., "Spinning Disk Platform for Microfluidic Digital Polymerase Chain Reaction", Anal. Chem., 2010, 82, 1546-1550.
Sykes et al., "Quantitation of Targets for PCR by Use of Limiting Dilution", Biotechniques, 1992, 13, 444-449.
Tewhey et al., "Microdroplet-based PCR enrichment for large-scale targeted sequencing", Nat. Biotechnol. 2009, 27, 1025-1031.
Thorsen et al., "Microfluidic Large-Scale Integration", Science, 2002, 298, 580-584.
Tsongalis et al., "Branched DNA Technology in Molecular Diagnostics" American journal of clinical pathology, 2006, 126, No. 3, 448-453.
UNAIDS, "UNAIDS/WH Report on the Global AIDS Epidemic", UNAIDS/WHO, 2008, 362 pages.
Van Ness et al., "Isothermal Reactions for the Amplification of Oligonucleotides" Proceedings of the National Academy of Sciences, 2003, 100, No. 8, 4504-4509.
Vet et al., "Multiplex detection of four pathogenic retroviruses using molecular beacons", Proc. Natl. Acad. Sci., 1999, 96, 6394-6399.
Vincent et al., "Helicase-dependant isothermal DNA amplification", EMBO Rep., 2004, 5, 795-800.
Vogelstein et al., "Digiatl PCR", Proc. Natl. Acad. Sci., 1999, 96, 9236-9241.
Walker et al., "Strand displacement amplification—an isothermal, in vitro DNA amplification technique", Nucleic Acids Res., 1992, 20, 1691-1696.
Yin et al., "Programming Biomolecular Self-Assembly Pathways", Nature, 2008, 451, No. 7176, 318-322.
Zhang et al., "A DNA-Origami Chip Platform for Label-Free SNP Genotyping Using Toehold-Mediated Strand Displacement", Small, 2010, 6, No. 17, 1854-1858.
Zhang et al., "Control of DNA Strand Displacement Kinetics Using Toehold Exchange" Journal of the American Chemical Society, 2009, 131, No. 47, 17303-17314.
Zhang et al., "Engineering Entropy-Driven Reactions and Networks Catalyzed by DNA.", Science, 2007, 318, No. 5853, 1121-1125.
Zheng et al., "A Microfluidic Approach for Screening Submicroliter Volumes against Multiple Reagents by Using Performed Arrays of Nanoliter Plugs in a Three-Phase Liquid/Liquid/Gas Flow", Angew. Chem. Int. Ed., 2005, 44, 2520-2523.
U.S. Appl. No. 14/177,190, filed Feb. 10, 2014, Ismagilov et al.
U.S. Appl. No. 14/177,194, filed Feb. 10, 2014, Ismagilov et al.
Abhyankar, Vinay V. et al., "Spatiotemporal Micropatterning of Cells on Arbitrary Substrates", Anal. Chem., vol. 79, (2007), pp. 4066-4073.
Abrams, William R., et al., "Development of a Microfluidic Device for Detection of Pathogens in Oral Samples Using Upconverting Phoshor Technology (UPT)," Ann. N.Y. Acad. Sci. 1098: (2007), pp. 375-388.
Adamson, David N. et al., "Production of Arrays of Chemically Distinct Nanolitre Plugs via Repeated Splitting in Microfluidic Devices", Lab on a Chip, vol. 6, (2006), pp. 1178-1186.
Aharoni, Amir, et al., "High-Throughput Screening of Enzyme Libraries: Thiolactonases Evolved by Fluorescence-Activated Sorting of Single Cells in Emulsion Compartments," Chem. Biol., vol. 12, (2005), pp. 1281-1289.
Ajaev, Vladimir S., et al. "Steady Vapor Bubbles in Rectangular Microchannels", Journal of Colloid and Interface Science, vol. 240, (2001), pp. 259-271.
Ajaev, Vladimir S., et al. "Three-Dimensional Steady Vapor Bubbles in Rectangular Microchannels", Journal of Colloid and Interface Science, vol. 244, (2001), pp. 180-189.
Akselband, Y. et al., "Rapid Mycobacteria Drug Susceptibility Testing Using Gel Microdrop (GMD) Growth Assay and Flow Cytometry", J. Microbiol. Methods, vol. 62, (2005), pp. 181197.
Alberts, Bruce et al., "Chapter 22—Histology: The Lives and Deaths of Cells in Tissues", Molecular Biology of the Cell (Garland Publishing, 2002), pp. 1259-1312.
Alizadeh, Ash A. et al., "Genomic-Scale Gene Expression Profiling of Normal and Malignant Immune Cells", Current Opinion in Immunology, vol. 12, No. 2, (2000), pp. 219-225.
Alter,Orly et al., "Singular Value Decomposition for Genome-Wide Expression Data Processing and Modeling", PNAS (2000), vol. 97, No. 18, pp. 10101-10106.
Altreuter, David H. et al., "Combinatorial Biocatalysis: Taking the Lead From Nature", Current Opinion in Biotechnology vol. 10, No. 2, (1999), pp. 130-136.
Anderson, Megan J. et al., "Phase Knowledge Enables Rational Screens for Protein Crystallization,"PNAS, vol. 103, No. 45, (2006) pp. 16746-16751.
Andersson, Helene et al., "Microfluidic Devices for Cellomics: A Review,"Sensors and Actuators B-Chemical 92, (2003), pp. 315-325.
Androulakis,I.P. et al., "Analysis of Time-Series Gene Expression Data: Methods, Challenges, and Opportunities,", Annual Review of Biomedical Engineering, vol. 9, (2007), pp. 205-228.
Armstrong, Gavin, *"Microfluidics: Introducing the Chemstrode,"Nature* Chemistry, Nov. 14, 2008.
Arrizon, Victor et al., "Talbot Array Illuminators with Liquid Crystal Displays,"Opt. Eng., vol. 37, No. 1, (1997), pp. 189-197.

(56) References Cited

OTHER PUBLICATIONS

Aryan, Ehsan et al., "A Novel and More Sensitive Loop-Mediated Isothermal Amplification Assay Targeting IS6110 for Detection of *Mycobacterium* Tuberculosis Complex," Microbiol Research vol. 165, (2010), pp. 211-220.

Atencia, Javier, et al. "Controlled Microfluidic Interfaces", Nature, 2005, vol. 437, No. 29, pp. 648-655.

Baker, Carolyn N., et al., "Evaluation of alamar Colorimetric Broth Microdilution Susceptibility Testing Method for *Staphylococci* and *Enterococci*," J. Clin. Microbiol., vol. 34, (1996), pp. 2654-2659.

Balakrishnan, Pachamuthu, et al., "Low-Cost Monitoring of HIV Infected Individuals on Highly Active Antiretroviral Therapy (HAART) in Developing Countries", vol. 121, (2005), pp. 345355.

Balasubramanian, Priya et al., "Confocal Images of Circulating Tumor Cells Obtained Using a Methodology and Technology That Removes Normal Cells,"Molecular Pharmaceutics, vol. 6, No. 5, (2009) pp. 1402-1408.

Balslev, Daniela et al., "Cluster Analysis of Activity-Time Series in Motor Learning," Human Brain Mapping, vol. 15, No. 3, (2002), pp. 135-145.

Bang, Hyunwoo et al., "Serial Dilution Microchip for Cytotoxicity Test," Journal of Micromechanics and Microengineering, vol. 14, (2004), pp. 1165-1170.

Bange, Adam et al., Microfluidic Immunosensor Systems, Biosensors and Bioelectronics, vol. 20, (2005), pp. 2488-2503.

Barbieri, Laura et al., "Water Wetting Transition parameters of Perfluorinated Substrates with Periodically Distributed Flat-top Microscale Obstacles," Langmuir, vol. 23, (2007), pp. 17231734.

Baret, Jean-Christophe et al., "Fluorescence-Activated Droplet Sorting (FADS): Efficient Microfluidic Cell Sorting based on Enzymatic Activity," Lab Chip, vol. 9, (2009), pp. 1850-1858.

Bar-Joseph, Ziv "Analyzing Time Series Gene Expression Data," Bioinformatics, vol. 20, No. 16 (2004), pp. 2493-2503.

Bar-Nahum, Itsik et al., "Mild, Aqueous, Aerobic, Catalytic oxidation of Methane to Methanol and Acetaldehyde Catalyzed by a Supported Bipyrimidinylplatinum-Polyoxometalate Hybrid Compound," J. Am. Chem. Soc., vol. 126, (2004), pp. 10236-10237.

Beard, Daniel A. et al., "Dispersion of a Solute in a Microfluidic Channel,"Journal of Applied Physics, vol. 89, No. 8, (2001), pp. 4667-4669.

Becker, Frederick F. et al. "Separation of Human Breast-Cancer Cells from Blood by Differential Dielectric Affinity," Proc. Nat'l. Acad. of Sci., vol. 92, (1995) pp. 860-864.

Beebe, David J. et al., "Physics and Applications of Microfluidics in Biology," Rev. Biomed. Eng. vol. 4 (2002) pp. 261-286.

Beer, Reginald N. et al. "On-Chip, Real-Time, Single-Copy Polymerase Chain Reaction in Picoliter Droplets", Anal. Chem., 2007, v. 79, pp. 8471-8475.

Behrens, Heidi L. et al., "Combining Microdialysis, NanoLC-MS, and MalDI-TOF/TOF to Detect Neuropeptides Secreted in the Crab, *Cancer borealis*," Analytical Chemistry, vol. 80, No. 18, (2008), pp. 6949-6958.

Beliaeff, Benoit et al., "The Most "Probable Number" Estimate and its Confidence Limits," Water Res. vol. 27, No. 5, (1993), pp. 799-805.

Bergens, Steven H. et al., "A Redox Fuel Cell That Operates with Methane as Fuel at 120 Degrees C,"Science, vol. 265, (1994), pp. 1418-1420.

Berger, Rachel Pardes et al., "Multiplex Assessment of Serum Biomarker Concentrations in Well-Appearing Children With Inflicted Traumatic Brain Injury" Pediatric Research, vol. 65, No. 1, pp. 97-102.

Berger, Rachel Pardes, et al., "Urinary S1008 Concentrations are Increased After Brain Injury in Children: A Preliminary Study," Pediatric Critical Care Medicine, vol. 7, No. 6, (2006), pp. 557-561.

Bergh, Sam et al., "Combinatorial Heterogeneous Catalysis: Oxidative Dehydrogenation of Ethane to Ethylene, Selective Oxidation of Ethane to Acetic Acid, and Selective Ammoxidation of propane to Acrylonitrile,", Topics in Catalysis, vol. 23, Nos. 1-4, pp. 65-79.

Bergman, Robert G. et al., "Computational Study of Methane Activation by TpRe(CO)2 and CpRe(CO)2 wit ha Steroelectronic Comparison of Cyclopentadienyl and Scorpianate Ligands,"Organometallics, vol. 22,(2008), pp. 2331-2337.

Berthier, Erwin et al., "Managing Evaporation for More Robust Microscale Assays part 2. Characterization of convection and Diffusion for Cell Biology," Lab Chip, vol. 8, (2008), pp. 860-864.

Bhat, Somanath et al., "Single Molecule Detection in Nanofluidic Digital Array Enables Accurate Measurement of DNA Copy Number," Anal. Bioanal. Chem., vol. 394, (2009), pp. 457-467.

Biswal, Sibani Lisa et al., "Micromixing with Linked Chains of Paramagnetic Particles," Analytical Chemistry, vol. 76, No. 21, (2004) pp. 6448-6455.

Blicharz,Timothy M. et al., "Fiber-Optic Microsphere-Based Antibody Array for the Analysis of Inflammatory Cytokines in Saliva"Analytical Chemistry, vol. 81, No. 6, (2009) pp. 2106-2114.

Blyth, Brian J. et al, "Validation of Serum Markers for Blood-Brain Barrier Disruption in Traumatic Brain Injury"Journal of Neurotrauma, vol. 26, (2009), pp. 1497-1507.

Boccazzi, Paolo et al., "Gene Expression Analysis of *Escherichia coli* Grown in Miniaturized Bioreactor Platforms for High-Throughput Analysis of Growth and Genomic Data,", App. Microbio. Biotech., vol. 68, (2005), pp. 518-532.

Boedicker,James Q. et al., "Detecting Bacteria and Determining Their Susceptibility to Antibiotics by Stochastic Confinement in Nanoliter Droplets Using Plug-Based Microfluidics," Lab Chip vol. 8, (2008), pp. 1265-1272.

Boom, R. et al., "Rapid and Simple Method for Purification of Nucleic Acids,"Journal of Clinical Microbiology, vol. 28, (1990), pp. 495-503.

Boukellal, Hakim et al., "Simple, Robust Storage of Drops and Fluids in a Microfluidic Device,". Lab Chip, vol. 9, (2009), pp. 331-338.

Bourne, James A. "Intracerebral Microdialysis: 30 Years as a Tool for the Neuroscientist," Clinical and Experimental Pharmacology and Physiology, vol. 30, (2003), pp. 16-24.

Brambilla, Don et al., "Multicenter Evaluation of Use of Dried Blood and Plasma Spot Specimens in Quantitative Assays for Human Immunodeficiency Virus RNA: Measurement, Precision, and RNA Stability,"Journal of Clinical Microbiology, vol. 41, No. 5, (2003), pp. 1888-1893.

Braslaysky, Ido et al., "Objective-Type Dark-Field Illumination for Scattering from Microbeads" Applied Optics, vol. 40, No. 31, (2001), pp. 5650-5657.

Bringer, Michelle R. et al., "Microfluidic Systems for Chemical Kinetics that Rely on Chaotic Mixing in Droplets,"Phil. Trans. R. Soc. Lond. A vol. 362, (2004), pp. 1087-1104.

Bronzeau, Sandrine et al., "Simultaneous Bioassays in a Microfluidic Channel on Plugs of Different Magnetic Particles", Analytica Chimica Acta, vol. 609 (2008), pp. 105-112.

Brown, Michael P.S. et al., "Knowledge-Based Analysis of Microarray Gene Expression Data by Using Support Vector Machines,"PNAS, vol. 97, No. 1, (2000), pp. 262-267.

Bruls, D.M. et al., Rapid Integrated Biosensor for Multiplexed Immunoassays Based on Actuated Magnetic Nanoparticles, Lab Chip, vol. 9, (2009), pp. 3504-3510.

Burns, Mark A. et al. "Microfabricated structures for integrated DNA analysis", Proc. Natl. Acad. Sci. USA, May 1996, vol. 93, pp. 5556-5561.

Cady, Nathaniel C. et al., A Microchip-Based DNA Purification and Real-Time PCR Biosensor for Bacterial Detection, Sensors, Proceedings of IEEE 24-27, vol. 3, (2004), pp. 1191-1194.

Calmy, alexandra et al., "HIV Viral Load Monitoring in Resource-Limited Regions: Optional or Necessary?"CID, vol. 44, (2007), pp. 128-134.

Carpenter, John F. et al., "Long-Term Storage of Proteins," Current Protocols in Protein Science, Unit 4.6.1 Supplement 27, (2002), 6p.

Carrette, Odile et al., "State-of-the-Art Two-Dimensional Gel Electrophoresis: A Key Tool of Proteomics Research," Nature Protocols, vol. 1, No. 2 (2006), pp. 812-823.

(56) References Cited

OTHER PUBLICATIONS

Cellar, Nicholas A. et al., "Microfluidic Chip for Low-Flow Push-Pull Perfusion Sampling in Vivo with On-Line Analysis of Amino Acids," Analytical Chemistry, vol. 77, No. 21, (2005), pp. 7067-7073.
Cernak, Ibolja "Animal Models of Head Trauma,"NeuroRx Journal of the American Society for Experimental NeuroTherapeutics, vol. 2, (2005), pp. 410-422.
Chabert, Max et al., "Microfluidic High-Throughput Encapsulation and Hydrodynamic Self-Sorting of Single Cells," PNAS, vol. 105, No. 9, (2008), pp. 3191-3196.
Charbonniere, Loie J. et al., "Lanthanide Complexes and Quantum Dots: A Bright Wedding for Resonance Energy Transfer," European Journal of Inorganic Chemistry, (2008), pp. 32413251.
Chase, et al., Stimulus-Induced Release of Substances from Olfactory Bulb Using Push-Pull Cannula. Nature, vol. 217 (5127) (1968), pp. 466.
Chayen, Naomi E. "Comparative Studies of Protein Crystallization by Vapour-Diffusion and Microbatch Techniques,"Acta Crystallogr. D54, (1998) pp. 8-15.
Chayen, Naomi E. "Turning Protein Crystallization from an Art into a Science,"Current Opinion in Structural Biology, vol. 14, (2004), pp. 577-583.
Chayen, Naomi E. A Novel Technique to Control the Rate of Vapour Diffusion, Giving Larger Protein Crystals,J. Appl. Crystallogr., vol. 30, (1997), pp. 198-202.
Chayen, Naomi E. et al., "Protein Crystallization: From Purified Protein to Diffraction-Quality Crystal,"Nature Methods, vol. 5, No. 2, (2008), pp. 147-153.
Chayen, Naomi E., "Crystallization with oils: a new dimension in macromolecular crystal growth," Journal of Crystal Growth, 1999, vol. 196, pp. 434-441.
Chen, Chihchen et al., "Microfluidic Isolation and Transcriptome Analysis of Serum Microvesicles," Lab on a Chip, vol. 10, (2010), pp. 505-511.
Chen, Delai L. et al., "Microfluidic Cartridges Preloaded with Nanoliter Plugs of Reagents: An alternative to 96-Well Plates for Screening," Current Opinion in Chemical Biology, vol. 10, No. 3, (2006), pp. 226-231.
Chen, Delai L. et al., "The Chemistrode: A Droplet-Based Microfluidic Device for Stimulation and Recording with High Temporal, Spatial, and Chemical Resolution,"PNAS, vol. 105, No. 44, (2008), pp. 16843-16848.
Chen, Delai L. et al., "Using Microfluidics to Observe the Effect of Mixing on Nucleation of Protein Crystals,", J. Am. Chem. Soc., vol. 127, (2005), pp. 9672-9673.
Chen, Delai L. et al., "Using Three-Phase Flow of Immiscible Liquids to Prevent Coalescence of Droplets in Microfluidic Channels: Criteria to Identify the Third Liquid and Validation with Protein Crystallization" Langmuir, vol. 23, No. 4, (2007), pp. 2255-2260.
Chen, Delai L. et al., "Using TIRF Microscopy to Quantify and Confirm Efficient Mass Transfer at the Substrate Surface of the Chemistrode,", New Journal of Physics, vol. 11, (2009), 075017, (9pp).
Chen, Grace D. et al., "Concentration and Purification of Human Immunodeficiency Virus Type 1 Virions by Microfluidic Separation of Superparamagnetic Nanoparticles,", Analytical Chemistry, vol. 82, No. 2, (2010), pp. 723-728.
Chen, Zuliang, et al., "Separation of Chromium (111) and Chromium (VI) by Capillary Electrophoresis using 2,6-Pyridinedicarboxylic Acid as a Pre-Column Complexation Agent," Journal of Chromatography A, vol. 927, (2001), pp. 219-227.
Cheng, Ben et al., "Research Needs and Challenges in the Development of HIV Diagnostic and Treatment Monitoring Tests for Use in Resource-Limited Settings,", Current Opinion in HIV and AIDS, vol. 3, (2008), pp. 495-503.
Chiu , Daniel T. et al., "Chemical Transformations in Individual Ultrasmall Biomimetic Containers,"Science, vol. 283, (1999), pp. 1892-1895.

Chiu, Daniel T. et al., Droplets for Ultrasmall-Volume Analysis, Analytical Chemistry, vol. 81, No. 13, (2009) pp. 5111-5118.
Chu, Kuan-Lun et al., "Nanoporous Silicon Membrane Electrode Assembly for On-Chip Micro Fuel Cell Application,"Journal of Microelectromechanical Systems, vol. 15, No. 3, (2006), pp. 671-677.
Chung, Bong Geun et al., "Human Neural Stem Cell Growth and Differentiation in a Gradient-Generating Mcirofluidic Device," Lab Chip, vol. 5, (2005), pp. 401-406.
Chung, Su Eun et al., "Optofluidic Encapsulation and Manipulation of Silicon Microchips Using Image Processing Based Optofluidic Maskless Lithography and Railed Microfluidics," Lab Chip, vol. 9, (2009) pp. 2845-2850.
Clausell-Tormos, Jenifer et al., "Droplet-Based Microfluidic Platforms for the Encapsulation and Screening of Mammalian Cells and Multicellular Organisms," Chemistry & Biology, vol. 15, (2008), pp. 427-437.
Clopper, C.J. et al., "The Use of Confidence or Fiducial Limis Illustrated in the Case of the Binomial," Biometrika vol. 26, No. 4, (1934), pp. 404-413.
Cochran, William G. "Estimation of Bacterial Densities by Means of the Most Probable Number,", Biometrics, vol. 6, (1950), pp. 105-116.
Cohen, Aina E. "An Automated system to Mount Cryo-Cooled Protein Crystals on a Synchrotron Beamline, Using Compact Sample Cassettes and a Small-Scale Robot," J. of Appl. Crystallogr. , vol. 35, (2002), pp. 720-726.
Cohen, Jon "The Marketplace of HIV/alD$"Science, New Series, vol. 272, No. 5270 (1996), pp. 1880-1881.
Cohen, Michael H. et al., "Microfabrication of Silicon-Based Nanoporous Particulates for Medical Applications,"Biomedical Microdevices, vol. 5, No. 3, (2003), pp. 253-259.
Collins, Francis S. "*Opportunities for Research and NIH*," Science, vol. 327, (2010) pp. 36-37.
Cookson, P. et al., "A Simple Spectrophotometric Method for the Quantification of Residual Haemoglobin in Platelet Concentrates,"Vox Sanguinis, vol. 87, (2004), pp. 264-271.
Cooper, Joshua D. et al., "Evaluation of an Osmotic Pump for Microdialysis Sampling in an Awake and Untethered Rat,"Journal of Neuroscience Methods, vol. 160 (2007), pp. 269-275.
Corma, A. et al., "Discovery of New Paraffin Isomerization Catalysts Based on So42-/Zr02 and Wox/Zr02 Applying Combinatorial Techniques,"Catalysis Today, vol. 81, (2003), pp. 495-506.
Crowe, Suzanne et al., "Monitoring of Human Immunodeficiency Virus Infection in Resource-Constrained Countries,"CID, vol. 37, Suppl 1, (2003) pp. S25-S35.
Crowley, Timothy A. et al., "Isolation of Plasma From Whole Blood Using Planar Microfilters for Lab-on-a-Chip Applications,"Lab Chip, vol. 5, (2005), pp. 922-929.
Curtis, Kelly A. et al., "Rapid Detection of HIV-1 by Reverse-Transcription, Loop-Mediated Isothermal Amplification (RT-LAMP)"Journal of Virological Methods, vol. 151, (2008), pp. 264-270.
Dai, Jinhua et al., "Electrokinetic Trapping and Concentration Enrichment of DNA in a Microfluidic Channel,"Journal of the American Chemical Society, vol. 125, (2003), pp. 13026-13027.
Danna, Erika A. et al., "Transcending the Biomarker Mindset: Deciphering Disease Mechanisms at the Single Cell Level,"Curr. Opin. Chem. Biol., vol. 10, (2006), pp. 20-27.
De Man, J.C. et al., "MPN Tables, Corrected,"Eur. J. Appl. Microbiol. Biotech. vol. 17, No. 5 (1983), pp. 301-305.
Dear, Paul H. et al., "Happy Mapping: Linkage Mapping Using a Physical Analogue of Meiosis," Nucleic Acids Research, vol. 21, No. 1, (1993), pp. 13-20.
de-Bashan, Luz E. et al., "Removal of ammonium and phosphorus ions from synthetic wastewater by the microalgae *Chlorella vulgaris* coimmobilized in alginate beads with the microalgae growth-promoting bacterium Azospirillum brasilense," 2002, vol. 36, pp. 29412948.
DeFina, Philip et al., "The New Neuroscience Frontier: Promoting Neuroplasticity and Brain Repair in Traumatic Brain Injury,"The Clinical Neuropsychologist, vol. 23, No. 8, (2009), pp. 1391-1399.

(56) References Cited

OTHER PUBLICATIONS deJong, J. B. et al., "New Replication Technique for the Fabrication of Thin Polymeric Microfluidic Devices with Tunable Porosity," Lab Chip—Miniaturisation for Chemistry and Biology, vol. 5, No. 11, (2005), pp. 1240-1247.
Delamarche, Emmanuel et al., Microfluidics for Processing Surfaces and Miniaturizing Biological Assays, Adv. Mater. vol. 17, (2005) pp. 2911-2933.
DeLellis, et al., "The Neurometabolic Cascade and Implications of mTBI: Mitigating Risk to the SOF Community,"Journal of Special Operations Medicine: A Peer Reviewed Journal for SOF Medical Professionals, vol. 9, No. 4, (2009), pp. 36-42.
deMello, Andrew J. et al., "Control and Detection of Chemical Reactions in Microfluidic Systems," Nature 2006, vol. 442, pp. 394-402.
Dequeant, Mary-Lee et al., "A Complex Oscillating Network of Signaling Genes Underlies the Mouse Segmentation Clock,"Science, vol. 314, (2006) p. 1595-1598.
Desai, Tejal A. et al., "Nanoporous Anti-Fouling Silicon Membranes for Biosensor Applications"Biosensors & Bioelectronics, vol. 15, (2000), pp. 453.462.
Dharmasiri, Udara et al., "Highly Efficient Capture and Enumeration of Low Abundance Prostate Cancer Cells Using Prostate-Specific Membrane Antigen Aptamers Immobilized to a Polymeric Microfluidic Device" Electrophoresis, vol. 30, (2009), pp. 3289-3300.
Dhopeshwarkar Rahul et al., "Transient Effects on Microchannel Electrokinetic Filtering with an Ion-Permselective Membrane," Analytical Chemistry, vol. 80, (2008), pp. 1039-1048.
Dhopeshwarkar, Rahul et al., "Electrokinetic Concentration Enrichment Within a Microfluidic Device Using a Hydrogel Microplug," Lab Chip, vol. 5, (2005), pp. 1148-1154.
Dhouib, Kaouthar et al., "Microfluidic Chips for the Crystallization of Biomacromolecules by Counter-Diffusion and On-Chip Crystal X-ray Analysis," Lab Chip, vol. 9, (2009), pp. 14121421.
Di Carlo, Dino et al., "Dynamic Single Cell Culture Array". Lab Chip, vol. 6, (2006), pp. 1445-1449.
Di Giusto, Daniel A. et al., "Proximity Extension of Circular DNA Aptamers with Real-Time Protein Detection," Nucleic Acids Research, vol. 33, No. 6, (2005), pp. 33-64.
Diercks, alan H. et al., A Microfluidic Device for Multiplexed Protein Detection in Nano-Liter Volumes, Anal. Biochem., vol. 386, (2009), pp. 30-35.
Dimov, Ivan K. et al., "Integrated Microfluidic tmRNA Purification and Real-Time NASBA Device for Molecular Diagnostics," Lab Chip, vol. 8, (2008), pp. 2071-2078.
Dittrich, Petra S. et al., "Lab-on-a-Chip: Miocrofluidics in Drug Discovery," Nat. Rev., vol. 5, (2006), pp. 210-218.
Dodge, Arash et al., "Electrokinetically Driven Microfluidic Chips with Surface-Modified Chambers for Heterogeneous Immunoassays,"Anal. Chem., vol. 73, No. 14, (2001), pp. 3400-3409.
Dong, Yongzhi et al., "Heterogeneous Immunosensing Using Antigen and Antibody Monolayers on Gold Surfaces with Electrochemical and Scanning Probe Detection,"Anal. Chem., vol. 72, No. 11, (2000), pp. 2371-2376.
Douglas-Jones, Anthony G. et al., "Molecular Assessment of Sentinel Lymph Node in Breast Cancer Management", Histopathology, No. 55, (2009), pp. 107-113.
Drosten, Christian et al., "Ultrasensitive Monitoring of HIV-I Viral Load by a Low-Cost Real-Time Reverse Transcription-PCR Assay with Internal Control for the 5' Long Terminal Repeat Domain,"Clin Chem. vol. 52, (2006), pp. 1258-1266.
Du, Wen-Bin et al., "High-Throughput Nanoliter Sample Introduction Microfluidic Chip-Based Flow Injection Analysis System with Gravity-Driven Flows," Analytical Chemistry, vol. 77, No. 5, (2005), p. 1330.
Du, Wenbin et al., "SlipChip", Lab Chip, vol. 9, (2009), pp. 2286-2292.
Dube, Simant et al., "Mathmatical Analysis of Copy Number Variation in a DNA Sample Using Digital PCR on a Nanofluidic Device,"PLoS One, vol. 3, No. 8, (2008), p. e2876.
Duffy, David C. et al., "Rapid Prototyping of Microfluidic systems in Poly(dimethylsiloxane)," Anal. Chem., vol. 70, No. 23, (1998), pp. 4974-4984.
Durbin, S.D. et al., "Protein Crystallization," Annu. Rev. Phys. Chem. vol. 47, (1996), pp. 171204.
Edd, Jon F. et al., "Nucleation and Solidification in Static Arrays of Monodisperse Drops," Lab Chip, vol. 9, (2009), pp. 1859-1865.
Eddaoudi, Mohamed et al., "Modular chemistry: Secondary Building Units as a Basis for the Design of Highly Porous and Robust Metal—organic Carboxylate Frameworks,"Acc. Chem. Res., vol. 34 (2001), pp. 319-330.
Eisen, Michael B. et al., "Cluster Analysis and Display of Genome-Wide Expression Patterns," Proc. Natl. Acad. Sci., vol. 95, (1998), pp. 14863-14868.
Ekstrand, D. Henric et al., "A Sensitive Assay for the Quantification of Reverse Transcriptase Activity Based on the Use of Carrier-Bound Template and Non-Radioactive-Product Detection, with Special Reference to Human-Immunodeficiency-Virus Isolation," Biotechnol. Appl. Biochem. vol. 23, (1996), pp. 95-105.
El-ali, Jamil, et al., "Cells on Chips," Nature, vol. 442, (2006,) pp. 403-411.
Emamzadah, Soheila et al., "Cyclic Olefin Homopolymer-Based Microfluidics for Protein Crystallization and In Situ X-Ray Diffraction,"Acta Crystallogr. vol. D65, (2009), pp. 913-920.
Emsley, Paul, et al., "Coot: Model-Building Tools for Molecular Graphics," Sect. D-Biol. Crystallogr., vol. D60, (2004), pp. 2126-2132.
Eon-Duval, alex et al., "Purification of Pharmaceutical-Grade Plasmid DNA by Anion-Exchange Chromatography in an RNase-Free Process," J. Chromatogr., vol. 804 (2004), pp. 327-335.
Epstein, Jason R. et al., "Fluorescence-Based Nucleic Acid Detection and Microarrays," Anal. Chim. Acta, vol. 469 (2002) pp. 3-36.
Ernst, Jason et al., "Clustering Short Time Series Gene Expression Data,"Bioinformatics, vol. 21 Suppl. 1 (2005), pp. 159-168.
Fan, alice C. et al., "Nanofluidic Proteomic Assay for Serial Analysis of Oncoprotein Activation in Clinical Specimens," Nature Medicine, vol. 15, No. 5, (2009), pp. 566-571.
Fan, Christina et al., "Digital PCR Enables Rapid Prenatal Diagnosis of Fetal Aneuploidy," Am. J. Obstet. Gynecol., (2008), pp. 199.
Fan, H. Christina et al., "Microfluidic Digital PCR Enables Rapid Prenatal Diagnosis of Fetal Aneuploidy," American Journal of Obstetrics & Gynecology, (2009), pp. 543.e1-543.e7.
Fan, Rong et al. "Integrated Barcode Chips for Rapid, Multiplexed Analysis of Proteins in Microliter Quantities of Blood,"Nature Biotechnology, vol. 26, No. 12 (2008), pp. 373-1378.
Fekl, Ulrich et al., "Homogeneous Hydrocarbon C—H Bond Activation and Functionalization with Platinum," Adv. Inorg. Chem., vol. 54, (2003), pp. 259-320.
Fidler, Isaiah J. et al., "The Pathogenesis of Cancer Metastasis: The 'Seed and Soil' Hypothesis Revisited,"Nature Reviews Cancer, vol. 3, (2003) pp. 453-458.
Filkov, Vladimir et al., "Analysis Techniques for Microarray Time-Series Data"Journal of Computational Biology, vol. 9, No. 2, (2002), pp. 317-330.
Fiscus, et al. "HIV-1 Viral Load Assays for Resource-Limited Settings", PLoS Medicine, vol. 3, No. 10 (2007), pp. 1743-1750.
Franzblau, Scott G. et al., "Rapid Low-Technology MIC Determination with Clinical *Mycobacterium tuberculosis* Isolates by Using the Microplate alamar Blue Assay,"J. Clin. Microbiol., vol. 36, No. 2 (1998), pp. 362-366.
Fu, Elain et al., "Modeling of a Competitive Microfluidic Heterogeneous Immunoassay: Sensitivity of the Assay Response to Varying System Parameters,"Anal. Chem., vol. 81, (2009) pp. 3407-3413.
Gambi, Cecilia M.C. et al., "Dynamic percolation in fluorinated water-in-oil microemulsions", Physical Review E. Oct. 1997, v 56, No. 4, pp. 4356-4363.

(56) References Cited

OTHER PUBLICATIONS

Gao, Jian et al., "Integration of Single Cell Injection, Cell Lysis, Separation and Detection of Intracellular Constituents on a Microfluidic Chip," Lab Chip, vol. 4, (2004), pp. 47-52.
Garcia-Ruiz, et al., "Investigations on Protein Crystal Growth by the Gel Acupuncture Method," Acta Cryst., D50, (1994), pp. 484-490.
Garcia-Ruiz, J.M. et al., "Investigation on protein crystal growth by the gel acupuncture method," Acta. Cryst,, 1994, vol. D50, pp. 484-490.
Garcia-Ruiz, Juan Ma. et al., "A supersaturation wave of protein crystallization", J. Crystal Growth, 2001, vol. 232, pp. 149-155.
Garthright, Wallace E. et al., "Confidence Intervals for Microbial Density Using Serial Dilutions with MPN Estimates,"Biom. J., vol. 38, No. 4, (1996), pp. 489-505.
Gascoyne, Peter R.C. et al., "Isolation of Rare Cells From Cell Mixtures by Dielectrophoresis," Electrophoresis, vol. 30, (2009), pp. 1388-1398.
Geletii, Yu V. et al., "Catalytic-Oxidation of alkanes by Molecular Oxidation," Oxidation of Methane in the Presence of Platinum Salts and Heteropoly Acids, Kinet. Catal., vol. 24, No. 2, (1983), pp. 413-416.
Gerdts, Cory J. et al., "A Synthetic Reaction Network: Chemical Amplification Using Nonequilibrium Autocatalytic Reactions Coupled in Time," J. Am. Chem. Soc., vol. 126, (2004), pp. 6327-6331.
Gerdts, Cory J. et al., "The Plug-Based Nanovolume Microcapillary Protein Crystallization System (MPCS),"vol. D64 (2008), pp. 1116-1122.
Gerdts, Cory J. et al., "Time-Controlled Microfluidic Seeding in nL-Volume Droplets to Separate Nucleation and Growth Stages of Protein Crystallization," vol. 45, (2006), pp. 81568160.
Goldman, Ellen R. et al., "Luminescent Quantum Dots Immunoassays," Anal Bioanal Chem., vol. 384 (2006), pp. 560-563.
Goodall, Jennifer L. et al., "Operation of Mixed-Culture Immobilized Cell Reactors for the Metabolism of Meta- and- Para-Nitrobenzoate by Comamonas Sp. JS46 and Comamonas Sp. J547," 1998, John Wiley & Sons, Inc., pp. 21-27.
Gorris, Hans H. et al., "Mechanistic Aspects of Horseradish Peroxidase Elucidated through Single-Molecule Studies" J. Am. Chem. Soc. vol. 131, (2009), pp. 6277-6282.
Gorris, Hans H. et al., "Stochastic Inhibitor Release and Binding from Single-Enzyme Molecules," PNAS, vol. 104, No. 45, (2007), pp. 17680-17685.
Gratton, Stephanie E.A. et al., "Nanofabricated Particles for Engineered Drug Therapies: A Preliminary Biodistribution Study of PRINT Nanoparticles,"ScienceDirect Journal of Controlled Release, vol. 121 (2007), pp. 10-18.
Greengrass, Vicki et al., "Assessment of the Low-Cost Cavidi ExaVir Load Assay for Monitoring HIV Viral Load in Pediatric and Adult Patients,"Acquir Immune Defic Syndr, vol. 52, No. 3, (2009), pp. 387-390.
Griffiths, Andrew D. et al., "Man-Made Enzymes—From Design to In Vitro Compartmentalisation,"Curr. Opin. Biotechnol., vol. 11, (2000), pp. 338-353.
Gu, Hao, et al., "Droplets Formation and Merging in Two-Phase Flow Microfluidics", Int. J. Mol. Sci., 2011, vol. 12, pp. 2572-2597.
Guillemette, Maxime D. et al., "Surface Topography Induces 3D Self-Orientation of Cells and Extracellular Matrix Resulting in Improved Tissue Function," Integr. Biol., vol. 1, (2009), pp. 196-204.
Gulliksen, Anja, et al., "Parallel Nanoliter Detection of Cancer Markers Using Polymer Microchips," Lab Chip, vol. 5, (2005), pp. 416-420.
Gunther, Axel et al., "Multiphase Microfluidics: From Flow Characteristics to Chemical and Materials Synthesis,"Lab Chip, vol. 6, (2006), pp. 1487-1503.
Gunther, Axel et al., "Transport and Reaction in Microscale Segmented Gas-Liquid Flow,", Lab Chip, vol. 4, (2004), pp. 278-286.

Hallen, Magnus et al., "A Comparison of Two Different Assays for Determining S-1008 in Serum and Urine," Clinical Chemistry and Laboratory Medicine, vol. 47, pp. 1025-1029.
Halsey, Thomas C. et al., "The Rotary Electrorheological Effect," International Journal of Modern Physics B, vol. 10, No. 23-24, pp. 3019-3027.
Hansen, Carl et al., "Microfluidics in Structural Biology: Smaller, Faster . . . Better,"Curr. Opin. Struct. Biol., vol. 13, (2003), pp. 538-544.
Hansen, Carl L. et al., "A Robust and Scalable Microfluidic Metering Method that allows Protein Crystal Growth by Free Interface Diffusion," Proc. Natl. Acad. Sci. U. S. A., vol. 99, No. 26 (2002), pp. 16531-16536.
Hansen, Carl L., et al., "A Microfluidic Device for Kinetic Optimization of Protein Crystallization and In Situ Structure Determination,"J. Am. Chem. Soc., vol. 128, (2006), pp. 3142-3143.
Hatakeyama, Takuji et al., "Microgram-Scale Testing of Reaction Conditions in Solution Using Nanoliter Plugs in Microfluidics with Detection by MalDI-MS," Journal of the American Chemical Society, vol. 128, No. 8, (2006), pp. 2518-2519.
Hathcock, James J. et al., "Flow Effects on Coagulation and Thrombosis,"Arterioscler. Thromb. Vasc. Biol., vol. 27, (2007), pp. 1729-1737.
Haudek, Verena J. et al, "Proteome Maps of the Main Human Peripheral Blood Constituents,"J Proteome Res, vol. 8, No. 8, (2009), pp. 3834-3843.
Hay Burgess, Deborah C. et al., "Global Health Diagnostics,"Nature Publishing Group, vol. 444, Suppl. 1, (2006), pp. 1-2.
Hayes, Ronald L. et al. Proteomic Identification of Biomarkers of Traumatic Brain Injury Expert Review of Proteomics, vol. 2, No. 4, (2005), pp. 603-614.
He, Mingyan et al. "Selective encapsulation of single cells and subcellular organelles into picoliter- and femtoliter-volume droplets," Analytical Chemistry, 2005, vol. 77, No. 6, pp. 15391544.
He, Wei et al., "In Vivo Quantitation of Rare Circulating Tumor Cells by Multiphoton Intravital Flow Cytometry," Proceedings of the National Academy of Sciences of the United States of America, vol. 104, (2007), pp. 11760-11765.
He, Xinya et al., "Microfluidic Protein patterning on Silicon Mitride Using Solvent-Extracted Poly(Dimethylsiloxane) Channels,"Sensors and Actuators B Chem., vol. 129, No. 2, (2008), pp. 811-817.
Hefner, G.J. et al., "Isothermal Amplification and Multimerization of DNA by Bst DNA Polymerase,"Biotechniques, vol. 30, No. 4 (2001), pp. 852-856.
Hellweg, Stephanie et al., "Physiotherapy After Traumatic Brain Injury: A Systematic Review of the Literature,"Brain Injury, vol. 22, No. 5, (2008), pp. 365-373.
Hellyer, Tobin J. et al., "Strand Displacement Amplification: A Versatile Tool for Molecular Diagnostics," Expert Rev Mol Diagn., vol. 4, (2004), pp. 251-261.
Herrmann, Marc et al., "Quantification of Low-Picomolar Concentrations of TNF-a in Serum Using the Dual-Network Microfluidic ELISA Platform,Anal. Chem., vol. 80, (2008), pp. 51605167.
Hill, Craig L. "Progress and Challenges in Polyoxometalate-Based Catalysis and Catalytic Materials Chemistry,"J. Mol. Catal., vol. 262, (2007), pp. 2-6.
Hillemann, Doris et al., "Use of the Genotype MTBDR Assay for Rapid Detection of Rifampin and Isoniazid Resistance in *Mycobacterium tuberculosis* Complex Isolates" Journal of Clinical Microbiology vol. 43, pp. 3699-3703.
Hirano, Shoji, et al., "Cluster Analysis of Long Time-Series Medical Datasets,"Data Mining and Knowledge Discovery: Theory, tools, and Technology VI, Proceedings of SPIE vol. 5433, No. 2, (2004), pp. 13-20.
Hirst, Evan R. et al., "Bond-Rupture Immunosensors—A Review" Biosensors & Bioelectronics, vol. 23, pp. 1759-1768.
Hlushkou, Dzmitry et al., "The Influence of Membrane Ion-Permselectivity on Electrokinetic Concentration Enrichment in Membrane-Based Preconcentration Units," Lab Chip, vol. 8, (2008), pp. 1153-1162.
Holtze, C. et al., "Biocompatible Surfactants for Water-in-fluorocarbon Emulsions," vol. 8, (2008), pp. 1632-1639.

(56) References Cited

OTHER PUBLICATIONS

Honda, Masahiro et al., "Serum Glial Fibrillary Acidic Protein Is a Highly Specific Biomarker for Traumatic Brain Injury in Humans Compared With S-100B and Neuron-Specific Enolase" Journal of Trauma, Injury, Infection and Critical Care, vol. 69, No. 1 (2010), pp. 104-109.
Hosaka, Norimitsu et al., "Rapid Detection of Human Immunodeficiency Virus Type 1 Group M by a Reverse Transcription-Loop-Mediated Isothermal Amplification Assay,"J. Virol. Methods, vol. 157, (2009), pp. 195-199.
Hourfar, Michael K. et al., "High-Throughput Purification of Viral RNA Based on Novel Aqueous Chemistry for Nucleic Acid Isolation," Clin. Chem., vol. 51, No. 7 (2005), pp. 12171222.
Hovda, D.A. et al., The Neurochemical and Metabolic Cascade Following Brain Injury—Moving from Animal-Models to Man. Journal of Neurotrauma, vol. 12, No. 5, (1995) pp. 903906.
Hsieh,H. Ben et al., "High Speed Detection of Circulating Tumor Cells," Biosensors & Bioelectronics vol. 21, (2007), pp. 1893-1899.
Hu, Guoqing et al., "A Microfluidic Chip for Heterogeneous Immunoassay Using Electrokinetical Control,"Microfluid. Nanofluid, vol. 1, (2005), pp. 347-355.
Hu, Li-Hong et al., "Synthesis and Biological Activity of Amide Derivatives of Ginkolide A," Journal of Asian Natural Products Research, University of Chicago, vol. 3, (2012), pp. 219227.
Huang, Bo et al., "Counting Low-Copy Number Proteins in a Single Cell," Science, vol. 315, No. 5808, (2007), pp. 81-84.
Huang, Jing et al., "A Yeast Genetic System for Selecting Small Molecule Inhibitors of Protein-Protein Interactions in Nanodroplets,"Proc. Natl. Acad. Sci., vol. 94, (1997), pp. 13396-13401.
Huebner, A. et al., "Quantitative detection of protein expression in single cells using droplet microfluidics," Chemical Communications, 2007, pp. 1218-1220.
Huebner, A. et al., "Static Microdroplet Arrays: A Microfluidic Device for Droplet Trapping, Incubation and Release for Enzymatic and Cell-Based Assays," Lab on a Chip, vol. 9, (2009) pp. 692-698.
Hughes, Michael D. et al., "Monitoring Plasma HIV-1 RNA Levels in Addition to CD4(+) Lymphocyte Count Improves Assessment of Antiretroviral Therapeutic Response," Annals of Internal Medicine, vol. 126, No. 12 (1997), pp. 929-938.
Hui, Elliot E. et al., "Micromechanical Control of Cell-Cell Interactions," Proceedings of the National Academy of Sciences of the United States of America, vol. 104, (2007), pp. 57225726.
Hurley, Margaret A. et al., "Automated Statistical Analysis of Microbial Enumeration by Dilution Series", J. Appl. Bacteriol, vol. 55, (1983), pp. 159-164.
Ichikawa, Naoki et al., "Interface Motion of Capillary-Driven Flow in Rectangular Microchannel," Journal of Colloid and Interface Science, vol. 280, (2004), pp. 155-164.
Ichimura, Kunihiro, "Molecular Amplification of Photochemical Events" Journal of Photochemistry and Photobiology A-Chemistry, vol. 158, (2003), pp. 205-214.
Inoue, Tomoya et al., "Microfabricated Multiphase Reactors for the Direct Synthesis of Hydrogen Peroxide from Hydrogen and Oxygen," Ind. Eng. Chem. Res., vol. 46, (2007), pp. 1153-1160.
Irimia, Daniel et al., "Spontaneous Migration of Cancer Cells Under Conditions of Mechanical Confinement" Integrative Biology, vol. 1, (2009), pp. 506-512.
Irish, Jonathan M. et al., "altered B-Cell Receptor Signaling Kinetics Distinguish Human Follicular Lymphoma B Cells From Tumor-Infiltrating Nonmalignant B Cells," Blood, vol. 108, (2006), pp. 3135-3142.
Irish, Jonathan M. et al., "Single Cell Profiling of Potentiated Phospho-Protein Networks in Cancer Cells," Cell, vol. 118, (2004), pp. 217-228.
Ito, Hiroshi et al., "Chemical Amplification in the Design of Dry Developing Resist Materials" Polymer Engineering and Science, vol. 23, pp. 1012-1018.
Ito, Hiroshi, "Chemical Amplification Resists for Microlithography," Adv. Polym. Sci, vol. 172, (2005), pp. 37-245.

Iverson, Grant L. et al., "Challenges Associated with Post-Deployment Screening for Mild Traumatic Brain Injury in Military Personnel," Clinical Neuropsychologist, vol. 23, No. 8, (2009), pp. 1299-1314.
Izutsu, Ken-ichi et al., "Freeze-Drying of Proteins in Glass Solids Formed by Basic Amino Acids and Dicarboxylic Acids," Chemical & Pharmaceutical Bulletin, vol. 57, (2009), pp. 4348.
Jahnisch, Klaus et al., "Chemistry in Mlcrostructured Reactors,"Angew. Chem. Int. Ed. vol. 43, (2004), pp. 406-446.
Jain, K.K., "Neuroprotection in Traumatic Brain Injury,"Drug Discovery Today, vol. 13 (2324): (2008), pp. 1082-1089.
Jeffreys, alec J. et al., "Repeat Unit Sequence Variation in Minisatellites: A Novel Source of DNA Polymorphism for Studying Variation and Mutation by Single Molecule Analysis" Cell, vol. 60, (1990), pp. 473-485.
Jennings, Cheryl et al., "Comparison of Two Human Immunodeficiency Virus (HIV) RNA Surrogate Assays to the Standard HIV RNA Assay," Journal of Clinical Microbiology, vol. 43, No. 12, (2005), pp. 5950-5956.
Jeon, Noo Li et al., "Generation of Solution and Surface Gradients Using Microfluidic Systems," Langmuir, Vo. 16, (2000), pp. 8311-8316.
Jeon, Noo Li et al., "Neutrophil Chemotaxis in Linear and Complex Gradients of Interleukin-8 Formed in a Microfabricated Device,"Nature Biotechnology, vol. 20, (2002), pp. 826-830.
Jeong, Yong-Joo et al., "Isothermal DNA Amplification in Vitro: The Helicase-Dependent Amplification System", Cell Mol Life Sci., vol. 66, (2009), pp. 3325-3336.
Johnson, David et al., "Biochemical Parameters of Recovery in Acute Severe Head-Injury," British Journal of Neurosurgery, vol. 7, No. 1, (1993), pp. 53-59.
Jones, C.J. et al., "Selective Oxidation of Methane to Methanol Catalyzed, with C—H Activation, by Homogeneous, Cationic Gold,"Angew. Chem. Int. Ed., vol. 43, (2004), pp. 4626-4629.
Jones, P.A. et al., "Graphical Display of Variability and Inter-Relationships of Pressure Signals in Children with Traumatic Brain Injury,"Physiological Measurement, vol. 24, No. 1, (2003) pp. 201-211.
Kaigala, Govind V., "Automated Screening Using Microfluidic Chip-Based PCR and Product Detection to Assess Risk of BK Virus Associated Nephropathy in Renal Transplant Recipients" Electrophoresis (2006), vol. 27, pp. 3753-3763.
Kalinina, Olga, et al., "Nanoliter Scale PCR with TaqMan Detection," Nucleic Acids Research, vol. 25, No. 10, (1997), pp. 1999-2004.
Kanatzidis, Mercouri G. "Beyond Silica: Nonoxidic Mesostructured Materials," Adv. Mater. vol. 19, (2007), pp. 1165-1181.
Kartalov, Emil P. et al., "High-Throughput Multi-Antigen Microfluidic Fluorescence Immunoassays,"BioTechniques, vol. 49, No. 1, (2006), pp. 85-90.
Keats, Jonathon et al., "Jargon Watch: Valedictocracy, ISS Toolbag, Chemstrode,"Wired Magazine 17.03, Feb. 23, 2009.
Kemp, David J. et al., "Colorimetric Detection of Specific DNA Segments Amplified by Polymerase Chain Reactions,"Proc. Natl. Acad. Sci., vol. 86, (1989), pp. 2423-2427.
Kennedy, Robert T et al., "In Vivo Monitoring of Amino Acids by Direct Sampling of Brain Extracellular Fluid at Ultralow Flow Rates and Capillary Electrophoresis," Journal of Neuroscience Methods, vol. 114, (2002), pp. 39-49.
Keymer, Juan E. et al., "Bacterial Metapopulations in Nanofabricated Landscapes," PNAS, vol. 103, No. 46, (2006), pp. 17290-17295.
Kim, Byoung Chan et al., "Quantitative Detection of HIV-1 Particles Using HIV-1 Neutralizing Anti body-Conjugated Beads,"Anal Chem., vol. 81, No. 6 (2009), pp. 2388-2393.
Kim, Choong et al., "A Serial Dilution Microfluidic Device Using a Ladder Network Generating Logarithmic or Linear Concentrations," Lab Chip, vol. 8, (2008), pp. 473-479.
Kim, Hyun Jung et al., "Defined Spatial Structure Stabilizes a Synthetic Multispecies Bacteria Community," PNAS, vol. 105, No. 47, (2008), pp. 18188-18193.

(56) References Cited

OTHER PUBLICATIONS

Kim, Sung Jae et al., "Concentration Polarization and Nonlinear Electrokinetic Flow Near a Nanofluidic Channel,"Physical Review Letters, vol. 99, (2007) pp. 044501.

Kim, Sung Jae et al., "Self-Sealed Vertical Polymeric Nanoporous-Junctions for High-Throughput Nanofluidic App/ications," Analytical Chemistry, vol. 80, No. 9, (2008), pp. 35073511.

Kimura, et al., "Inference of S-System Models of Genetic Networks Using a Cooperative Coevolutionary algorithm," Bioinformatics, vol. 21, No. 7, (2005), pp. 1154-1163.

Kinzelman, Julie L. et al., "Use of IDEXX Colilert-18 and Quanti-Tray/2000 as a Rapid and Simple Enumeration Method for the Implementation of Recreational Water Monitoring and Notification Programs," Lake and Reserv. Manag., vol. 21, No. 1 (2005), pp. 73-77.

Kline, et al., "D Blood Typing and Subtyping Using Plug-Based Microfluidics," Analytical Chemistry, vol. 80, No. 16, (2008), pp. 6190-6197.

Kobayashi, Juta et al., "A Microfluidic Device for Conducting Gas-Liquid-Solid Hydrogenat Reactions,"Science, vol. 304, (2004), pp. 1305-1308.

Kobayashi, Juta, et al., "Multiphase Organic Synthesis in Microchannel Reactors," Chem. Asian J. , vol. 1, (2006), pp. 22-35.

Kobeissy, Firas H. et al. "Psychoproteomic Analysis of Rat Cortex Following Acute Methamphetamine Exposure,"Journal of Proteome Research, vol. 7, No. 5, (2008), pp. 1971-1983.

Kobeissy, Firas H. et al., "Novel Differential Neuroproteomics Analysis of Traumatic Brain Injury in Rats" Molecular & Cellular Proteomics, vol. 5, (2005), pp. 1887-1898.

Koh, Chee G. et al., "Integrating Polymerase chain Reaction, Valving, and Electrophoresi.! a Plastic Device for Bacterial Detection", Anal. Chem., vol. 75, (2003), pp. 4591-4598.

Kontos, Hermes A. et al., "Oxygen Radicals in Cerebral Vascular Injury,"Circulation Research,vol. 57, No. 4, (1985), pp. 508-516.

Koster, Sarah et al., Influence of Internal Capsid Pressure on Viral Infection by Phage Lambda. Biophysical Journal, vol. 97, No. 6, (2009), pp. 1525-1529.

Kottegoda, Sumith et al., "Demonstration of Low Flow Push-Pull Perfusion,"Journal of Neuroscience Methods, vol. 121, No. 1, (2002), pp. 93-101.

Koumura, A. et al., "A Novel Calpain Inhibitor, ((15)-4(((I s)-1-Benzyl-3-Cyclopropylamina 2,3-Di-Oxopropyl)Amino)Carbonyl)-3-Methylbutyl) Carbamic Acid 5-Methoxy-3-Oxapentyl Ester, Protects Neuronal Cells from Cerebral Ischemia-Induced Damage in Mice," Neuroscience, vol. 157, No. 2, (2008), pp. 309-318.

Kraeft, Stine-Kathrein et al., "Reliable and Sensitive Identification of Occult Tumor Cells U the Improved Rare Event Imaging System" Clinical Cancer Research, vol. 10, (2004), pp. 3020-3028.

Kralj, Jason G. et al., "Integrated Continuous Microfluidic Liquid-Liquid Extraction," Lab C vol. 7, No. 2, (2007), pp. 256-263.

Kreutz, James E. et al., "Laterally Mobile, Functionalized Self-Assembled Monolayers at tl Fluorous—Aqueous Interface in a Plug-Based Microfluidic System: Characterization and Testing with Membrane Protein Ctystallization,"J. Am. Chem. Soc., vol. 131, (2009), pp. 6042-6043.

Kreutz, Jason E. et al., "Evolution of Catalysts Directed by Genetic algorithms in a Plug-Based Microfluidi Device Tested with Oxidation of Methane by Oxygen,"J. Am Chem Soc vol. 132, No. 9, (2010), pp. 3128-3132.

Krivacic, Robert T. et al., "A Rare-Cell Detector for Cancer" PNAS, vol. 101, No. 29, (200 pp. 10501-10504.

Krstenansky, John L. et al., "Biocatalytic Combinatorial Synthesis," Bioorganic & Medicine Chemistry, vol. 7, No. 10, pp. 2157-2162.

Krutzik, Peter 0. et al., "High-Content single-Cell Drug Screening with Phosphospecific Fl Cytometry,"Nat. Chem. Biol., vol. 4, No. 2 (2008), pp. 132-142.

Kulakovich, Olga et al., Enhanced Luminescence of CdSe Quantum Dots on Gold Colloid Nano Letters, vol. 2, pp. 1449-1452.

Kumar,Vineet et al., "In Situ Precipitation and Vacuum Drying of Interferon alpha-2a: Development of a Single-Step Process for Obtaining Dry, Stable Protein Formulation," International Journal of Pharmaceutics, vol. 366, (2009), pp. 88-98.

Labbett, Wendy et al., "Comparative Evaluation of the ExaVir Load Version 3 Reverse Transcriptase Assay for Measurement of Human Immunodeficiency Virus Type 1 Plasma Load,"J. Clin. Microbiol., vol. 47, No. 10, (2009), pp. 3266-3270.

Labinger, Jay A. et al., "Understanding and Exploiting c—H Bond Activation,"Nature, vol. 417, (2002), pp. 507-514.

Lacharme, F. et al., "Magnetic Beads Retention Device for Sandwich Immunoassay: Comparison of Off-Chip and On-Chip Antibody Incubation,"Microfluid. Nanofluid, vol. 7, (2009), pp. 479-487.

Lai,Siyi et al., Design of a Compact Disk-Like Microfluidic Platform for Enzyme-Linked Immunosorbent Assay, Anal. Chem., vol. 76, No. 7, (2004), pp. 1832-1837.

Lam, Kit s. et al., "The One-Bead-One-Compound Combinatorial Library Method,"Chem. Rev., vol. 97, (1997), pp. 411-448.

Lapizco-Encinas, Blanca H. et al., "An Insulator-Based (Electrodeless) Dielectrophoretic Concentrator for Microbes in Water", Journal of Microbiological Methods, vol. 62, (2005) pp. 317-326.

Lau, Billy T.C. et al., "A Complete Microfluidic Screening Platform for Rational Protein Crystallization,"J. Am. Chem. Soc., vol. 129, (2007), pp. 454-455.

Laws, Derek R. et al., "Bipolar Electrode Focusing: Simultaneous Concentration Enrichment and Separation in a Microfluidic Channel Containing a Bipolar Electrode" Analytical Chemistry, vol. 81 (2009), pp. 8923-8929.

Leamon, John H. et al., "Overview: Methods and Applications for Droplet Compartmentalization of Biology," Nature Methods, vol. 3, (2006), pp. 541-543.

Leardi, Riccardo et al., "Genetic algorithms in Chemistry," J. Chromatogr. A, vol. 1158, (2007), pp. 226-233.

Leclerc, E. et al., "Study of Osteoblastic Cells in a Microfluidic Environment Biomaterials,"vol. 27, (2007), pp. 586-595.

Lee, Jeong Yong et al., Metal-Organic Framework Materials as Catalysts, Soc. Rev., vol. 38, (2009), pp. 1450-1459.

Lersch, Martin et al., "Mechanistic Aspects of C—H Activation by Pt. Complexes," Chem. Rev., vol. 105, (2005), pp. 2471-2526.

Li et al., "A Plug-Based Microfluidic System for Dispensing Lipidic Cubic Phase (LCP) Material Validated by Crystallizing Membrane Proteins in Lipidic Mesophases,"Microfluid Nanofluid , vol. 8, (2010), pp. 789-798.

Li et al., "Nanoliter Microfluidic Hybrid Method for Simultaneous Screening and Optimization Validated with Crystallization of Membrane Proteins," PNAS vol. 103, No. 51, (2006), pp. 19243-19248.

Li et al., "Simple Host-Guest Chemistry to Modulate the Process of Concentration and Crystallization of Membrane Proteins by Detergent Capture in a Microfluidic Device," J. Am. Chem. Soc., vol. 130, 2008, pp. 14324-14328.

Li, Xu et al., "Paper-Based Microfluidic Devices by Plasma Treatment"Analytical Chemistry, vol. 80, (2008), pp. 9131-9134.

Li, Zhaohui, et al., "Detection of Single-Molecule DNA Hybridization using Enzymatic Amplification in an Array of Femtoliter-Sized Reaction Vessels," J. Am. Chem. Soc., vol. 130, (2008), pp. 12622-12623.

Liang, Ru-Qiang, et al., "Colorimetric Detection of Protein Microarrays Based on Nanogold Probe Coupled with Silver Enhancement" Journal of Immunological Methods, vol. 285, (2004), pp. 157-163.

Liao, Warren T., "Clustering of Time Series Data—A Survey." Pattern Recognition, vol. 38, No. 11, (2005), pp. 1857-1874.

Lim, C.T. et al., "Bead-Based Microfluidic Immunoassays: The Next Generation," Biosens. Bioelectron, vol. 22, (2007), pp. 1197-1204.

Lin, Jessica et al., "A Symbolic Representation of Time Series, with Implications for Streaming algorithms," DMKD, (2003), San Diego, CA.

Lin, Minren et al., "Direct Catalytic Conversion of Methane to Acetic Acid in an Aqueous Medium," Letters to Nature, vol. 368, (1994), pp. 613-615.

Linder, Vincent et al., "Application of Surface biopassivated Disposable Poly(Dimethylsiloxane)/Glass Chips to a Heterogeneous

(56) References Cited

OTHER PUBLICATIONS

Competitive human Serum Immunoglobulin G Immunoassay with Incorporated Internal Standard," Electrophoresis, vol. 23, (2002), pp. 740-749.

Linder, Vincent et al., "Reagent-Loaded Cartridges for Valveless and Automated Fluid Delivery in Microfluidic Devices," Anal. Chem.vol. 77, No. 1, (2005), pp. 64-71.

Lisi, T.L. et al., "Comparison of Microdialysis and Push-Pull Perfusion for Retrieval of Serotonin and Norepinephrine in the Spinal Cord Dorsal Horn,"Journal of Neuroscience Methods, vol. 126, No. 2, (2003) pp. 187-194.

Liu, Jian et al., "A Nanoliter Rotary Device for Polymerase Chain Reaction," Electrophoresis, vol. 23, (2002), pp. 1531-1536.

Liu, Ming Chen, et al.,"Extensive Degradation of Myelin Basic Protein Isoforms by Calpain Following Tramatic Brain Injury,"Journal of Neurochemistry, vol. 98, (2006), pp. 700-712.

Liu, Ming Cheng et al., "Comparing Calpain- and Caspase-3-Mediated Degradation Patterns in Traumatic Brain Injury by Differential Proteome Analysis," Biochemical Journal vol. 394, (2006) pp. 715-725.

Liu, Ming Cheng et al., "Ubiquitin C-Terminal Hydrolase-L1 as a Biomarker for Ischemic and Traumatic Brain Injury in Rats,"European Journal of Neuroscience, vol. 31, No. 4, (2010), pp. 722-732.

Liu, Weishan, et al., "Isolation, Incubation, and Parallel Functional Testing and Identification by FISH of Rare Microbial Single-Copy Cells from Multi-Species Mixtures Using the Combination of Chemistrode and Stochastic Confinement," Lab Chip, vol. 9, No. 15, (2009), pp. 2153-2162.

Liu, Ying et al., "Dynamics of Coalescence of Plugs with a Hydrophilic Wetting Layer Induced by Flow in a Microfluidic Chemistrode". Langmuir, vol. 25, No. 5, (2009), pp. 2854-2859.

Lo, Tsz-Yan M. et al., "Pediatric Brain Trauma Outcome Prediction Using Paired Serum Levels of Inflammatory Mediators and Brain-Specific Proteins" Journal of Neurotrauma, vol. 26, pp. 1479-1487.

Locascio, Joseph J. et al., "Time Series Analysis in the Time Domain and Resampling Methods for Studies of Functional Magnetic Resonance Brain Imaging," Human Brain Mapping, vol. 5, No. 3, (1997), pp. 168-193.

Long, De-Liang, et al., "Towards Polyoxometalate-Integrated Nanosystems," Chem.-Eur. J. vol. 12, (2006), pp. 3699-3706.

Love, J. Christopher, et al., A Microengraving Method for Rapid Selection of Single Cells Producing Antigen-Specific Antibodies, Nature Biotechnol., vol. 24, No. 6, (2006), pp. 703707.

Loyer, Milton W., et al., "Interval Estimation of the Density of Organisms Using a Serial-Dilution Experiment,"Biometrics, vol. 40, No. 4, (1984) pp. 907-916.

Lu, Miao-Jen et al., "Detection of Elevated Signaling Amino Acids in Human Diabetic Vitreous by Rapid Capillary Electrophoresis," Experimental Diabetes Research, vol. 2007, Article ID 39765, 6p.

Lun, Fiona M.F. et al., "Microfluidics Digital PCR Reveals a Higher Than Expected Fraction of Fetal DNA in Maternal Plasma,"vol. 54, (2008), pp. 1664-1672.

MacDougall, David S. et al., "Quantitative Measurement of HIV RNA Techniques Clinical Applications,"J. of Intl Assoc. of Physicians in AIDS Care, vol. 2, No. 11 (1996), pp. 9-14.

Macek, K., and Beavafova, H., "*Papers, Ready-For-Use Plates and Flexible Sheets for Chromatography, "Chromatographic* Reviews, vol. 15, No. 1, (1971), pp. 1-28.

Madou, Marc, et al., "Lab on a CD,"Annu. Rev. Biomed. Eng., vol. 8, (2006), pp. 601-628.

Maerkl, Sebastian J. et al., "A Systems Approach to Measuring the Binding Energy Landscapes of Transcription Factors" Science, vol. 315, (2007), pp. 233-237.

Maier, Wilhelm F, et al., "Combinatorial and High-Throughput Materials Science," S Angew. Chem.-Int. Edit., vol. 46, (2007), pp. 6016-6067.

Maiorella, Brian, et al., "Crossflow Microfiltration of Animal Cells,"Biotechnology and Bioengineering, vol. 37, (1991), pp. 121-126.

Majchrowicz, "Beyond Antiretroviral Access: Low-Cost Laboratory Tests Needed for the Developing World,"AIDS, vol. 17, Suppl 4, (2003), pp. S13-S15.

Makinen, Johanna, et al., Automated Purification of Borrelia Burgdorferi s.1. PCR Products with KingFisher Magnetic Particle Processor Prior to Genome Sequencing, J. Magnetism and Magnetic Materials, vol. 225, (2001), pp. 134-137.

Marcy, Yann, et al., "Nanoliter Reactors Improve Multiple Displacement Amplification of Genomes from Single Cells,"PLoS Genetics, vol. 3, No. 9, (2007), pp. 1702-1708.

Markoulatos, P., et al., "Multiplex Polymerase Chain Reaction: A practical Approach,"J. Clin. Lab. Anal., vol. 16, (2002), pp. 47-51.

Marriott, Gerard, "Time-Resolved Delayed Luminescence Image Microscopy Using an Europium Ion Chelate Complex,"Biophysical Journal, vol. 67, (1994), pp. 957-965.

Martin, Anandi, et al., "Resazurin Microtiter Assay Plate Testing of *Mycobacterium tuberculosis* Susceptibilities to Second-Line Drugs: Rapid, Simple, and Inexpensive Method," Antimicrobial Agents and Chemotherapy, vol. 47, No. 11, (2003), pp. 3616-3619.

Martin, James E. et al., "Strong Intrinsic Mixing in Vortex Magnetic Fields," Physical Review, vol. 80, (2009), pp. 016312.

Martin, James E., et al., "Simulation of the Athermal Coarsening of Composites Structured by a Uniaxial Field,"Journal of Chemical Physics vol. 108, No. 9, (1998), pp. 3765-3787.

Martinez, Andres et al., "FLASH: A Rapid Method for Prototyping Paper-Based Microfluidic Devices," Lab Chip, vol. 8, (2008), pp. 2146-2150.

Martinez, Andres W. et al., "Patterned Paper as a Platform for Inexpensive, Low-Volume, Portable Bioassays,"Angew. Chem. Int. Ed. vol. 46, (2007), pp. 318-1320.

Martinez, Andres W. et al., "Simple Telemedicine for Developing Regions: Camera Phones and Paper-Based Microfluidic Devices for Real-Time, Off-Site Diagnosis," Analytical Chemistry, vol. 80, No. 10, (2008), pp. 3699-3707.

Matsubara, Yasutaka et al., "Application of On-Chip Cell Cultures for the Detection of allergic Response". Biosensors & Bioelectronics, vol. 19, (2004), pp. 741-747.

Matsubara, Yasutaka et al., "Microchamber Array based DNA Quantification and Specific Sequence Detection from a Single Copy via PCR in Nanoliter Volumes,"Biosensors and Bioelectronics, vol. 20, (2005), pp. 1482-1490.

McCormack, Devin et al., "Photoacoustic Detection of Melanoma Micrometastasis in Sentinel Lymph Nodes". Journal of Biomechanical Engineering-Transactions of the Asme, vol. 131 ( 2009).

McDonald, J. Cooper, et al., "Poly(Dimethylsiloxane) as a Material for Fabricating Microfluidic Devices,"Accounts of Chem. Res., vol. 35, No. 7, (2002), pp. 491-499.

McPherson, A. et al., "Crystallization of Biological Macromolecules,"Cold Spring Harbor Laboratory Press, (1999).

Meier, Matthias et al., "Plug-Based Microfluidics with Defined Surface Chemistry to Miniaturize and Control Aggregation of Amyloidogenic Peptides,"Angewandte Chemie-International Edition, vol. 48, No. 8, (2009), pp. 1487-1489.

Melle, Sonia et al., "Chain Model of a Magnetorheological Suspension in a Rotating Field," Journal of Chemical Physics, vol. 118, No. 21, pp. 9875-9881.

Melle, Sonia et al., "Structure and Dynamics of Magnetorheological Fluids in Rotating Magnetic Fields," Physical Review E, vol. 61, vol. 4, pp. 4111-4117.

Mellors, John W. et al., "Prognosis in HIV-1 Infection Predicted by the Quantity of Virus in Plasma,"Science, New Series, vol. 272, No. 5265, (1996), pp. 1167-1170.

Meyvantsson, Ivar et al., "Cell Culture Models in Micro fluidic Systems". Annual Review of Analytical Chemistry 1, 423-449 (2008).

Michels, Peter C. et al., "Combinatorial Biocatalysis: A Natural Approach to Drug Discovery," Trends in Biotechnology, vol. 16, No. 5, pp. 210-215.

Miller, M. Craig et al., "Significance of Circulating Tumor Cells Detected by the CellSearch System in Patients with Metastatic Breast Colorectal and Prostate Cancer". Journal of Oncology 2010, Article ID 617421, 8 pages.

(56) References Cited

OTHER PUBLICATIONS

Miller, Oliver J., et al., "Directed Evolution by in Vitro Compartmentalization,"Nat. Methods, vol. 3, No. 7, (2006), pp. 561-570.

Mohamed, et al., "Isolation of Tumor Cells Using Size and Deformation," Journal of Chromatography, (2009) pp. 8289-8295.

Mohamed, Hisham et al. "Development of a Rare Cell Fractionation Device: Application for Cancer Detection," IEEE Transactions on Nanobioscience, vol. 3, No. 4 (2004), pp. 251-256.

Monckton, Darren G. et al., "Minisatellite" Isoallele "Discrimination in Pseudohomozygotes by Single Molecule PCR and Variant Repeat Mapping,"Genomics, vol. 11, (1991), pp. 465-467.

Moorthy, Jaisree et al., "In Situ Fabricated Porous Filters for Microsystems," Lab Chip, vol. 3, (2003), pp. 62-66.

Morales, D.M. et al., "Experimental Models of Traumatic Brain Injury: Do we really need to build a better mousetrap?"Neuroscience, vol. 136, No. 4, (2005), pp. 971-989.

Morris, L.D. et al., "Use of a New HemoCue System for Measuring Haemoglobin at Low Concentrations,"Clinical and Laboratory Haematology, vol. 23, No. 2, (2001), pp. 91-96.

Morton, Keith J. et al., "Hydrodynamic Metamaterials: Microfabricated Arrays to Steer, Refract, and Focus Streams of Biomaterials," Proceedings of the National Academy of Sciences of the United States of America, vol. 105, (2008), pp. 7434-7438.

Moser, Y. et al., On-Chip Immuno-Agglutination Assay with Analyte Capture by Dynamic Manipulation of Superparamagnetic Beads, Lab Chip, vol. 9, (2009), pp. 3261-3267.

Mountzouros, Kenneth T. et al., "Detection of Complement-Mediated Antibody-Dependent Bactericidal Activity in a Fluorescence-Based Serum Bactericidal Assay for Group B Neisseria Meningitidis,"J. Clin. Microbiol.,vol. 38, No. 8, (2000), pp. 2878-2884.

Murakami, Yoshihiro, et al., "On-Chip Micro-flow Plystyrene Bead-Based Immunoassay for Quantitative Detection of Tacrolimus(FK506),"Anal. Biochem., vol. 334, (2004), pp. 111-116.

Murshudov, Garib N. et al., "Refinement of Maromolecular Structures by the Maximum-Likelihood Method,"Acta Crystallographica Section D-Biological Crystallography, vol. 53, (1997), pp. 240-255.

Myers, R.D. et al., "Simultaneous Comparison of Cerebral Dialysis and Push—Pull Perfusion in the Brain of Rats: A Critical Review," Neuroscience and Biobehavioral Reviews, vol. 22, No. 3, (1998), pp. 371-387.

Nagrath, Sunitha et al., "Isolation of Rare Circulating Tumour Cells in Cancer Patients by Microchip Technology" Nature, vol. 450, (2007), pp. 1235-U10.

Nam,Jwa-Min et al., "Nanoparticle-Based Bio-Bar Codes for the Ultrasensitive Detection of Proteins" Science, vol. 301, pp. 1884-1886.

Neuman de Vegvar, Henry E., et al., "Microarray Profiling of Antiviral Antibodies for the Development of Diagnostics, Vaccines, and Therapeutics," Clin. Immunol., vol. 111, (2004), pp. 196-201.

Ng, Joseph D. et al., "In Situ X-ray Analysis of Protein Crystals in Low-Birefringent and X-ray Transmissive Plastic Microchannels," Acta Crystallogr. , vol. D64, (2008), pp. 189-197.

Ng, Joseph D. et al., "Protein crystallization by capillary counterdiffusion for applied crystallographic structure determination," Journal of Structural Biology, 2003, vol. 142, pp. 218-231.

Ng, Joseph D. et al., "Protein Crystallization by Capillary Counterdiffusion for Applied Crystallographic Structure Determination,"J. Struct. Biol., vol. 142, (2003), pp. 218-231.

Niemela, S.I. et al., "A Comparison of the International Standards Organisation Reference Method for the Detection of Coliforms and *Escherichia coli* in Water with a Defined Substrate Procedure," J. Appl. Microbiol., vol. 95, (2003), pp. 1285-1292.

Niemeyer, Christof M. et al., "Immuno-PCR: High Sensitivity Detection of Proteins by Nucleic Acid Amplification" Trends in Biotechnology, vol. 23, No. 4, (2006), pp. 208-216.

Nisisako, Takasi et al., "Formation of Droplets Using Branch Channels in a Microfluidic Circuit," SICE, Aug. 2002, pp. 1262-1264.

Nisisako, Takasi et al., "Synthesis of Monodisperse Bicolored Janus Particles with Electrical Anisotropy Using a Microfluidic Co-Flow System,"Advanced Materials, vol. 18, (2006), pp. 1152-1156.

Nosworthy, Neil J. et al., "A New Surface for Immobilizing and Maintaining the Function of Enzymes in a Freeze-Dried State," Biomacromolecules, vol. 10, (2009), pp. 2577-2583.

O'Brien, J. et al., "Investigation of the alamar Blue (Resazurin) Fluorescent dye for the Assessment of Mammalian Cell Cytotoxicity," Molecular Toxicology, vol. 164, (2001), pp. 132-132.

Oehler, V.G. et al., "Absolute Quantitative Detection of ABL Tyrosine Kinase Domain Point Mutations in Chronic Myeloid Leukemia Using a Novel Nanofluidic Platform and Mutation-Specific PCR,"vol. 23, (2009), pp. 396-399.

Office action dated Feb. 28, 2014 for U.S. Appl. No. 13/257,811.

Office action dated Dec. 18, 2013 for U.S. Appl. No. 13/440,371.

Ohji, Hiroshi, et al., "Macro Porous Silicon Formation for Micromachining,"Micromachining and Microfabrication Process Technology III, SPIE vol. 3223, No. 189, (1997), pp. 29-30.

Ohrenberg, Arne et al., Application of Data Mining and Evolutionary Optimization in Catalyst Discoery and High-Throughput Experimentation—Techniques, Strategies, and Software, QSAR Comb. Sci., vol. 24, (2005), pp. 29-37.

Okie, Susan et al., "Traumatic Brain Injury in the War Zone" The New England Journal of Medicine, vol. 352, No. 20, (2005) pp. 2043-2047.

Olson, Eric N., "The Microarray Data Analysis Process: From Raw Data to Biological Significance,"The Am. Soc. For Experimental NeuroTherapeutics, vol. 3, (2006), pp. 373-383.

Onal, Yucel et al., "Application of a Capillary Microreactor for Selective Hydrogenation of a,f3-Unsaturated aldehydes in Aqueous Multiphase Catalysis,"Chem. Eng. Technol., vol. 28, No. 9, (2005), pp. 972-978.

O'Neill, Roger A. et al., "Isoelectric Focusing Technology Quantifies Protein Signaling in 25 Cells," Proceedings of the National Academy of Sciences of the United States of America, vol. 103, (2006), pp. 16153-16158.

Ong, Siew-Min et al., "A Gel-Free 3D Microfluidic Cell Culture System" Biomaterials, vol. 29, (2008), pp. 3237-3244.

Ottens, Andrew K. et al., "Neuroproteomics in Neurotrauma,"Mass Spectrometry Reviews, vol. 25, (2006), pp. 380-408.

Ottens, Andrew K. et al., "Novel Neuroproteomic Approaches to Studying Traumatic Brain Injury Neurotrauma," Progress in Brain Research, vol. 161, (2007), pp. 401-418.

Otwinowski, Zbyszek et al., "Processing of X-Ray Diffraction Data Collected in Oscillation Mode,"Methods in Enzymology, vol. 276, (1997), pp. 307-326.

Paegel, Brian M. et al., "Microfluidic Serial Dilution Circuit"Analytical Chemistry, vol. 78, (2006), pp. 7522-7527.

Pai, Nittika Pant et al., "Evaluation of Diagnostic Accuracy, feasibility and Client Preference for Rapid Oral Fluid-Based Diagnosis of HIV Infection in Rural India," PLoS ONE, Issue 4, (2007), pp. e367.

Pan, Chu-Hsiang et al., "A Visual DNA Chip for Simultaneous Detection, Genotyping and Differentiation of Wild-type and Vaccine-Type Classical Swine Fever Virus" Taiwan Veterinary Journal, No. 34, No. 2 (2008), pp. 66-76.

Papa, Linda et al., "Ubiquitin C-Terminal Hydrolase is a Novel Biomarker in Humans for Severe Traumatic Brain Injury," Critical Care Medicine, vol. 38, No. 1 (2010), pp. 138-144.

Parekkadan, Biju et al., "Cell-Cell Interaction Modulates Neuroectodermal Specification of Embryonic Stem Cells" Neuroscience Letters, vol. 438, (2008), pp. 190-195.

Paris, Pamela L. et al., "Functional Phenotyping and Genotyping of Circulating Tumor Cells from Patients with Castration Resistant Prostate Cancer" Cancer Letters, vol. 277, (2009), pp. 164-173.

Park, Jungwook et al., "A Calcium Ion-Selective Electrode Array for Monitoring the Activity of HepG2/C3As in a Microchannel," Sensors and Actuators B, vol. 174, (2012), pp. 473-477.

(56) References Cited

OTHER PUBLICATIONS

Park, Sungsu et al., "Influence of Topology on Bacterial Social Interaction" Proceedings of the National Academy of Sciences of the United States of America, vol. 100, (2003), pp. 13910-13915.
Periana, Roy A. et al., "Platinum Catalysts for the High-Yield Oxidation of Methane to a Methanol Derivative,"Science, vol. 280, No. 5363, (1998), pp. 560-564.
Perry, John J. et al., "Design and Synthesis of Metal-Organic Frameworks Using Metal-Organic Polyhedra as Supermolecular Blocks," Chem. Soc. Rev., vol. 38, (2009), pp. 14001417.
Persidis, Aris et al., "High-Throughput Screening," Nat. Biotechnol., vol. 16 (1998), pp. 488489.
Petronis, Sarunas et al., "Model Porous Surfaces for Systematic Studies of Material-Cell Interactions,"Journal of Biomedical Materials Research—Part A,, vol. 66 (3), (2003), pp. 707-721.
Phan, Sieu et al., "A Novel Pattern Based Clustering Methodology for Time-Series Microarray Data," International Journal of Computer Mathematics, vol. 84, No. 5, (2007), pp. 585-597.
Pichonat, Tristan et al., "Development of Porous Silicon-Based Miniature Fuel Cells," Journal of Micromechanics and Microengineering, vol. 15, (2005), pp. 5179-5184.
Pihl, Johan et al., "Microfluidics for Cell-Based Assays,"Materials Today, vol. 8, No. 12, (2005), pp. 46-51.
Pikal, Michael J. et al., "Solid State Chemistry of Proteins: II. The Correlation of Storage Stability of Freeze-Dried Human Growth Hormone (hGH) with Structure and Dynamics in the Glassy Solid,"Journal of Pharmaceutical Sciences, vol. 97, No. 12 (2008), pp. 5106-5121.
Pike, Brian R. et al., "Regional Calpain and Caspase-3 Proteolysis of alpha-Spectrin After Traumatic Brain Injury,"Neuroreport, vol. 9, No. 11, (1998), pp. 2437-2442.
Pineda, Jose A. et al., "Clinical Significance of all-Spectrin Breakdown Products in Cerebrospinal Fluid After Severe Traumatic Brain Injury" Journal of Neurotrauma, vol. 24, No. 1 (2007), pp. 354-366.
Pipper, Juergen et al., "Catching Bird Flu in a Droplet,"Nature Medicine, vol. 13, No. 10, (2007), pp. 1259-1263.
Plotkin, Steven S. "Generalization of Distance to Higher Dimensional Objects," Proceedings of the National Academy of Sciences of the United States of America, vol. 104, No. 38, (2007), pp. 14899-14904.
Pollack, M.G. et al., "Electrowetting-based actuation of droplets for integrated microfluidics," Lab Chip, 2002, vol. 2, pp. 96-101.
Pompano, Rebecca R. et al., "Rate of Mixing Controls Rate and Outcome of Autocatalytic Processes: Theory and Microfluidic Experiments with Chemical Reactions and Blood Coagulation,"Biophysical Journal, vol. 95, No. 3, (2008), pp. 1531-1543.
Potts, Matthew B. et al., "Models of Traumatic Cerebellar Injury," Cerebellum, vol. 8, No. 3, (2009) pp. 211-221.
Powers, Mark J. et al., "A Microfabricated Array Bioreactor for Perfused 3D Liver Culture" Biotechnology and Bioengineering, vol. 78, (2002), pp. 257-269.
Pregibon, Daniel C. et al., "Multifunctional Encoded Particles for High-Throughput Biomolecule Analysis," Science, vol. 315, (2007), pp. 1393-1396.
Proost, P. et al., "The Role of Chemokines in Inflammation" International Journal of Clinical & Laboratory Research, vol. 26, (1996), pp. 211-223.
Proust, Anna et al., "Functionalizaiton of Polyoxometalates: Towards Advanced Applications in Catalysis and Materials Science," Chem. Commun., (2008), pp. 837-1852.
Raghupathi, Ramesh et al., "Cell Death Mechanisms Following Traumatic Brain," Brain Pathology, vol. 14, No. 2, (2004), pp. 215-222.
Rah, Tatsukiet al., "The Novel Free Radical Scavenger, Edaravone, Increases Neural Stem Cell Number Around the Area of Damage Following Rat Traumatic Brain Injury. Neurotoxicity Research,"vol. 16, No. 4, (2009), pp. 378-389.
Ravula,Surendra K. et al., "Spatiotemporal Localization of Injury Potentials in DRG Neurons During Vincristine-Induced Axonal Degeneration," Neuroscience Letters, vol. 415, (2007), pp. 34-39.
Rida, A. et al., "Manipulation of Self-Assembled Structures of Magnetic Beads for Microfluidic Mixing and Assaying," Anal Chem., vol. 77, No. 21, (2004), pp. 6239-6246.
Riegger, L. et al., "Read-Out Concepts for Multiplexed Bead-Based Fluorescence Immunoassays on Centrifugal Microfluidic Platforms,"Sensors and Actuators A, vol. 126, (2006), pp. 455-462.
Rifai, Nader et al., Protein Biomarker Discovery and Validation: the Long and Uncertain Path to Clinical Utility, Nat. Biotechnol., vol. 24, No. 8 (2006), pp. 971-983.
Ringger, N. C. et al., "A Novel Marker for Traumatic Brain Injury: CSF alpha II-Spectrin Breakdown Product Levels" Journal of Neurotrauma, vol. 21, pp. 1443-1456.
Rissin, David M. et al., "Digital Concentration Readout of Single Enzyme Molecules Using Femtoliter Arrays and Poisson Statistics" Nano Letters, vol. 6, pp. 520-523.
Rissin, et al., Digital Readout of Target Binding with Attomole Detection Limits via Enzyme Amplification in Femtoliter Arrays, J. Am. Chem. Soc., vol. 128 (2006), pp. 6286-6287.
Roach, L. Spencer et al., "Controlling Nonspecific Protein Adsorption in a Plug-Based Microfluidic System by Controlling Interfacial Chemistry Using Fluorous-Phase Surfactants," Anal. Chem.,vol. 77, No. 3, (2005), pp. 785-796.
Rodemerck, U. et al., "Application of a Genetic algorithm and a Neural Network for the Discovery and Optimization of New Solid Catalytic Materials," Applied Surface Science, vol. 223, (2004), pp. 168-174.
Rodriguez-Villarreal, Angeles Ivan et al., "High Flow Rate Microfluidic Device for Blood Plasma Separation Using a Range of Temperatures," Lab Chip, vol. 10, (2010), pp. 211-219.
Romano, Joseph W. et al., "NASBA Technology: Isothermal RNA Amplification in Qualitative and Quantitative Diagnostics," Immunol Invest., vol. 26, Nos. 1&2, (1997), pp. 15-28.
Rowat, Amy C. et al., "Tracking Lineages of Single Cells in Lines Using a Microfluidic Device" Proceedings of the National Academy of Sciences of the United States of America, vol. 106, (2090), pp. 18149-18154.
Rowe, Laura et al., "Active 3-D Microscaffold System With Fluid Perfusion for Culturing in Vitro Neuronal Networks" Lab Chip, vol. 7, (2007), pp. 475-482.
Ryan, Colleen et al., "Rapid Assay for Mycobacterial Growth and Antibiotic Susceptibility Using Gel Microdrop Encapsulation,"J. Clin. Microbiol., vol. 33, No. 7, (1995), pp. 1720-1726.
Ryu, WonHyoung et al., "The Construction of Three-Dimensional Micro-Fluidic Scaffolds of Biodegradable Polymers by Solvent Vapor Based Bonding of Micro-Molded Layers," Biomaterials, vol. 28 (2007), pp. 1174-1184.
Sachs, Karen et al., "Causal Protein-Signaling Networks Derived from Multiparameter Single-Cell Data,"Science, vol. 308 (2005), pp. 523-529.
Sakaki, Kelly et al., "RoboSCell: An Automated Single Cell Arraying and Analysis Instrument" Biomedical Microdevices, vol. 11, (2009), pp. 1317-1330.
Sakudo, Akikazu et al., "Efficient Capture of Infectious H5 Avian Influenza Virus Utilizing Magnetic Beads Coated With Anionic Polymer,"Biochem. Biophys. Res. Commun., vol. 377, (2008), pp. 85-88.
Salemme, F.R. et al., "A Free Interface Diffusion Technique for the Crystallization of Proteins for X-Ray Crystallography," Archives of Biochemistry and Biophysics, vol. 151, (1972), pp. 533-539.
Sanishvili, Ruslan et al., "A 7 iiM Mini-Beam Improves Diffraction Data From Small or Imperfect Crystals of Macromolecules,"Biol. Crystallography, vol. D64, (2008), pp. 425-435.
Sano, Takeshi et al., "immuno-PCR: Very Sensitive Antigen Detection by Means of Specific Antibody-DNA Conjugates" Science, vol. 258, pp. 120-122.
Sasuga, Yasuhiro et al., Single-Cell Chemical Lysis Method for Analyses of Intracellular Molecules Using an Array of Picoliter-Scale Microwells, Anal. Chem., vol. 80, No. 23, (2008), pp. 9141-9149.

(56) References Cited

OTHER PUBLICATIONS

Sato, Kiichi et al., "Determination of Carcinoembryonic Antigen in Human Sera by Integrated Bead-Bed Immunoasay in a Microchip for Cancer Diagnosis," Anal. Chem.vol. 73, No. 6, (2001), pp. 1213-1218.

Schmitz, Christian H.J. et al., "Dropspots: A Picoliter Array in a Microfluidic Device," Lab Chip, vol. 9, (2009), pp. 44-49.

Scott, Lesley E. et al., "Evaluation of the Abbott m2000 RealTime Human Immunodeficiency Virus Type 1 (HIV-1) Assay for HIV Load Monitoring in South Africa Compared to the Roche Cobas AmpliPrep-Cobas Amplicor, Roche Cobas AmpliPrep-Cobas Taq-Man HIV-1, and BioMerieux NucliSENS EasyQ HIV-1 Assays," J. Clin. Microbiol. , vol. 47, (2009), pp. 22092217.

Selvin, Paul R. "Principles and Biophysical Applications of Lanthanide-Based Probes,"Annu. Rev. Biophys. Biomol. Struct., vol. 31, (2002), pp. 275-302.

Senkan, Selim, "Combinatorial Heterogeneous Catalysis-A New Path in an Old Field," Angew Chem.-Int. Edit., vol. 40, (2001), pp. 312-329.

Seong, Gi Hun et al., "Efficient Mixing and Reactions within Microfluidic Channels Using Microbead-Supported Catalysts" JACS, 2002, vol. 124, pp. 13360-13361 (Published Online Oct. 17, 2002).

Seong, Gi Hun et al., "Fabrication of Microchambers Defined by Photopolymerized Hydrogels and Weirs within Microfluidic Systems: Application to DNA Hybridization", Anal. Chem., 2002, vol. 74, pp. 3372-3377 (Published Online Jun. 6, 2002).

Sharma, Rajesh K. et al., "Multiplex Immunoassay Analysis of Biomarkers in Clinically Accessible Quantities of Human Aqueous Humor," Molecular Vision, vol. 15, (2009), pp. 6069.

Shaw, C.T. et al., "Using Cluster Analysis to Classify Time Series," Physica D. vol. 58, (1992), pp. 288-298.

Shen, Hong et al., "A Microfluidic Chip Based Sequential Injection System with Trapped Droplet Liquid-Liquid Extraction and Chemiluminescence Detection," Lab Chip, vol. 6, (2006), pp. 1387-1389.

Sherlock, Gavin, "Analysis of Large-Scale Gene Expression Data,"Current Opinion in Immunology, vol. 12, (2000), pp. 201-205.

Shestopalov, Ilya, "Multi-step synthesis of nanoparticles performed on millisecond time scale in a microfluidic droplet-based system," Lab Chip, 2004, vol. 4, pp. 3-8.

Shestopalov, Ilya., et al., "Multi-Step Synthesis of Nanoparticles Performed on Millisecond Time Scale in a Microfluidic Droplet-Based System", Lab-Chip, 2004, vol. 4, pp. 316-321.

Shi, Weiwei et al., "Droplet-Based Microfluidic System for Individual Caenorhabditis Elegans Assay," Lab on a Chip, vol. 8, (2008), pp. 1432-1435.

Shih, le-Ming et al., "Evidence That Genetic Instability Occurs at an Early Stage of Colorectal Tumorigenesis,"Cancer Research, vol. 61, (2001), pp. 818-822.

Shilov, alexander E. et al., "Activation of C—H Bonds by Metal Complexes,"Chem. Rev., vol. 97, No. 8, (1997), pp. 2879-2932.

Shim, et al., "Control and Measurement of the Phase Behavior of Aqueous Solutions Using Microfluidics,"Journal of the American Chemical Society, vol. 129, (2007), pp. 8825-8835.

Shim, Jung-uk et al., Simultaneous Determination of Gene Expression and Enzymatic Activity in Individual Bacterial Cells in Microdroplet Compartments, J. Am. Chem. Soc., vol. 131, (2009), pp. 15251-15256.

Shimazawa, Masamitsu et al., "A Novel Calpain Inhibitor, ((1S)-1-((((1S)-1-Benzyl-3 Cyclopropylamino-2, 3-dioxopropyl)amino)carbonyl)-3-methylbutyl)carbamic Acid 5-Methoxy-3-oxapentyl Ester (SNJ-1945), Reduces Murine Retinal Cell Death In Vitro and In Vivo," Journal of Pharmacology and Experimental Therapeutics, vol. 332, No. 2, (2010), pp. 380387.

Shumway, Robert H. et al., "Time Series Analysis and Its Applications With R Examples," Springer Science Business Media, LLC: New York, NY, 2006, 12p.

Sia, Samuel K. et al., "An Integrated Approach to a Portable and Low-Cost Immunoassay for Resource-Poor Settings"Angewandte Chemie-International Edition, vol. 43, pp. 498-502.

Sickmann, albert et al., "Towards a High Resolution Separation of Human Cerebrospinal Fluid,"Journal of Chromatography B-Analytical Technologies in the Biomedical and Life Sciences, vol. 771, No. 1-2, (2002), pp. 167-196.

Sikes, Hadley D. et al., "Antigen Detection Using Polymerization-Based Amplification" Lab Chip, vol. 9, pp. 653-656.

Sikes, Hadley D. et al., "Using Polymeric Materials to Generate an Amplified Response to Molecular Recognition Events" Nature Materials, vol. 7, pp. 52-56.

Siman, Robert et al., "A Panel of Neuron-Enriched Proteins as Markers for Traumatic Brain Injury in Humans," Journal of Neurotrauma, vol. 26, No. 11, (2009), pp. 1867-1877.

Sindelka, Radek et al., "Intracellular Expression Profiles Measured by Real-Time PCR Tomography in the Xenopus Laevis Ooocyte,"Nucleic Acids Research, vol. 36, No. 2, (2008), pp. 387-392.

Sista, Ramakrishna et al., "Development of a Digital Microfluidic Platform for Point of Care Testing," Lab Chip, vol. 8, (2008), pp. 2091-2104.

Sista, Ramakrishna et al., "Heterogeneous Immunoassays Using Magnetic Beads on a Digital Microfluidic Platform," Lab Chip, vol. 8, (2008), pp. 2188-2196.

Sohn, Kee-Sun et al., "Genetic algorithm—Assisted Combinatorial Search for a New Green Phosphor for Use in Tricolor White LEDs," J. Comb. Chem., vol. 8, (2006), pp. 44-49.

Sollier, Elodie et al., "Passive Microfluidic Devices for Plasma Extraction From Whole Human Blood,"Sensors and Actuators B: Chemical, vol. 141 (2009), pp. 617-624 (2009).

Solomon, Sunil S. et al., "Dried Blood Spots (DBA): A Valuable Tool for HIV Surveillance in Developing/Tropical Countries," International Journal of STD & AIDS, vol. 13, (2002), pp. 2528.

Song, Helen et al., "Experimental Test of Scaling of Mixing by Chaotic Advection in Droplets Moving Through Microfluidic Channels,"Applied Physics Letters, vol. 83, No. 22, (2003), pp. 4664-4666.

Song, Helen et al., "Millisecond Kinetics on a Microfluidic Chip Using Nanoliters of Reagents. Journal of the American Chemical Society,"vol. 125, No. 47, (2003), pp. 14613-14619.

Song, Helen et al., "On-Chip Titration of an Anticoagulant Argatroban and Determination of the Clotting Time Within Whole Blood or Plasma Using a Plug-Based Microfluidic System," Analytical Chemistry, vol. 78, No. 14, (2006), pp. 4839-4849.

Song, Helen et al., "Reactions in Droplets in Microfluidic Channels,"Angew. Chem. Int. Ed. vol. 45, (2006), pp. 7336-7356.

Souteyrand, Yves, P. et al., "Free Care at the Point of Service Delivery: a Key Component for Reaching Universal Access to HIV/AIDS Treatment in Developing Countries," AIDS, vol. 22, No. 1, (2008), S161-S168.

Spaid, Michael et al., "High Throughput Analysis Using Microemulsions for Reagent Encapsulation," 7th International Conference on Miniaturized Chemical and Biochemical Analysis Systems, Oct. 2003, pp. 445-448.

Spokoyny, alexander M. et al., "Infinite Coordination Polymer Nano- and Microparticle Structures," Chem. Soc. Rev., vol. 38, (2009), pp. 1218-1227.

Spurgeon, Sandra L. et al., "High Throughput Gene Expression Measurement with Real Time PCR in a Microfluidic Dynamic Array,"PLoS ONE, vol. 3, Issue 2, (2008), pp. e1662.

Squires, Todd M. et al., "Microfluidics: Fluid Physics at the Nanoliter Scale," vol. 77, (2005), pp. 977-1026.

Stahl, Shannon S. et al., "Homogeneous Oxidation of alkanes by Electrophili Late Transition Metals, Angew. Chem. Int. Ed., vol. 37, (1998), pp. 2180-2191.

Steegen, Kim et al., "Evaluation of Two Commercially Available alternatives for HIV-1 Viral Load Testing in Resource-Limited Settings," Journal of Virological Methods, vol. 146 (2007), pp. 178-187.

Sterne, Theodore E. "Some Remarks on Confidence or Fiducial Limits,"Biometrika, vol. 41, No. 1/2 (1954), pp. 275-278.

(56) References Cited

OTHER PUBLICATIONS

Stoll, Monika et al., "A Genomic-Systems Biology Map for Cardiovascular Function," Science, vol. 294, No. 5547, (2001), pp. 1723-1726.
Story, Craig M. et al., "Profiling Antibody Responses by Multiparametric Analysis of Primary B Cells," PNAS, vol. 105, No. 46, (2008), pp. 17902-1790.
Stuart, Jeffrey N. et al., "The Chemistry of Thought: Neurotransmitters in the Brain,"Analytical Chemistry, vol. 76, No. 7, (2004), pp. 120-128.
Sugiura, Shinji et al., "Interfacial Tension Driven Monodispersed Droplet Formation from Microfabricated Channel Array", Langmuir, 2001, vol. 17, pp. 5562-5566.
Sung, Wang Chou et al,, "Chip-based microfluidic devices coupled with electrospray ionization-mass spectrometry," Electrophoresis, 2005, vol. 26, pp. 1783-1791.
Szabo, Zsofia et al., "Voluntary Exercise May Engage Proteasome Function to Benefit the Brain After Trauma,"Brain Research, vol. 1341, (2010) pp. 25-31.
Takats, Zoltan et al., "Ambient Mass Spectrometry Using Desorption Electrospray Ionization (DES!): Instrumentation, Mechanisms and Applications in Forensics, Chemistry, and Biology," Journal of Mass Spectrometry, vol. 40, No. 10, (2005), pp. 1261-1275.
Takeuchi, Shoji et al., "Controlling the Shape of Filamentous Cells of *Escherichia coli*,"Nano Lett., vol. 5, No. 9 (2005), pp. 1819-1823.
Talasaz, Amirali H. et al., "Isolating Highly Enriched populations of Circulating Epithelial Cells and Other Rare Cells From Blood Using a Magnetic Sweeper Device". Proceedings of the National Academy of Sciences of the United States of America, vol. 106, (2009), pp. 39703975.
Tan, Swee Jin et al., "Microdevice for the Isolation and Enumeration of Cancer Cells From Blood". Biomedical Microdevices, vol. 11, (2009), pp. 883-892.
Tanaka, Hideo et al., "Ethanol Production from starch by a Coimmobilized Mixed Culture System of Aspergillus awamori and Zymomonas mobilis," Biotechnology and Bioengineering,1986, vol. XXVIII, pp. 1761-1768.
Taton, Andrew T. et al., "Scanometric DNA Array Detection with Nanoparticle Probes" Science, vol. 289, pp. 1757-1760.
Teh, Shia-Yen et al., "Droplet Microfluidics," Lab Chip, vol. 8 (2008), pp. 198-220.
Tharp, William G. et al., "Neutrophil Chemorepulsion in Defined Interleukin-8 Gradients in Vitro and in Vivo"Journal of Leukocyte Biology, vol. 79, (2006), pp. 539-554.
Theberge, Ashleigh B. et al., "Microdroplets in Microfluidics: An Evolving Platform for Discoveries in Chemistry and Biology," Angew. Chem. Int. Ed., 2010, vol. 49, pp. 5846-5868.
Thiel, Johannes et al., "Heteroatom-Controlled Kinetics of Switchable Polyoxometalate Frameworks,"J. Am. Chem. Soc., vol. 131, (2009), pp. 4180-4181.
Thomas, Sydney et al., "Review of Ways to Transport Natural Gas Energy From Countries Which Do Not Need the Gas for Domestic Use," Energy, vol. 28, (2003), pp. 1461-1477.
Thorsen, Todd, et al., "Dynamic Pattern Formation in a Vesicle-Generating Microfluidic Device", Phys. Rev. Lett., 2001, vol. 86, No. 18, pp. 4163-4166.
Thorslund, Sara et al., "A Hybrid Poly(Dimethylsiloxane) Microsystem for On-Chip Whole Blood Filtration Optimized for Steroid Screening," Biomed Microdevices Biomed Microdevices, vol. 8, (2006), pp. 73-79.
Tice, Joshua et al., "Effects of Viscosity on Droplet Formation and Mixing in Microfluidic Channels,"Analytica Chimica Acta, vol. 507, No. 1, (2004), pp. 73-77.
Tice, Joshua et al., "Formation of Droplets and Mixing in Multiphase Microfluidics at Low Values of the Reynolds and the Capillary Numbers," Langmuir, vol. 19, No. 22 (2003), pp. 9127-9133.
Titomanlio, G. et al., "Capillary Experiments of Flow Induced Crystallization of HDPE," AIChE Journal, Jan. 1990, vol. 36, No. 1, pp. 13-18.
Toh, Yi-Chin et al., "A Novel 3D Mammalian Cell Perfusion-Culture System in Microfluidic Channels," Lab Chip, No. 7, (2007), pp. 302-309.
Torkkeli, altti et al., "Droplet Manipulation on a Superhydrophobic Surface for Microchemical Analysis," The 11th International Conference on Solid-State Sensors and Actuators, Jun. 2001, 4 pages.
Tourovskaia, Anna et al., "Local Induction of Acetylcholine Receptor Clustering in Myotube Cultures Using Microfluidic Application of Agrin," Biophysical Journal, vol. 90, (2006), pp. 2192-2198.
Tranchemontagne,David J. et al., "Reticular Chemistry of Metal-Organic Polyhedra,"Angew. Chem.-Int. Edit., vol. 47, (2008), pp. 5136-5147.
Tsigdinos,George A. et al., Molybdovanadophosphoric Acids and Their Salts, J Inorg. Chem., vol. 7, (1968), pp. 437-441.
Tucci, Sonia et al., "Glutamate Measured by 6-s Resolution Brain Microdialysis: Capillary Electrophoretic and Laser-Induced Fluorescence Detection Application,"Journal of Chromatography B-Analytical Technologies in the Biomedical and Life Sciences, vol. 694, No. 2, (1997), pp. 343-349.
Tuteja, Anish et al., "Robust Omniphobic Surfaces," Proc. Natl. Acad. Sci. U. S. A., vol. 105, (2008), pp. 18200-18205.
Underhill, Gregory et al., "High-Throughput Analysis of Signals Regulating Stem Cell Fate and Function,"Current Opinion in Chemical Biology, vol. 11, (2007), pp. 357-366.
Unger, Marc A. et al., "Monolithic Microfabricated Valves and Pumps by Multilayer Soft Lithography,"Science, vol. 288, No. 5463 (2000), pp. 113-116.
Unknown author, "Extending the idea of using plugs for crystallization of proteins: screening and crystallization directly inside a capillary inside which the structure may be determined," protein__crystals_capillary_VD_1.FH10, 1 page.
Unknown author, "Extending the idea of using plugs for crystallization of proteins: screening and crystallization directly inside a capillary inside which the structure may be determined," protein__crystals_capillary_MB_1.FH10, 1 page.
Unknown Author, "HIV/AIDS Policy Fact Sheet," The Henry Kaiser Family Foundation, (Nov. 2009), 3p. http://www.kff.org/hivaids/upload/7029-05.pdf.
Unknown author, "Separating Nucleation and Growth," 8 slides.
Unknown Author, "The CCP4 Suite: Programs for Protein Crystallography", Acta Cryst (1994) D50, pp. 760-763.
Unknown Author, "The Global HIV Challenge: Assessing Progress, Identifying Obstacles, Renewing Commitment," UNAIDS Report on the Global Aids Epidemic, Executive Summary (2008).
Unknown Author, "Towards Universal Access—Scaling Up Priority HIV/AIDs Interventions in the Health Sector," WHO UNAIDS, Progress Report, 2009, 164 pages.
Urdea, Mickey et al., "Requirements for High Impact Diagnostics in the Developing World," vol. 444, Suppl 1, (2006), pp. 73-79.
Uttamchandani, Mahesh et al., "Small Molecule Microarrays: Recent Advances and Applications,"Curr. Opin. Chem. Biol., vol. 9, (2005), pp. 4-13.
Uttayarat, Pimpon et al. "Topographic Guidance of Endothelial Cells on Silicone Surfaces with Micro- to Nanogrooves: Orientation of Actin Filaments and Focal Adhesions" Journal of Biomedical Materials Research Part A 75A, (2005), pp. 668-680.
Vagin, alexei et al., "MOLREP: An Automated Program for Molecular Replacement," J. Appl. Cryst., vol. 30, (1997), pp. 1022-1025.
Vail, J.H. et al., "Enumeration of Waterborne *Escherichia coli* With Petrifllm Plates: Comparison to Standard Methods,"J. Environ. Qual., vol. 32, No. 1 (2003), pp. 368-373.
Valero, S. et al., "DoE Framework for Catalyst Development Based on Soft Computing Techniques,"Comput. Chem. Eng., vol. 33, (2009), pp. 225-238.
Van Delinder, Virginia et al., "Separation of Plasma From Whole Human Blood in a Continuous Cross-Flow in a Molded Microfluidic Device," Anal. Chem., vol. 78, (2006), pp. 3765-3771.
Van Staden, J.F. "Membrane Separation in Flow Injection Systems,"Fresenius J. Anal Chem. vol. 352, (1995), pp. 271-302.

(56) References Cited

OTHER PUBLICATIONS

Vandenabeele, Steven et al., "A Comprehensive Analysis of Hydrogen Peroxide-Induced Gene Expression in Tobacco,"Proceedings of the National Academy of Sciences of the United States of America, vol. 100, No. 26 (2003), pp. 16113-16118.
Vargaftik, M.N. et al., "Highly Selective Partial Oxidation of Methane to Methyl Trifluoroacetate," J. Chem. Soc.-Chem. Commun.,(1990), pp. 1049-1050.
Villa-Diaz, Luis Gerardo et al., "Microfluidic Culture of Single Human Embryonic Stem Cell Colonies," Lab Chip, vol. 9, (2009), pp. 1749-1755.
Vozzi, Giovanni et al., "Fabrication of PLGA Scaffolds Using Soft Lithography and Microsyringe Deposition," Biomaterials, vol. 24, (2003), pp. 2533-2540.
Vozzi,G. et al., "Microsyringe-Based Deposition of Two-Dimensional and Three-Dimensional Polymer Scaffolds with a Well-Defined Geometry for Application to Tissue Engineering," Tissue Engineering, vol. 8, No. 6 (2002), pp. 1089-1098.
Vriamont, Nicolas et al., "Design of a Genetic algorithm for the Simulated Evolution of a Library of Asymmetric Transfer Hydrogenation Catalysts,"Chem.-Eur. J., vol. 15, (2009), pp. 6267-6278.
Wages, S.A. et al., "Sampling Considerations for Online Microbore Liquid-Chromatography of Brain Dialysate,"Analytical Chemistry, vol. 58, No. 8, (1986), pp. 1649-1656.
Walker, G. Terrance et al., "Strand Displacement Amplification—An Isothermal, In Vitro DNA Amplification Technique,"Nucleic Acids Res., vol. 20, No. 7 (1992), pp. 1691-1696.
Walker, Glenn M. et al., "A Linear Dilution Microfluidic Device for Cytotoxicity Assays," Lab Chip, vol. 7, (2007), pp. 226-232.
Walt, David R., "Fibre Optic Microarrays,"Chem. Soc. Rev., vol. 39, (2010), pp. 38-50.
Wang, Min et al., "Palladium-Silver Thin Film for Hydrogen Sensing (Sensors and Actuators" B: Chemical, vol. 123(1), (2007), pp. 101-106.
Wang, Qiangbin et al., "Photonic Interaction Between Quantum Dots and Gold Nanoparticles in Discrete Nanostructures through DNA Directed Self-Assembly," Chemical Communications, vol. 46, 2010, pp. 240-242.
Wang, Ying-Chih et al., "Million-Fold Preconcentration of Proteins and Peptides by Nanofluidic Filter,"Analytical Chemistry, vol. 77, (2005), pp. 4293-4299.
Warden, Deborah, "*Military TBI During the Iraq and Afghanistan Wars*," J. Head Trauma Rehabil., vol. 21, No. 5, (2006), pp. 398-402.
Warren, Luigi et al., Transcription Factor Profiling in Individual Hematopoietic Progenitors by Digital RT-PCR, Proc. Natl. Acad. Sci. U. S. A., vol. 103, No. 47 (2006), pp. 17807-17812.
Watson, Christopher J. et al., in Vivo Measurements of Neurotransmitters by Microdialysis Sampling, Analytical Chemistry, vol. 78, No. 5, (2006), pp. 1391-1399.
Webb, Anna et al., "Guidance of Oligodendrocytes and Their Progenitors by Substratum Topography"Journal of Cell Science, vol. 108, (1995), pp. 2747-2760.
Weight, Ryan M. et al., "Photoacoustic Detection of Metastatic Melanoma Cells in the Human Circulatory System" Optics Letters, vol. 31, (2006), pp. 2998-3000.
Weinberg, David R. et al., "Competitive Oxidation and Protonation of Aqueous Monomethylplatinum(II) Complexes: A Comparison of Oxidants," Organometallics, vol. 26, (2007), pp. 167-172.
Weiss, David J. et al., "In Vivo Microdialysis as a Tool for Monitoring Pharmacokinetics,"Trac-Trends in Analytical Chemistry, vol. 19, No. 10, (2000), pp. 606-616.
Wen, Ji-Kai et al., "A Visual DNA Chip for Simultaneous Detection of Hepatitis B Virus, Hepatitis C Virus and Human Immunodeficiency Virus Type-1"Biosensors & Bioelectronics, vol. 19, pp. 685-692.
Wheeler, M.B. et al., "Toward Culture of Single Gametes: The Development of Microfluidic Platforms for Assisted Reproduction"Theriogenology, vol. 68, (2007), S178-S189.
Wheeler, Rob C. et al., "Mesoscale Flow Chemistry: A Plug-Flow Approach to Reaction Optimisation," Org. Process Res. Dev., vol. 11, (2007), pp. 704-710.
Whitesides, George M. et al., "The Origins and the Future of Microfluidics,"Nature, vol. 442, (2006), pp. 368-373.
Wismuller, Axel et al., "Cluster Analysis of Biomedical Image Time-Series" International Journal of Computer Vision, vol. 42, No. 2, (2002), pp. 103-128.
Wojcik, Barbara E. et al., "Traumatic Brain Injury Hospitalizations of US Army Soldiers Deployed to Afghanistan and Iraq,"American Journal of Preventive Medicine, vol. 38, No. 1, (2010), pp. S108-S116.
Wolf, D. et al., "An Evolutionary Approach in the Combinatorial Selection and Optimizaiton of catalytic Materials," Appl. Catal. A-Gen., vol. 200, (2000), pp. 63-77.
Wong, Amy P. et al., "Partitioning Microfluidic Channels With Hydrogel to Construct Tunable 3-D Cellular Microenvironments," Science Direct Biomaterials, vol. 29, (2008), pp. 18531861.
Wong, Pak Kin et al., "Electrokinetic Biopressor for Concentrating Cells and Molecules," Anal. Chem., vol. 76, No. 23, (2004), pp. 6908-6914.
Woodward, R.L., "*How Probable is the Most Probable Number*" J. Am. Water Works As. vol. 49, (1957), pp. 1060-1068.
Wu, Liang, et al., "Droplet Formation in Microchannels Under Static Conditions," Appl. Phys. Lett. vol. 89, (2006), pp. 144106.
Xia, Younan et al., "Soft Lithography" Angewandte Chemie-International Edition, vol. 37, No. 5, (1998) pp. 551-575.
Xiong, Ye et al., "Emerging Treatments for Traumatic Brain Injury," Expert Opinion on Emerging Drugs, vol. 14, No. 1, (2009), pp. 67-84.
Yamanaka, Ichiro et al., "Oxidation of Methane and Benzene with Oxygen Catalyzed by Reduced Vanadium Species at 40° C," J. Mol. Catal. A-Chem., vol. 133, (1998), pp. 251-254.
Yang, Jianing et al., "High Sensitivity PCR Assay in Plastic Micro Reactors," Lab Chip, vol. 2, (2002), pp. 179-187.
Yang, Liying et al., "Optimization of an Enrichment Process for Circulating Tumor Cells From the Blood of Head and Neck Cancer Patients Through Depletion of Normal Cells," Biotechnology and Bioengineering, vol. 102, No. 2, (2009), pp. 521-534.
Yang, Sung-Yi et al., "Microflow Cytometry Utilizing a Magnetic Bead-Based Immunoassay for Rapid Virus Detection,"Biosensors and Bioelectronics, vol. 24, (2008), pp. 855-862.
Yeh, Chia-Hsien et al., "An Immunoassay Using Antibody-Gold Nanoparticle Conjugate, Silver Enhancement and Flatbed Scanner,"Microfluidics and Nanofluidics, vol. 6, (2009), pp. 85-91.
Yeung, K.Y. et al., "Principal Component Analysis for Clustering Gene Expression Data," Bioinformatics, vol. 17, No. 9, (2001), pp. 763-774.
Younes-Metzler, Osnat et al., "Microfabricated High-Temperature Reactor for Catalytic Partial Oxidation of Methane,"Applied Catalysis A: General, vol. 284, (2005), pp. 5-10.
Yu, Ji et al., "Probing Gene Expression in Live Cells, One Protein Molecule at a Time," Science, vol. 311, (2006), pp. 1600-1603.
Yuan, Yong J. et al., "Bond Rupture of Biomolecular Interactions by Resonant Quartz Crystal,"Analytical Chemistry, vol. 79, (2007), pp. 9039-9044.
Yuen, Po Ki et al., "Microfluidic Devices for Fluidic Circulation and Mixing Improve Hybridization Signal Intensity on DNA Arrays," Lab Chip, vol. 3, (2003), pp. 46-50.
Zhang, Qingquan et al., "Microfluidic Droplet Trapping Array as Nanoliter Reactors for Gas-Liquid Chemical Reaction," Electrophoresis, vol. 30, No. 18, (2009), pp. 3181-3188.
Zhang, Xin et al., "New Triple Microbore Cannula System for Push-Pull Perfusion of Brain Nuclei of the Rat,"Journal of Neuroscience Methods, vol. 32, (1990), pp. 93-104.
Zhang, Y.H. et al., "Microfluidic DNA Amplification-A Review," Analytica Chimica Acta, vol. 63, No. 2, (2009), pp. 115-125.
Zhang, Yi et al., "Putting the Invader Assay to Work: Laboratory Application and Data Management,"Methods Mol. Biol., vol. 578, (2009), pp. 363-377.

(56) References Cited

OTHER PUBLICATIONS

Zhang, Zhiqun et al., Calpain-Mediated Collapsin Response Mediator Protein-1,-2, and-4 Proteolysis After Neurotoxic and Traumatic Brain Injury, Journal of Neurotrauma, vol. 24, No. 3, (2007), pp. 460-472.

Zheng, Bo et al., "A Droplet-Based, Composite PDMS/Glass Capillary Microfluidic system for Evaluating Protein Crystallization Conditions by Microbatch and Vapor-Diffusion Methods With On-Chip X-ray Diffraction,"Angew. Chem. Int. Ed., vol. 43, (2004), pp. 2508-2511.

Zheng, Bo et al., "Formation of Arrayed Droplets of Soft Lithography and Two-Phase Fluid Flow, and Application in Protein Crystallization,"Advanced Materials, vol. 16, No. 15, (2004), pp. 1365-1368.

Zheng, Bo et al., "Formation of Droplets of alternating Composition in Microfluidic Channels and Applications to Indexing of Concentrations in Droplet-Based Assays", Analytical Chemistry, 2004, vol. 76, pp. 4977-4982.

Zheng, Bo et al., "Screening of Protein Crystallization Conditions on a Microfluidic Chip Using Nanoliter-Size Droplets,"J. Am. Chem. Soc., vol. 125, (2003), pp. 11170-11171.

Zheng, Bo et al., "Using Nanoliter Plugs in Microfluidics to Facilitate and Understand Protein Crystallization,"Current Opinion in Structure Biology, vol. 15, (2005), pp. 548-555.

Zheng, Siyang et al., "Membrane Microfilter Device for Selective Capture, Electrolysis and Genomic Analysis of Human Circulating Tumor Cells," Journal of Chromatography A, vol. 1162, (2007), pp. 154-161.

Zhou, Xuechang et al., "Nanoliter Dispensing Method by Degassed Poly(dimethylsiloxand) Microchannels and Its Application in Protein Crystallization,"Anal. Chem., vol. 79, No. 13, (2007), pp. 4924-4930.

Ziatdinov, Vadim R. et al., "Carboxylic Solvents and 0-Donor Ligand Effects on CH Activation by Pt(ll)," J. Am. Chem. Soc., vol. 128, (2006), pp. 7404-7405.

Zieglschmid, V. et al., "Detection of Disseminated Tumor Cells in Peripheral Blood" Critical Reviews in Clinical Laboratory Sciences, vol. 42, (2005), pp. 155-196.

Zimmermann, Bernhard G. et al., "Digital PCR: A Powerful New Tool for Noninvasive Prenatal Diagnosis?" Prenatal Diagnosis, vol. 28, (2008), pp. 1087-1093.

Great Basin Corporation. Isothermal Amplification. Available at www.gbscience.com/technology/iso-amp. Accessed Jan. 6, 2014.

Great Basin Corporation. Sample-to-Result Molecular Diagnostics. Available at www.gbscience.com. Accessed Jan. 6, 2014.

Great Basin Corporation. Technology—Early appropriate treatment of infections is critical for good patient outcomes and to manage treatment costs. Available at www.gbscience.com/technology. Access Jan. 6, 2014.

International search report and written opinion dated May 10, 2010 for PCT Application No. PCT/U2010/28316.

Rea, et al. Point-of-Care Molecular Diagnostic Testing. Created Dec. 12, 2012 20:17. Published: Dec. 12, 2012. Published on IVD Technology. Available at http://www.ivdtechnology.com/print/3097. Accessed Jan. 6, 2014.

US 7,897,368, 03/2011, Handique et al. (withdrawn).

Office action dated Aug. 14, 2014 for U.S. Appl. No. 13/440,371.

Office action dated Aug. 15, 2014 for U.S. Appl. No. 13/257,811.

Office Action for U.S. Appl. No. 13/440,371, dated Jun. 19, 2015, 13 Pages.

Office Action for U.S. Appl. No. 14/177,190, dated Sep. 15, 2015, 24 Pages.

Official Notification for Israeli Patent Application No. 215160, dated Jul. 27, 2015, 4 Pages.

United States Office Action, U.S. Appl. No. 14/177,194, Apr. 26, 2016, 14 Pages.

\* cited by examiner

Figure 5
(a)
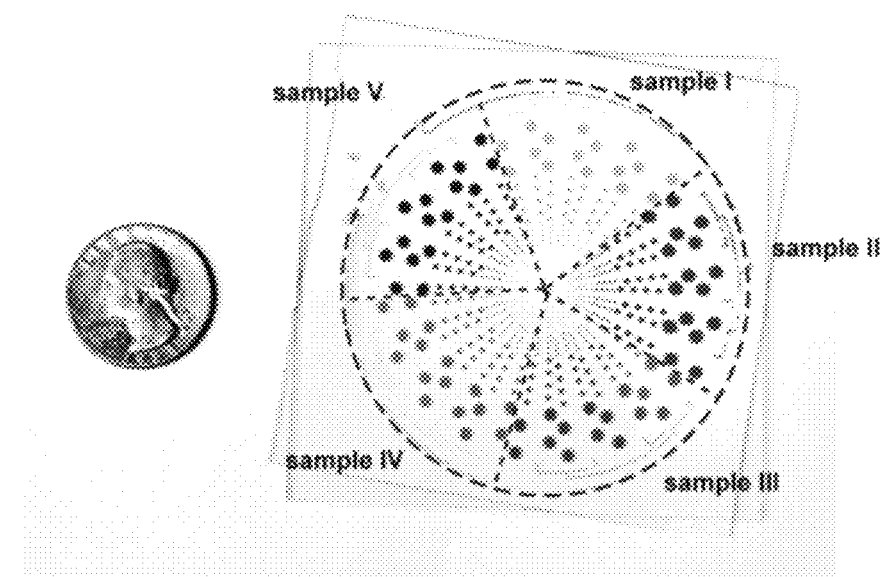
(b)
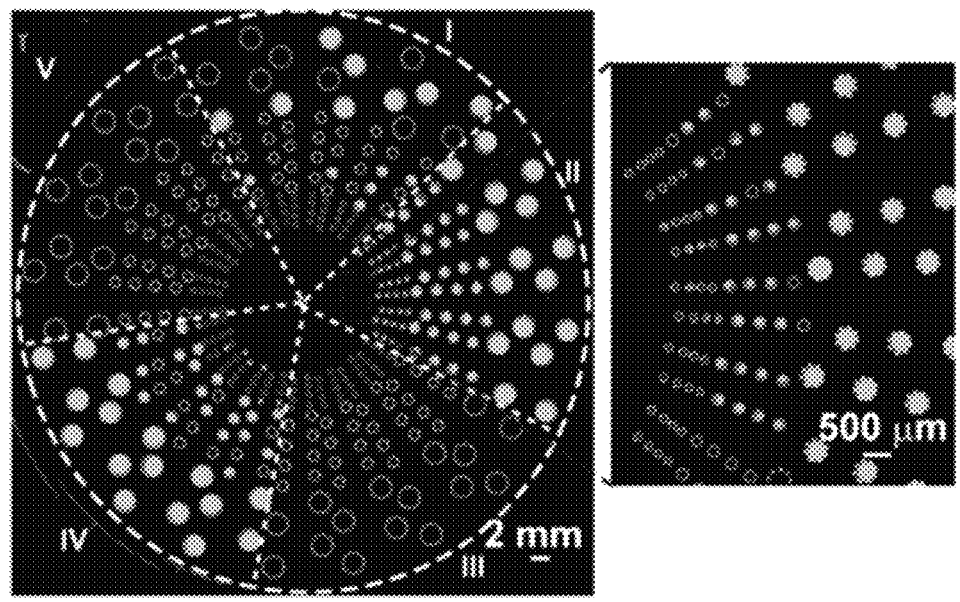

Figure 9

| Dilution Factor | Expected p HIV viral RNA concentration based on a Roche CAP/CTM v2.0 test (molecules/mL) | Average of calculated HIV viral RNA concentration based on experiments on SlipChip (molecules/mL) | Standard deviation of calculated HIV viral RNA concentration based on experiments on SlipChip (molecules/mL) |
|---|---|---|---|
| 1 | $2.3 \times 10^5$ | $1.6 \times 10^5$ | $1.3 \times 10^4$ |
| 1:10 | $2.3 \times 10^4$ | $1.3 \times 10^4$ | $3.0 \times 10^3$ |
| 1:100 | $2.3 \times 10^3$ | $1.4 \times 10^3$ | $6.5 \times 10^2$ |
| 1:1000 | $2.3 \times 10^2$ | 93 | 32 |

Figure 10

| Dilution Factor | Expected p HIV viral RNA concentration based on a Roche CAP/CTM v2.0 test (molecules/mL) | Average of calculated HIV viral RNA concentration based on experiments on SlipChip (molecules/mL) | Standard deviation of calculated HIV viral RNA concentration based on experiments on SlipChip (molecules/mL) |
|---|---|---|---|
| 1 | $1.5 \times 10^6$ | $1.7 \times 10^6$ | $3.9 \times 10^5$ |
| 1:20 | $7.3 \times 10^4$ | $9.2 \times 10^4$ | $4.0 \times 10^3$ |
| 1:400 | $3.6 \times 10^3$ | $3.3 \times 10^3$ | $6.3 \times 10^2$ |
| 1:8000 | $1.8 \times 10^2$ | $1.8 \times 10^2$ | 81 |
| 1:40000 | 36 | 37 | 37 |

MULTIVOLUME DEVICES, KITS AND RELATED METHODS FOR QUANTIFICATION OF NUCLEIC ACIDS AND OTHER ANALYTES

CROSS-REFERENCE

This application is a continuation-in-part application of application Ser. No. 13/440,371, filed on Apr. 5, 2012, which is a continuation-in-part application of application Ser. No. 13/257,811, filed Sep. 20, 2011; which is the National Stage of International Application No. PCT/US2010/028316, filed on Mar. 23, 2010, which claim the benefit under 35 U.S.C. §119(e) of U.S. Provisional Application 61/262,375, filed on Nov. 18, 2009, and U.S. Provisional Application No. 61/162, 922, filed on Mar. 24,2009, and U.S. Provisional Application No. 61/340,872, filed on Mar. 22, 2010; application Ser. No. 13/467,482 claims the benefit of U.S. Provisional Application No. 61/518,601, May 9, 2011; application Ser. No. 13/440,371 claim the benefit of U.S. Provisional Application No. 61/516,628, filed Apr. 5, 2011 and U.S. Provisional Application No. 61/518,601, filed May 9, 2011; the content of all of which are hereby incorporated by reference in their entireties for any and all purposes.

U.S. application Ser. No. 13/440,371 is also a continuation in part of U.S. application Ser. No. 13/257,811, "Slip Chip Device and Methods," filed on Sep. 20, 2011. That United States application is a national stage entry of international application PCT/US2010/028316, "Slip Chip Device and Methods," filed on Mar. 23, 2010. That international application claimed priority to U.S. Application 61/262,375, "Slip Chip Device and Methods," filed on Nov. 18, 2009, to U.S. Application 61/162,922, "Sip Chip Device and Methods," filed on Mar. 24, 2009, and to U.S. Application 61/340,872, "Slip Chip Device and Methods," filed on Mar. 22, 2010. All of the foregoing applications are incorporated herein by reference in their entireties for any and all purposes.

STATEMENT OF GOVERNMENT RIGHTS

This invention was made with government support under Grant Nos. 1 R01 EB012946, GM074961, and DP1OD003584, awarded by the National Institutes of Health; and Grant No. CHE-0526693, awarded by the National Science Foundation. The United States Government has certain rights in this invention.

SEQUENCE LISTING

The instant application contains a Sequence Listing which has been submitted in ASCII format via EFS-Web and is hereby incorporated by references in its entirety. Said ASCII copy, created on Jul. 13, 2012, is named Sequency Listing CRF CTSC0094.txt and is 2,138 bytes in size.

TECHNICAL FIELD

The present application relates to the field of microfluidics and to the fields of detection and amplification of biological entities.

BACKGROUND

Real-time quantitative RT-PCR is an existing technique for monitoring viral load for HIV, HCV, and other viral infections. However, this test is cost-prohibitive in some resource-limited settings and can require multiple instruments, skilled technicians, and isolated rooms to prevent contamination. The test can thus be inaccessible to patients in some resource-limited settings. Moreover, the efficiency of RT-PCR, the quality of sample and selection of targets, and the methods for interpretation of the data may in some cases present concerns for the accuracy of quantifying RNA using RT-PCR.

Although dipstick-type devices may provide semiquantitative measurements of viral load after amplification in resource limited settings, no quantitative test exists to resolve a 3-fold (i.e., appx. 0.5 $\log^{10}$) change in HIV RNA viral load, which change is considered clinically significant. Accordingly, there is a long-felt need in the art for devices and methods for quantitative measurement, estimates, and/ or even detection of viral load or other parameters.

SUMMARY

In meeting the described challenges, the present disclosure first provides devices. These devices comprise a first component comprising a population of first areas; a second component comprising a population of second areas; the first and second components being engageable with one another such that relative motion between the first and second components exposes at least some of the first population of areas to at least some of the second population of areas so as to form a plurality of analysis regions. At least some of the analysis regions suitably differ in volume from others of the analysis regions.

Also disclosed are devices. The devices suitably include a first component comprising a population of first areas; a second component comprising a population of second areas; the first and second components being engageable with one another such that when the first and second components are in a first position relative to one another a fluidic path is formed between at least some of the first areas and at least some of the second areas, and when the first and second components are in a second position relative to one another, the fluidic path is interrupted so as to isolate at least some of the first areas from at least some of the second areas.

Additionally provided are methods. These methods include distributing one or more target molecules from an original sample into a plurality of analysis regions, the distribution being effected such that at least some of the analysis regions are statistically estimated to each contain a single target molecule, at least two of the analysis regions defining different volumes; and effecting, in parallel, a reaction on at least some of the single target molecules.

Other methods presented in this disclosure include introducing an amount of a target molecule from an original sample into a device; effecting distribution of the amount of the target molecule into at least two isolated areas of the device, the at least two isolated areas defining volumes that differ from one another; effecting a reaction on the target molecule so as to give rise to a reaction product in the at least two isolated areas; and estimating, from the reaction product, the level of a target in the original sample.

Also provided are methods, comprising distributing a plurality of target molecules—suitably nucleic acids—from an original sample into a plurality of analysis regions, the distribution being effected such that at least some of the analysis regions are estimated to each contain a single target molecule, at least two of the analysis regions defining different volumes; and effecting, in parallel, a nucleic acid amplification reaction on at least some of the single target molecules.

Also disclosed are devices, comprising a first component comprising a population of first wells formed in a first surface of the first component, the population of wells being arranged in a radial pattern; a second component comprising a population of second wells formed in a first surface of the second component, the population of wells being arranged in a radial pattern; the first and second components being engageable with one another such that relative rotational motion between the first and second components exposes at least some of the first population of wells to at least some of the second population of wells so as to form a plurality of analysis regions, an analysis region comprising a first well and a second well in pairwise exposure with one another.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

FIG. 5 illustrates an exemplary device for multiplexed, multivolume digital RT-PCR with high dynamic range;

FIG. 9 illustrates in tabular form detection and quantification data;

FIG. 10 presents a tabular summary of HIV quantification performance;

FIG. 11 presents a tabular summary of detection range data;

FIG. 15 presents, in tabular form, a summary of the specifications of an exemplary device according to the present disclosure;

DETAILED DESCRIPTION OF ILLUSTRATIVE EMBODIMENTS

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise.

The term "plurality" as used herein, means more than one. When a range of values is expressed, another embodiment includes from the one particular value and/or to the other particular value. Similarly, when values are expressed as approximations, by use of the antecedent about, it will be understood that the particular value forms another embodiment. All ranges are inclusive and combinable. All documents cited herein are incorporated herein by reference in their entireties for any and all purposes.

In one embodiment, the present disclosure provides devices. These devices suitably include a first component comprising a population of first areas and a second component comprising a population of second areas. The first and second components are suitably engageable with one another such that relative motion between the first and second components exposes at least some of the first population of areas to at least some of the second population of areas so as to form a plurality of analysis regions. As described herein, at least some of the analysis regions may suitably differ in volume from other analysis regions.

In some embodiments, the first and second components are engaged so as to permit rotational motion of one component relative to the other component. This may be in the form of two plates that are rotatably engaged with one another, as shown in exemplary FIG. 1. As shown in panels A-D of that figure, the two plates may be rotatably engaged such that relative rotation between the plates gives rise to wells formed in the plates aligning with one another (i.e., being placed into at least partial register) or de-aligning from one another.

Also as shown in that exemplary figure (FIG. 1, panel G), a device may provide analysis regions that differ from one another in volume. For example, the analysis regions (formed between FIG. 1 panels F and G by relative rotational motion between two plates that gives rise to pairwise exposure of wells formed in the plates to one another) shown in FIG. 1 have volumes of about 1, 5, 25, and 125 nL.

Figure 1:
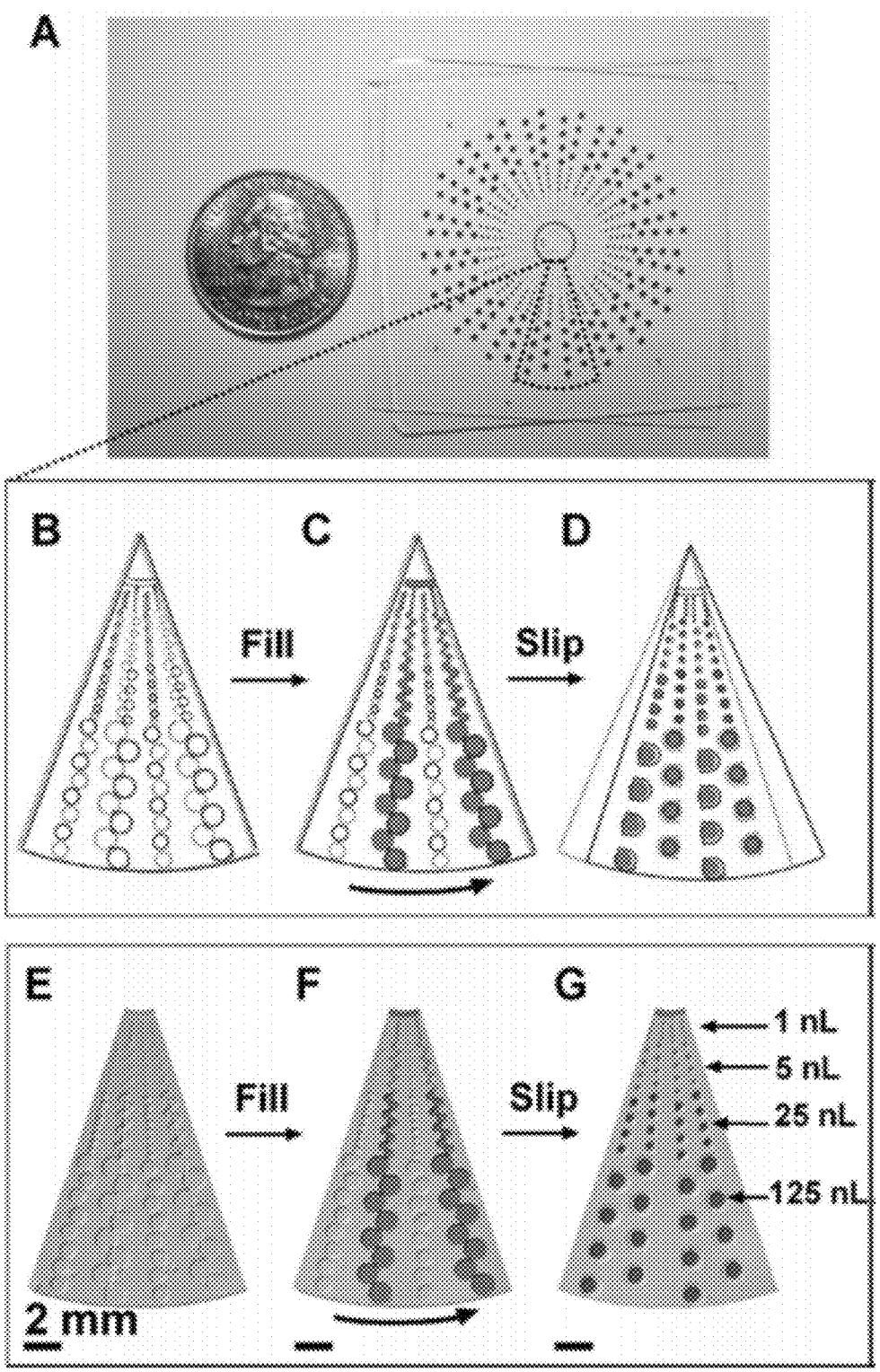
FIG. 1 illustrates a rotationally-configured multivolume device according to the present disclosure.

Although the analysis regions shown in FIG. 1 increase in volume with increasing radial distance outward from axis of rotation between the plates, there is no requirement that analysis regions vary such a size and/or spatial manners. Other embodiments of the disclosed devices feature first and second components engaged so as to permit linear movement of one component relative to the other component.

It should be understood that although exemplary FIG. 1 shows first and second components engaged with one another, the present disclosure is not limited to devices that have only two components. For example, a user may construct a device that has first, second, and third components that are engageable with one another. As but one example, the device shown in FIG. 1 may include a first well-bearing component that is engaged with one face of a second well-bearing component. The second face of the second well-bearing component may, in turn, be engageable with a third well-bearing component, such that the wells of the third component may be placed into overlap with the wells of the second face of the second well-bearing component. Such a structure may be in a layer-cake or sandwich form. These configurations enable increased information density, as such configurations allow creation of additional areas on a device where reactions and analysis may take place.

In an alternative embodiment, one surface of a component may be engaged with two other components. For example, a base component having formed thereon first and second circular banks of wells that are separate from one another may be engageable with [1] a first component that features wells that may be placed into overlap with the first bank of wells of the base component and [2] a second component that features wells that may be placed into overlap with the second bank of wells of the base component. In this way, a single device may feature multiple components so as to increase the number and diversity of reaction and/or analysis locations on the device.

The first and second components may be of a range of sizes. In some embodiments, at least one of the first or second components has a thickness in the range of from about 10 micrometers to about 5000 micrometers, or in the range of from about 50 micrometers to about 1000 micrometers, or even from about 200 micrometers to about 500 micrometers. These dimensions are particularly useful in applications where a user may desire a reduced-size device or a device having a relatively compact form factor. Components may be formed of a glass, a polymer, and the like.

Soda-lime glass is considered especially suitable; other component materials may also be used. Exemplary fabrication methods for such devices are set forth in Du et al., Lab Chip 2009, 9, 2286-2292. In some embodiments, components of the device are fabricated from a glass substrate by way of wet etching. In some other embodiments, the device can be fabricated from plastic materials, such as polycarbonate, Poly(methyl methacrylate) (PMMA), polypropylene, polyethylene, cyclo olefin copolymer (COC), cyclo olefin polymer (COP), and fluorinated polymers including but not limited to fluorinated ethylene-propylene FEP (fluorinated ethylene-propylene), perfluoroakoxy (PFA) and polytetrafluoroethylene (PTFE). Surfaces may be treated with methods such as silanization and physical deposition, such as vapor deposition techniques. As one example, a surface of the device may be treated with dichlorodimethylsilane by vapor silanization. The surface of the device can be coated with silicone or fluorinated polymers. Reaction fluids used in the devices may also include ingredients related to the surfaces of the devices. As one such example, bovine serum albumin is added to a PCR mixture to prevent adsorption and denaturation of molecules on a surface of the device.

In some embodiments (e.g., exemplary FIG. 5A), a component comprises a conduit that places at least some of the first population of wells into fluidic communication with the environment exterior to the component. In some embodiments, a population of wells is characterized as being radially disposed relative to a location on the first component, as shown in exemplary FIG. 5. Populations of wells may also be present in a circular pattern, a grid pattern, or virtually any other conformation. In some embodiments, a device (e.g., exemplary FIG. 5) may include several populations of wells that are each in fluid communication with their own conduits, which in turn enables a user to introduce different materials to different populations of wells. Exemplary FIG. 5 shows this by reference to a device having five separate banks of wells, each separate bank of wells containing a different sample (samples I-V). As shown in this exemplary figure, the banks of wells may be configured such that a given bank of wells maintains a sample (e.g., sample I) in isolation from other samples (e.g., sample II). In the exemplary FIG. 5a, each bank of separate wells in in a form that is roughly a wedge or a pie-slice in shape; banks of wells may have other layouts (grids, lines, and the like), depending on the device and on the user's needs. The device may be configured such that each bank of wells has an inlet configured to supply material (e.g., sample) to that bank of wells only. In this way, a device may have five banks of wells, each bank of wells being supplied by one or more separate inlet. A bank of wells may, of course, be supplied by one, two, three, or more inlets, depending on the user's needs. A device may also be configured such that a given inlet supplies material to at least some wells in two or more separate banks of wells.

Certain embodiments of the disclosed devices feature components where the first areas are wells formed on (or in) a component. In some embodiments, a well suitably has a volume in the range of from about 0.1 picoliter to about 10 microliters. In some variations, the second areas may be wells. Such wells suitably have volumes in the range of from about 0.1 picoliter to about 10 microliters.

When areas are placed into exposure with one another so as to give rise to analysis regions, an analysis region may, in some embodiments, have a volume in the range of from about 0.1 picoliter to about 20 microliters. The volumes of two analysis regions may differ from one another. As one example, the ratio of the volumes defined by two analysis regions is in the range of from about 1:1 to about 1:1,000,000, or from about 1:50 to about 1:1,000, or from about 1:100 to about 1:500. In the example shown in FIG. 1, the ratio between some of the analysis region volumes is 1 nl:125 nL=1:125.

The devices may also include an imager configured to capture at least one image of an analysis region. The imager may be a camera, CCD, PMT, or other imaging device. Portable imagers, such as digital cameras and cameras on mobile devices such as smartphones/mobile phones are considered suitable imagers. The device may be configured such that the imager is positioned such that it may capture an image of some of the analysis regions of a device or even an image of all of the analysis regions.

Figure 12:
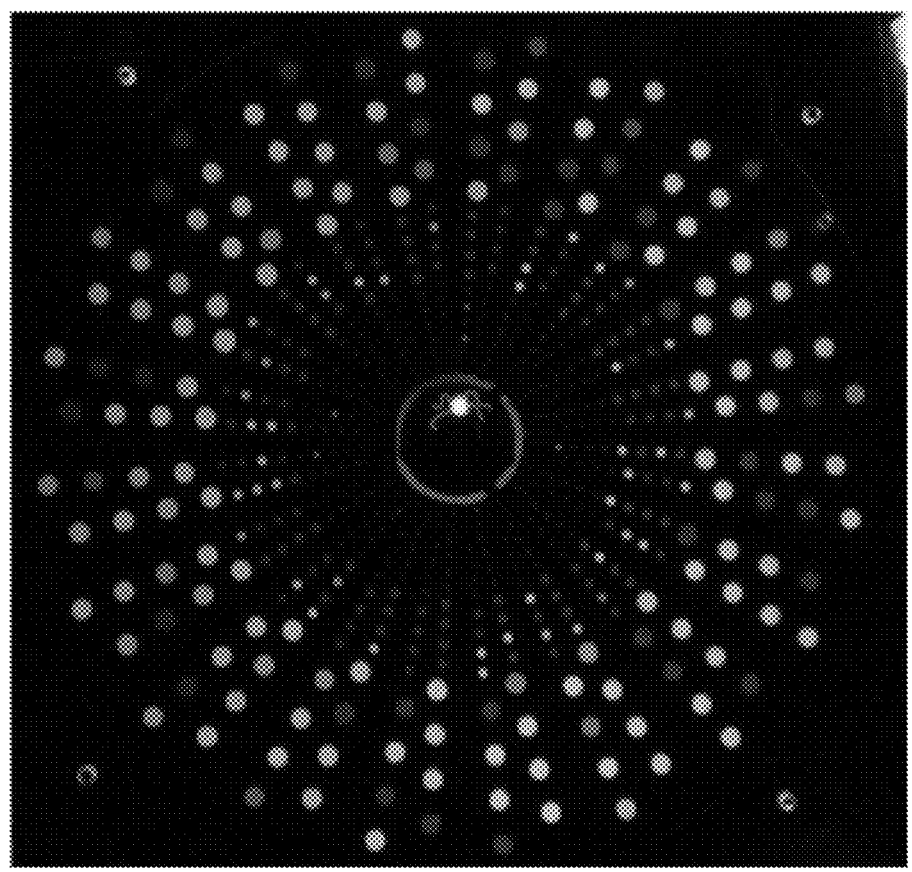
FIG. 12 shows an image, obtained with a iPhone 4S™ camera, of an exemplary multivolume device filled with LAMP reaction mix.
Figure 13:
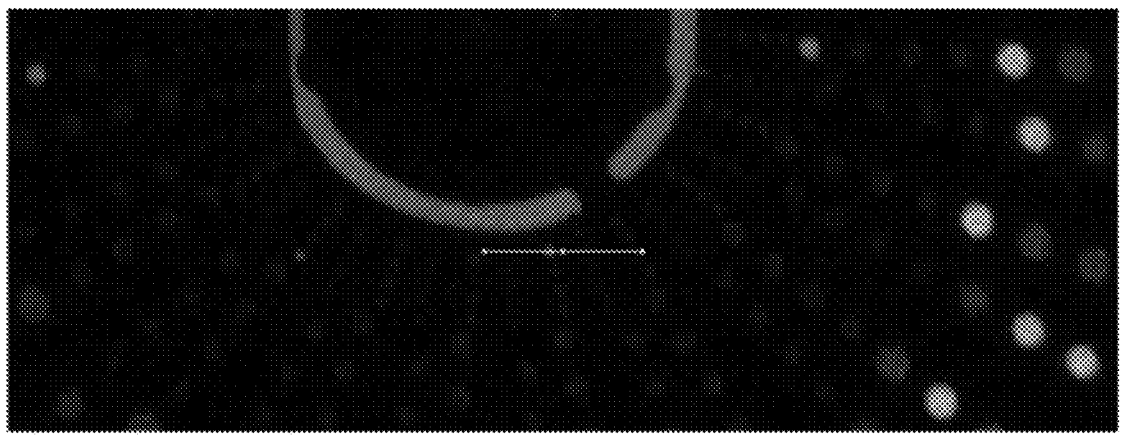
FIG. 13 shows a close-up of the center of the image in FIG. 12.

The devices may also be configured to display an image of an analysis region for capture of at least one image by an imager. As one example, the device may be configured, as shown in exemplary FIG. 2, to present or otherwise display the analysis regions in such a manner that the analysis regions (including their contents) may be imaged. Exemplary images are shown in FIGS. 12 and 13, which images were obtained using the camera of an iPhone 4S™ mobile device.

The devices may also include a processor configured to estimate a concentration of an analyte residing in one or more analysis regions. The processor may be present in the device itself; in such cases, the device may include the imager and a processor that is configured to estimate a concentration of an analyte residing in one or more analysis regions. This may be effected by, for example, a computer imaging routine configured to take as an input an image of the analysis regions of a device and then operate on that input (as described elsewhere herein) to estimate the concentration of an analyte in the one or more analysis regions. In one exemplary embodiment, the processor operates on an image of the analysis regions of the device and, from that, estimates the presence of an analyte in a sample.

As one example, a user may extract a blood sample from a subject to determine whether a particular virus is present in the subject. The user may then process the blood sample (e.g., cell isolation, cell lysis, and the like) and assay the sample (e.g., via PCR) for the presence of a particular nucleic acid that is a marker for the virus of interest. The processor may then, by analyzing the image of the analysis regions in which the nucleic acid may be present, statistically estimate the presence (if any) of the virus in the subject. The processor may, alternatively, be configured to detect the presence of the analyte in a yes/no fashion; this may be useful in situations where the user is interested only in knowing whether the subject has a virus and is less interested in knowing the level of that virus in the subject. Further information regarding exemplary processing methods is found in Kreutz et al., JACS 2011 133: 17705-17712; Kreutz et al., Anal. Chem. 2011 83: 8158-8168; and Shen et al., Anal. Chem. 2011 83: 3533-3540.

The disclosed devices are suitably configured to permit formation of 5, 10, 100, 500 or more analysis regions. In some embodiments, the devices are adapted to place at least about 10 first areas into pairwise exposure with at least 10 second areas. This pairwise exposure in turn effects formation of 10 analysis regions. The devices may also be adapted so as to be capable of placing at least about 100 first areas into pairwise exposure with at least 100 second areas, or even placing at least about 200 first areas into pairwise exposure with at least 200 second areas. Exemplary FIG. 1 shows (by way of the "slip" rotational motion shown between FIG. 1 panels C and D) placement of filled wells (darkened circles) into exposure with unfilled wells (unfilled circles).

Devices according to the present disclosure may also include a quantity of a reagent disposed within the device. The reagent may be a salt, a buffer, an enzyme, and the like. Reagents that are useful in an amplification reaction are considered especially suitable. Such reagents may be disposed within an area of the device in dried or liquid form. Reagents may also be disposed within the device within a well; fluid reagents may be preloaded into wells where the reagents remain until the device is used.

In one such embodiment, a sample is loaded into a first population of wells on a first component of a device. The device may also include a second population of wells on a second component of the device, the second population of wells being pre-filled with a reagent selected to react with the sample. Relative motion between the first and second components exposes at least some of the first population of wells to at least some of the second population of wells (e.g., FIG. 1), and the pre-stored reagent may then react with the sample in individual analysis regions formed from first and second wells exposed to one another.

The present disclosure provides other devices. These devices suitably include a first component comprising a population of first areas and a second component comprising a population of second areas, with the first and second components suitably being engageable with one another such that when the first and second components are in a first position relative to one another a fluidic path is formed between at least some of the first areas and at least some of the second areas. The devices are also suitably configured such that when the first and second components are in a second position relative to one another, the fluidic path is interrupted so as to isolate at least some of the first areas from at least some of the second areas.

One such exemplary embodiment is shown by FIG. 1. As shown in that figure, first and second components (well-bearing plates, in this figure) are engaged with one another (right side of panel A). In a first position (panels B and C), wells formed in the upper component (shown with dotted lines) and wells formed in the lower component (shown by solid lines) form a fluidic path, which path is shown by the fluid filling illustrated in panel C. The filling may be effected by an inlet (not shown in FIG. 1) that is formed in (or through) a component so as to connect a well of the component to the exterior of the device.

In a second position (shown in panel D), the fluidic path is interrupted by way of relative motion of the well-bearing components so as to isolate some of the wells that formerly defined the fluidic path from one another. In this way, the device allows a user to [1] introduce a material into multiple areas (e.g., wells) and then [2] isolate those areas from one another so as to allow processing of that material in individualized quantities. Suitable components and the characteristics of these components (e.g., wells, well volumes) are described elsewhere herein. It should be understood that the devices may include embodiments where two or more first areas may differ from one another in terms of volume. For example, a first component may include wells of 1 nL, 10 nL, and 100 nL formed therein. Likewise, the devices may include embodiments where two or more second areas may differ from one another in terms of volume. For example, a second component may include wells of 1 nL, 10 nL, and 100 nL formed therein. As shown by exemplary panel C of FIG. 1, the fluidic path may comprise at least one first area at least partially exposed to (e.g., overlapping with) at least one second area. The overlap between first and second areas may give rise to analysis regions, which analysis regions may (as described elsewhere herein) have different volumes from one another.

In some particularly suitable embodiments, the fluidic path is configured to permit the passage of aqueous media. This may be accomplished, for example, by placing a layer of material (e.g., lubricating fluid or oil) between the first and second components. As explained in the other documents cited herein, the layer of lubricating oil may act to isolate a well formed in the first component from other wells formed in the first component and also from wells formed in the second component, except when those wells are exposed (e.g., placed into at least partial register) to one another. The lubricating oil may be chosen such that it does not permit the passage of aqueous media. In some embodiments, the lubricating fluid may be mineral oil, tetradecane, long chain hydrocarbon, silicone oil, fluorocarbon, and the like, as well as combinations of the foregoing.

It should be understood that in some embodiments, an oil or other non-aqueous material may also be disposed within a well. This may be shown by reference to exemplary FIG. 1. In one embodiment, certain first and second wells may be filled with an aqueous material (panel C in FIG. 1). Other wells on the device that are not filled with the aqueous material may be filled with an oil (not shown). When the fluidic path between the aqueous-filled wells is broken (panels C and D), the aqueous-filled wells are exposed pairwise to wells that are filled with oil.

In some of devices, an analysis region may include an isolated first area or an isolated second area. In one such embodiment, the first component comprises wells formed therein and the second compartment comprises wells formed therein. The components may be positioned such that (e.g., FIG. 1, panel C) at least some of the first and second wells form a fluidic path. The components may then be positioned such that the fluidic path is interrupted and, further, that some of the first wells are (not shown) positioned opposite to a flat (i.e., non-well bearing) portion of the second component, and some of the second wells are positioned opposite to a flat (i.e., non-well bearing) portion of the first component. In other embodiments, an analysis region may comprise an isolated first area and an isolated second area that are exposed only to one another. This is shown by panel D of non-limiting FIG. 1.

Also provided are methods. These methods suitably include distributing one or more target molecules from an original sample into a plurality of analysis regions, the distribution being effected such that at least some of the analysis regions are statistically estimated to each contain a single target molecule. Embodiments where at least two of the analysis regions have different volumes from another are considered especially suitable. In some embodiments, the methods include effecting a reaction on at least some of the single target molecules. The reaction may take place in parallel, i.e., the reaction occurs on two or more target molecules at the same time. The reaction may be also performed in multiple analysis regions at the same time. It should be understood that different types reactions (e.g., amplification, lysing) may take place at the same time at different analysis regions.

The distribution may be effected by dividing an area within which one or more target molecules resides into at least two analysis regions. Panels C and D of FIG. 1 are illustrative of this aspect of the method. In panel C, a fluid containing one or more target molecules is introduced into a fluidic path that comprises, as described elsewhere herein, wells formed in first and second components. When the fluidic path is interrupted (panel D of FIG. 1), the fluid is subdivided into various analysis regions. The volumes of the analysis regions and the target-molecule containing fluid itself may be configured such that at least some of the analysis regions each contain (or at estimated to each contain) a single target molecule.

The user may also estimate the concentration of a target compound in the original sample. This estimation may be effected by application of most probable number theory, as described in Shen et al., JACS 2011 133: 17705-17712, Kreutz et al., Analytical Chemistry 2011 83: 8158-8168, and Shen et al., "Digital Isothermal Quantification of Nucleic Acids via Simultaneous Chemical Initiation of Recombinase Polymerase Amplification Reactions on SlipChip", Analytical Chemistry 2011 83:3533-3540. The estimation may be performed such that the estimation has a lower detection limit, at a 95% confidence value, of more than about 0.1 molecules/mL, and an upper level of quantification of less than about $10^{12}$ molecules/mL.

In some embodiments, the target molecule comprises a target nucleic acid, and the method is capable of estimating the concentration of the target nucleic acid in the original sample with at least about 3-fold resolution for original samples with concentrations of about 500 molecules or more of target nucleic acid per milliliter.

Nucleic acids and proteins are considered especially suitable target molecules. In some embodiments, the reaction is an amplification, such as a nucleic acid amplification. The amplification may be performed within 5, 10, 20, 50, 100, 500, or even 1000 analysis regions. The amplification may be performed in such a way that amplification occurs in at least two analysis regions at the same time, although it is not necessary that amplification begin or end at the same time in the different analysis regions. The amplification may be performed in an essentially isothermal manner such that the process takes place within a temperature range of plus or minus about 10 degrees C. For example, the amplification may take place at within 10 degrees C. of ambient conditions.

A variety of amplification techniques may be used, as described elsewhere herein. Some such suitably techniques include a polymerase chain reaction, a room-temperature polymerase chain reaction, a nested polymerase chain reaction, a multiplex polymerase chain reaction, an arbitrarily primed polymerase chain reaction, a nucleic acid sequence-based amplification, a transcription mediated amplification, a strand displacement amplification, a branched DNA probe target amplification, a ligase chain reaction, a cleavase invader amplification, an anti DNA-RNA hybrid antibody amplification, and the like.

An analysis region may, as described elsewhere herein, comprise first and second areas in pairwise exposure with one another. The user may effect relative motion between a first component comprising a plurality of first areas and a second component comprising a plurality of second areas, the relative motion placing at least one first area and at least one second area into pairwise exposure with one another to define at least one analysis region. This is illustrated in FIG. 1, panels C and D, where first and second areas are placed into pairwise exposure with one another so as to define analysis regions. The relative motion may place at least about 10 first areas into pairwise exposure with at least about 10 second areas, or may even place at least about 100 first areas into pairwise exposure with at least about 100 second areas.

The instant disclosure also provides methods. These methods include introducing an amount of a target molecule from an original sample into a device; effecting distribution of the amount of the target molecule into at least two isolated areas of the device, the at least two isolated areas defining volumes that differ from one another; effecting a reaction on the target molecule so as to give rise to a reaction product in the at least two isolated areas; and estimating, from the reaction product, the level of target molecule in the original sample.

The target molecule may be, for example, a nucleic acid. The methods may also include contacting an amplification reagent—such as a reagent useful in PCR—with the nucleic acid. In some embodiments, at least one isolated area is estimated to contain one nucleic acid molecule, as described elsewhere herein. One particularly suitable reaction to perform within the disclosed methods is nucleic acid amplification; suitable amplification techniques are described elsewhere herein. The nucleic acid amplification may be essentially isothermal, as described elsewhere herein.

The methods may also include estimating the level of a nucleic acid in the original sample. In some embodiments, at least one of the isolated areas is estimated to comprise about one molecule of nucleic acid. This facilitates application of the estimation methods described in Kreutz et al., JACS 2011 133: 17705-17712; Kreutz et al., Anal. Chem. 2011 83: 8158-8168; and Shen et al., Anal. Chem. 2011 83: 3533-3540. The disclosed methods may be capable of estimating the concentration of target nucleic acid in the original sample with at least about 3-fold resolution for original samples with concentrations of about 500 molecules or more of target nucleic acid per milliliter.

An isolated area, e.g., a well, may suitably have a volume in the range of from about 1 picoliter to about 10 microliters, as described elsewhere herein. Volumes in the range of from about 1 nL to about 500 nL, or even from about 5 nL to about 100 nL are considered suitable.

Distribution of some amount of target molecules may be effected by effecting relative motion between a first and second component so as to distribute the amount of the target molecule into at least two isolated areas, as described elsewhere herein and as shown by exemplary FIG. 1 panels B-D. The relative motion may give rise to the amount of the target molecule being divided among at least 10 isolated areas, or even among at least 50 isolated areas.

According to the disclosed methods, a reaction may be effected at two or more areas essentially simultaneously. The reactions need not necessarily (but can be) the same in two or more areas. For example, a user may effect an amplification reaction at three areas while effecting a different reaction (e.g., denaturing) at three other areas.

Other disclosed methods include distributing a plurality of target molecules from an original sample into a plurality of analysis regions, the distribution being effected such that at least some of the analysis regions are estimated to each contain a single target molecule, and at least two of the analysis regions defining different volumes; effecting, in parallel, a nucleic acid amplification reaction on at least some of the single target molecules. Suitable amplification techniques are described elsewhere herein. The amplification may, in some embodiments, be effected essentially isothermally.

In some embodiments, the methods further include removing a product of the nucleic acid amplification reaction. Such recovery may be carried out, in some embodiments, by accessing individual wells of a device. In some embodiments, recovery is achieved by combining material from multiple wells, for example by placing a device into the loading position and using a carrier fluid (including a gas) to expel the material from the device. Recovery may also be accomplished by pipetting material out of a device. Such recovery may be used for additional analysis of nucleic acid products, such as sequencing, genotyping, analysis of methylation patterns, and identification of epigenetic markers.

Recovered material may be removed from the device. In some embodiments, recovered material may be transferred to another device, or another region of the same device. Amplification may be carried out by the methods described herein or by other methods known in the art or by their combinations. As one non-limiting example, a user may detect the presence of a target nucleic acid, e.g., by PCR. Once the presence of the target is confirmed, the user may remove the product from the device. This may be accomplished by pipetting the product out of an individual well and transferring that product to another device or container. The recovered product may be further processed, e.g., sequenced. A variety of sequencing methods are known to those of ordinary skill in the art, including Maxam-Gilbert sequencing, chain-termination sequencing, polony sequencing, 454 sequencing™, SOLiD sequencing™, ion semiconductor sequencing, nanoball sequencing, Helioscope™ sequencing, nanopore sequencing, single-molecule SMRT™ sequencing, single molecule real time sequencing (RNAP), and the like.

The present disclosure also provides devices. These devices include a first component comprising a population of first wells formed in a first surface of the first component, the population of wells being arranged in a radial pattern; a second component comprising a population of second wells formed in a first surface of the second component, the plurality of wells being arranged in a radial pattern; the first and second components being engageable with one another such that relative rotational motion between the first and second components exposes at least some of the first population of wells to at least some of the second population of wells so as to form a plurality of analysis regions, an analysis region comprising a first well and a second well in pairwise exposure with one another.

In some embodiments, at least two analysis regions have volumes that differ from one another, as described elsewhere herein. The first component may include a channel having an inlet, the channel configured so as to place at least some of the first wells into fluid communication with the environment exterior to the channel. The inlet may reside in a surface of the first component other than the surface of the first component in which the first wells are formed. In this way, when the two components are assembled together such that the wells of the first component face the wells of the second component, the user may fill the wells of the first component without dissembling the device.

It should be understood that the second component may also include a channel and inlet, configured such that the channel inlet is formed in a surface of the second component other than the surface of that component in which the wells reside.

The devices may include, e.g., from about 10 to about 10,000 first wells. The devices may also include, e.g., from about 10 to about 10,000 second wells.

The disclosed methods may further include estimating the level, presence, or both of the one or more nucleic acids in the biological sample. Estimating may comprise (a) estimating the presence or absence of the one or more nucleic acids in two or more wells of different volumes and (b) correlating the estimated presence or absence of the one or more nucleic acids in the two or more wells of different volumes to a level of the one or more nucleic acids in the biological sample, or, alternatively, to the level of some other target in a biological sample or even in a subject. Exemplary estimation methods are described elsewhere herein.

The present disclosure provides estimating the level of a target present in a sample (e.g., estimating viral load in a subject by determining the presence or concentration of a nucleic acid marker in a sample). The present disclosure, however, also provides detecting the presence of a target in a sample so as to provide the user with a yes/no determination concerning whether a particular analyte is present in a subject. In these embodiments, the user may perform a reaction (e.g., amplification, labeling) on a sample and merely assay for the presence of a "positive" result of the reaction.

One estimation method is provided in Kreutz et al., Anal. Chem. 2011 83: 8158-8168. As explained in that publication, theoretical methods may be used—in conjunction with software analysis tools—to design and analyze multivolume analysis devices. Multivolume digital PCR ("MV digital PCR") is a reaction that is especially amenable to these methods. MV digital PCR minimizes the total number of wells required for "digital" (single molecule) measurements while also maintaining high dynamic range and high resolution.

As one illustrative example, a multivolume device having fewer than 200 total wells is predicted to provide dynamic range with a 5-fold resolution. Without being bound to any particular theory, this resolution is similar to that of single-volume designs that use approximately 12,000 wells.

Mathematical techniques, such as application of the Poisson distribution and binomial statistics, may be used to process information obtained from an experiment and to quantify performance of devices. These techniques were experimentally validated using the disclosed devices.

MV digital PCR has been demonstrated to perform reliably, and results from wells of different volumes agreed with one another. In using the devices, no artifacts due to different surface-to-volume ratios were observed, and single molecule amplification in volumes ranging from 1 to 125 nL was self-consistent.

An exemplary device according to the present disclosure was constructed to meet the testing requirements for measuring clinically relevant levels of HIV viral load at the point-of-care (in plasma, <500 molecules/mL to >1,000,000 molecules/mL). The predicted resolution and dynamic range was experimentally validated using a control sequence of DNA, as described in Kreutz et al., Anal. Chem. 2011 83: 8158-8168.

The estimation theory applied in the above publication may be summarized as follows. First, there are two assumptions that are maintained: (1) having at least one target molecule in a well is necessary and sufficient for a positive signal, and (2) target molecules do not interact with one another or device surfaces, to avoid biasing their distribution. At the simplest level of analysis, when molecules are at low enough densities that there is either 0 or 1 molecule within a well, concentrations can be estimated simply by counting wells displaying a "positive" signal. Under the above assumptions, Poisson and binomial statistics may be used to obtain quantitative results from experiments resulting in one positive well to experiments resulting in one negative well. The Poisson distribution (eq. 1), in the context of digital PCR, gives the probability, p, that there are k target molecules in a given well based on an average concentration per well, $v \cdot \lambda$, where v is the well volume (mL) and $\lambda$ is the bulk concentration (molecules/mL). In digital PCR, the same readout occurs for all k>0, so if k=0, then eq. 1 simplifies to give the probability, p, that a given well will not contain target molecules (the well is "negative").

$$p=(v \cdot \lambda)^k e^{-(v \cdot \lambda)}/k!, \text{ And for k=0(empty well)},$$
$$p=e^{-(v \cdot \lambda)} \quad (1)$$

In single-volume systems, the number of negative wells, b, out of total wells, n, can serve as an estimate for p, so expected results can be estimated from known concentrations, or observed results can be used to calculate expected concentrations (eq. 2).

$$b = n \cdot e^{-(v \cdot \lambda)} \text{ or } \lambda = -\ln(b/n)/v \quad (2)$$

The binomial equation is used to determine the probability, P, that a specific experimental result (with a specific number of negatives, b, and positives, n−b, out of the total number of wells, n, at each volume) will be observed, on the basis of $\lambda$ (eq. 3), $$\text{Where } \binom{n}{b} = \frac{n!}{b!(n-b)!} \quad (3)$$

$$P = \binom{n}{b} \cdot p^b \cdot (1-p)^{n-b} \text{ or}$$

$$P = \binom{n}{b} \cdot (e^{-v \lambda})^b \cdot (1-e^{-v \lambda})^{n-b}$$

An incomplete analysis of multivolume systems may be performed by simply selecting a single volume and analyzing it as described above; this is the approach that has typically been taken in serial dilution systems. The single volume that minimizes the standard error is generally chosen; this typically occurs when 10-40% of wells are negative. This method, however, does not utilize the information from the other "dilutions" (or volumes), and would require using different dilutions for different sample concentrations. Combining the results from wells of different volumes fully minimizes the standard error and provides high-quality analysis across a very large dynamic range. This is achieved by properly combining the results of multiple binomial distributions (one for each volume); specifically, the probability of a specific experimental result P (defined above) is the product of the binomials for each volume (eq. 4), where P is defined as a function of the bulk concentration $\lambda$, $P=f(\lambda)$, $$f(\lambda) = P = \prod \binom{n_i}{b_i} \cdot (e^{-v_i \lambda})^{b_i} \cdot (1 - e^{-v_i \lambda})^{n_i - b_i} \quad (4)$$

For a given set of results, the MPN is found by solving for the value of $\lambda$ that maximizes P. In general, taking the derivative of an equation and solving for zero provides the maximum and/or minimum values of that equation; as a binomial distribution (and subsequently the product of binomials) has only a single maximum, solving the derivative of eq. 4 for zero provides the "most probable" concentration. The standard deviation, $\sigma$, is more appropriately applied to ln ($\lambda$) than to $\lambda$, because the distribution of P based on ln ($\lambda$) is more symmetrical than that for $\lambda$. In addition, this approach provides better accuracy for low concentrations by enforcing the constraint that concentrations must be positive. Thus, a change of variables is needed during the derivations so $\sigma$ can be found for ln ($\lambda$). Therefore, $f(\lambda)$ (eq. 4) is converted to $F(\Lambda)$ (eq. 5), where $\theta = e^{-v}$ and $\Lambda = \ln(\lambda)$.

$$F(\Lambda) = P = \prod \binom{n_i}{b_i} \cdot (\theta_i^{e^\Lambda})^{b_i} \cdot (1 - \theta_i^{e^\Lambda})^{n_i - b_i} \quad (5)$$

The derivative is easier to handle if the natural log is applied to eq. 5, as the individual components are separated, but the overall result is unchanged (eq. 6).

$$L(\Lambda) = \ln F(\Lambda) = \sum_{i=1}^{m} \left( \ln\binom{n_i}{b_i} + b_i \cdot e^{\Lambda} \cdot \ln(\theta_i) + (n_i - b_i) \cdot \ln\left(1 - \theta_i^{e^{\Lambda}}\right) \right) \quad (6)$$

The first derivative is then $$\frac{\partial L(\Lambda)}{\partial \Lambda} \sum_{i=1}^{m} \left( 0 + b_i \cdot e^{\Lambda} \cdot \ln(\theta_i) - \frac{(n_i - b_i) \cdot e^{\Lambda} \cdot \theta_i^{e^{\Lambda}}}{1 - \theta_i^{e^{\Lambda}}} \cdot \ln(\theta_i) \right)$$

ln ($\theta_i$) can be replaced with $v_i$:

$$= e^{\Lambda} \cdot \sum_{i=1}^{m} \left( -b_i \cdot v_i + \frac{(n_i - b_i) \cdot v_i \cdot \theta_i^{e^{\Lambda}}}{\left(1 - \theta_i^{e^{\Lambda}}\right)} \right)$$

substituting ($n_i t_i$) for $b_i$ (where $t_i$ is the number of positive wells):

$$= e^{\Lambda} \cdot \sum_{i=1}^{m} \left( -n_i \cdot v_i + t_i \cdot v_i + \frac{t_i \cdot v_i \cdot \theta_i^{e^{\Lambda}}}{\left(1 - \theta_i^{e^{\Lambda}}\right)} \right)$$

rearranging to put all $t_i$'s over the denominator $$= e^{\Lambda} \cdot \sum_{i=1}^{m} \left( -n_i \cdot v_i + \frac{t_i \cdot v_i}{\left(1 - \theta_i^{e^{\Lambda}}\right)} - \frac{t_i \cdot v_i \cdot \theta_i^{e^{\Lambda}}}{\left(1 - \theta_i^{e^{\Lambda}}\right)} + \frac{t_i \cdot v_i \cdot \theta_i^{e^{\Lambda}}}{\left(1 - \theta_i^{e^{\Lambda}}\right)} \right)$$

and simplifying and rearranging in terms of $b_i$ $$\left[ \frac{\partial L(\Lambda)}{\partial \Lambda} = e^{\Lambda} \cdot \sum_{i=1}^{m} \left( -n_i \cdot v_i + \frac{(n_i - b_i) \cdot v_i}{\left(1 - \theta_i^{e^{\Lambda}}\right)} \right) \right] \quad (7)$$

Setting eq. 7 equal to 0, re-substituting λ, and rearranging then gives eq. 8. By solving eq. 8 for λ, the expected concentration can be determined from the number of empty wells. This can be done using any solver function; the code MVdPCR_MLE.m (described in Kreutz et al., Analytical Chemistry 2011 83: 8158-8168) performs this step using a globalized Newton method.

$$\sum_{i=1}^{m} n_i \cdot v_i = \sum_{i=1}^{m} \frac{(n_i - b_i) \cdot v_i}{(1 - e^{-v_i \cdot \lambda})} \quad (8)$$

The standard error, σ, for a result can be found using the Fisher information, I(X), for ln(λ), 44 requiring the change of variable to Λ. The Fisher information is defined in eq. 9, where E[ ] represents the expected value of the given variable.

$$\frac{1}{\text{variance}} + \frac{1}{\sigma^2} = I(\Lambda) = -\int \frac{\partial^2 L(\Lambda)}{\partial \Lambda^2} f(x; \theta) dx = E\left[ -\frac{\partial^2 L(\Lambda)}{\partial \Lambda^2} \right] \quad (9)$$

In eq. 10, the second derivative of eq. 6 is found.

$$\frac{\partial^2 L(\Lambda)}{\partial \Lambda^2} = e^{\Lambda} \cdot \sum_{i=1}^{m} \left( -n_i \cdot v_i + \frac{(n_i - b_i) \cdot v_i}{\left(1 - \theta_i^{e^{\Lambda}}\right)} \right) + \quad (10)$$

$$e^{\Lambda} \cdot \sum_{i=1}^{m} \left( \frac{e^{\Lambda} \cdot (n_i - b_i) \cdot \theta_i^{e^{\Lambda}} \cdot v_i \cdot (\ln \theta)}{\left(1 - \theta_i^{e^{\Lambda}}\right)^2} \right) =$$

$$e^{\Lambda} \sum_{i=1}^{m} \left( n_i \cdot v_i - \frac{(n_i - b_i) \cdot v_i}{\left(1 - \theta_i^{e^{\Lambda}}\right)} \right) - (e^{\Lambda})^2 \cdot \sum_{i=1}^{m} \left( \frac{(n_i - b_i) \cdot v_i^2 \cdot \theta_i^{e^{\Lambda}}}{\left(1 - \theta_i^{e^{\Lambda}}\right)^2} \right)$$

Using this expression in eq. 9 to then find the inverse variance gives eq. 11

$$\frac{1}{\sigma^2} = -E\left[ e^{\Lambda} \cdot \sum_{i=1}^{m} \left( n_i \cdot v_i - \frac{(n_i - b_i) \cdot v_i}{\left(1 - \theta_i^{e^{\Lambda}}\right)} \right) - \right. \quad (11)$$

$$\left. (e^{\Lambda})^2 \cdot \sum_{i=1}^{m} \left( \frac{(n_i - b_i) \cdot v_i^2 \cdot \theta_i^{e^{\Lambda}}}{\left(1 - \theta_i^{e^{\Lambda}}\right)^2} \right) \right]$$

$$= -e^{\Lambda} \sum_{i=1}^{m} \left( n_i \cdot v_i - \frac{(n_i - E[b_i]) \cdot v_i}{\left(1 - \theta_i^{e^{\Lambda}}\right)} \right) +$$

$$(e^{\Lambda})^2 \cdot \sum_{i=1}^{m} \left( \frac{(n_i - E[b_i]) \cdot v_i^2 \cdot \theta_i^{e^{\Lambda}}}{\left(1 - \theta_i^{e^{\Lambda}}\right)^2} \right)$$

With E[$b_i$] coming from eq. 2

$$= -e^{\Lambda} \sum_{i=1}^{m} \cdot \left( n_i \cdot v_i - \frac{\left(n_i - n_i \cdot \theta_i^{e^{\Lambda}}\right) \cdot v_i}{\left(1 - \theta_i^{e^{\Lambda}}\right)} \right) +$$

$$(e^{\Lambda})^2 \cdot \sum_{i=1}^{m} \left( \frac{\left(n_i - n_i \cdot \theta_i^{e^{\Lambda}}\right) \cdot v_i^2 \cdot \theta_i^{e^{\Lambda}}}{\left(1 - \theta_i^{e^{\Lambda}}\right)^2} \right)$$

$$= -e^{\Lambda} \sum_{i=1}^{m} \cdot \left( n_i \cdot v_i - n_i \cdot v_i \cdot \frac{\left(1 - \theta_i^{e^{\Lambda}}\right)}{\left(1 - \theta_i^{e^{\Lambda}}\right)} \right) +$$

$$(e^{\Lambda})^2 \cdot \sum_{i=1}^{m} \left( \frac{n_i \cdot \left(1 - \theta_i^{e^{\Lambda}}\right) \cdot v_i^2 \cdot \theta_i^{e^{\Lambda}}}{\left(1 - \theta_i^{e^{\Lambda}}\right)^2} \right)$$

$$= (e^{\Lambda})^2 \cdot \sum_{i=1}^{m} \left( \frac{n_i \cdot v_i^2 \cdot \theta_i^{e^{\Lambda}}}{\left(1 - \theta_i^{e^{\Lambda}}\right)} \right) = \lambda^2 \cdot \sum_{i=1}^{m} \left( \frac{n_i \cdot v_i^2 \cdot e^{-v_i \cdot \lambda}}{\left(1 - e^{-v_i \cdot \lambda}\right)} \right)$$

$$= \lambda^2 \cdot \sum_{i=1}^{m} \left( \frac{n_i \cdot v_i^2}{\left(e^{v_i \cdot \lambda} - 1\right)} \right)$$

This ultimately gives the standard error (eq. 12), from which confidence intervals can be generated (eq. 13), where Z is the upper critical value for the standard normal distribution.

$$\sigma = \frac{1}{\sqrt{\lambda^2 \cdot \Sigma \frac{v_i^2 \cdot n_i}{e^{v_i \cdot \lambda} - 1}}} \lambda^2. \quad (12)$$

$$CI = \ln(\lambda) \pm Z \cdot \sigma \quad (13)$$

One aspect of the disclosed devices achieves a certain resolution (that is, to distinguish a certain difference in concentration) at certain concentrations. As mentioned above for HIV viral load monitoring, a system suitably achieves a 3-fold resolution for as low as 500 molecules/mL. To correctly resolve two different concentrations, the potential for false positives (Type I error) and false negatives (Type II error) may be considered. Samples suitably give results at the desired confidence level (1-α, measure of Type I error) and demonstrate this confidence level again and again (Power: 1-β, measure of Type II error).

When comparing two results, the null hypothesis is that the results come from samples that have statistically the same concentration. α is the probability that two results that are determined to be statistically different are in fact from the same sample, thus resulting in a false positive. A 95% confidence level would correspond to α=0.05 and an accepted false positive rate of 5%. The power level measures the probability, β, that samples that are statistically different at the desired confidence level give results that fall below this confidence level. A 95% power level would correspond to β=0.05 and thus an accepted false negative rate of 5%. For the exemplary analysis described herein, the 3-fold resolution is defined such that samples with a 3-fold difference in concentration (e.g., 500 and 1500 molecules/mL) gives results that are statistically different with at least 95% confidence (α<0.05, less than 5% false positives) at least 95% of the time (power level of 95%, β<0.05, no more than 5% false negatives). The Z-test (eq. 14) was chosen to measure the confidence level, where λ and σ are calculated using eqs. 8 and 12, respectively, for a set of two results (the specific number of negatives, $b_i$ out of the total number of wells, $n_i$, at each volume i of wells). The Z-test measures the probability that results are statistically different, by assuming that the test statistics (left side of eq. 14) can be approximated by a standard normal distribution, so Z corresponds to a known probability. Power level is measured by simulating results from two different samples and determining the probability that they will give results that at least meet the desired confidence level.

$$\frac{\lambda_1 - \lambda_2}{\sqrt{\sigma_{12} + \sigma_{22}}} = Z, \text{ for 95\% confidence } \frac{\lambda_1 - \lambda_2}{\sqrt{\sigma_{12} + \sigma_{22}}} > 1.96 \quad (14)$$

Figure 14:
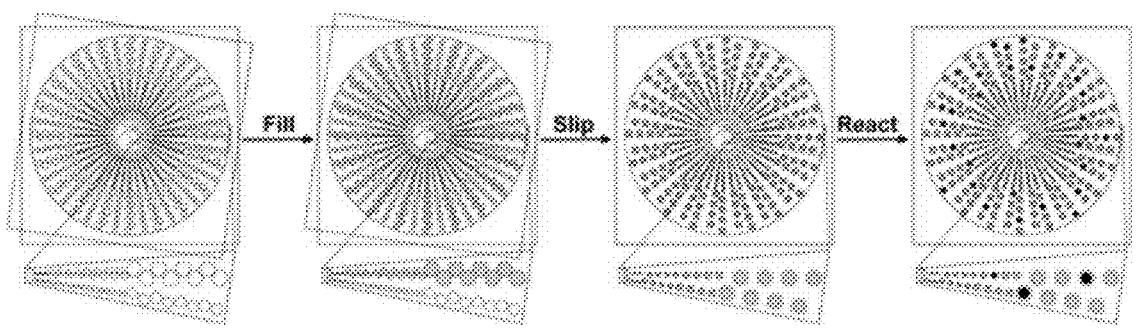
FIG. 14 presents a schematic view of a radially-arranged device for performing MV digital PCR, the device design consisting of 160 wells each at 125, 25, 5, and 1 nL. A sample is loaded from the center and after filling the device components are relatively rotated so as to isolate wells—after reaction, wells containing template have enhanced signal and are counted.
Figure 15:
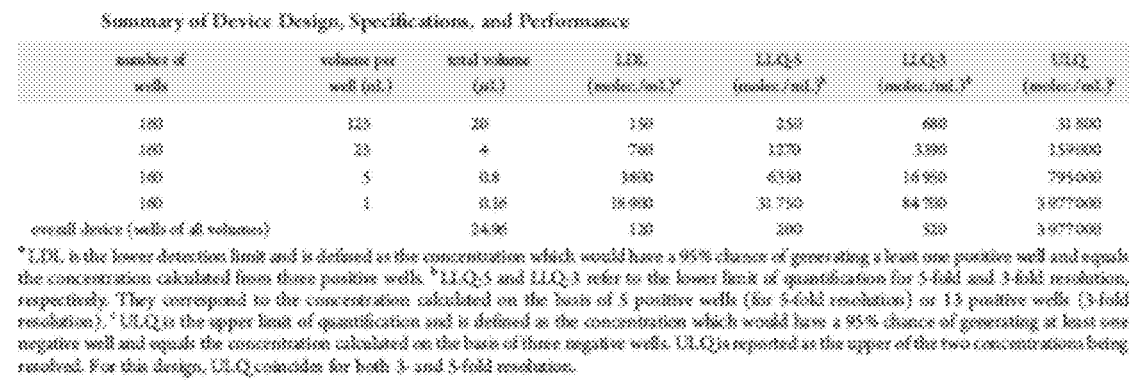
Figure 16:
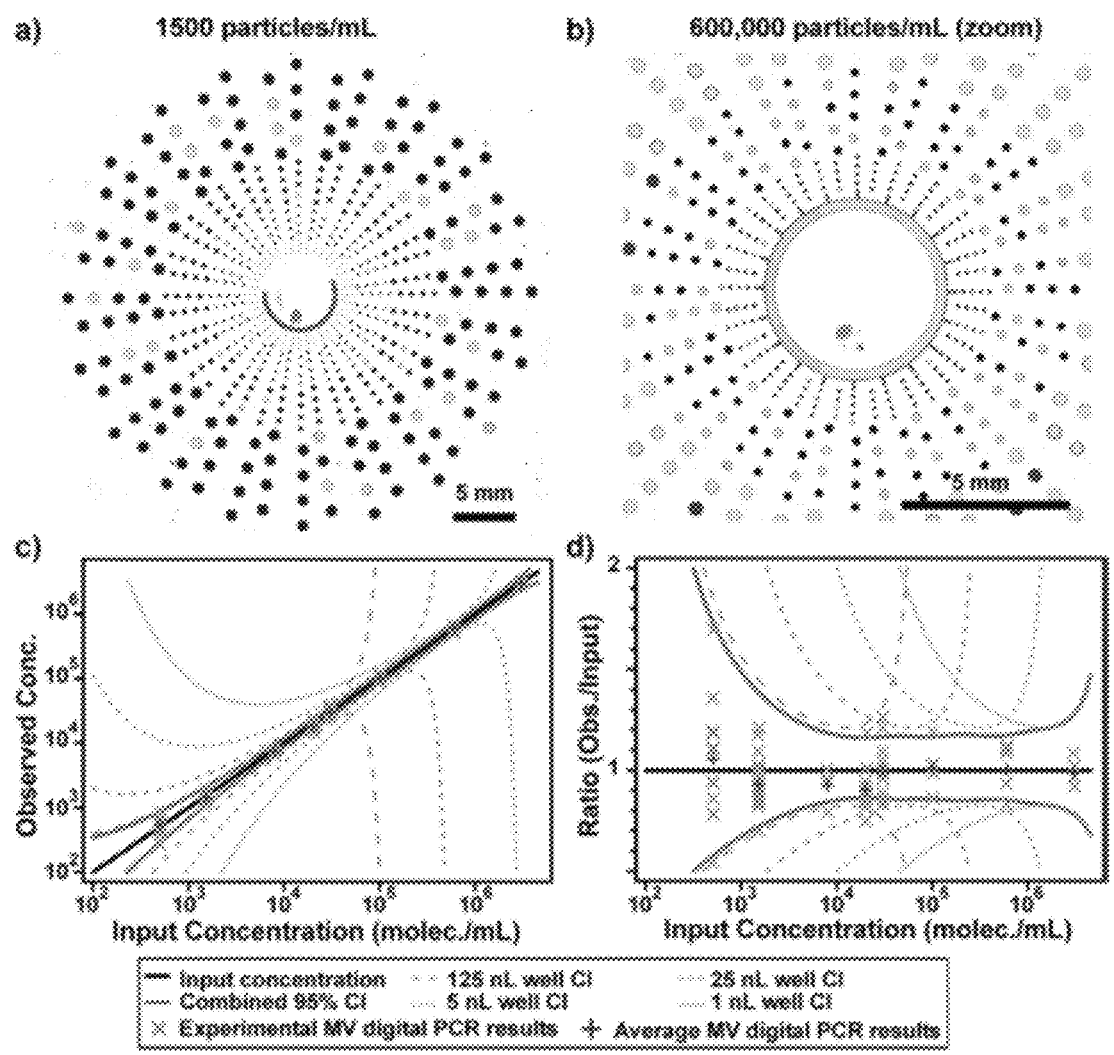
FIG. 16 presents experimental results for MV digital PCR on an exemplary device using control DNA. Representative false color (shaded) images (lighter shading represents positive wells that showed at least a 3-fold increase in intensity compared to negative wells) for solutions with input concentrations of (a) 1500 molecules/mL and (b) 600,000 molecules/mL (zoomed in on smaller wells). (c, d) Graphical summary of all experiments comparing the input concentration, based on UV-vis measurements (black curve), and observed concentrations using MV digital PCR (× and +) over the entire dynamic range. Represented as (c) the actual concentration and (d) as a ratio to better show distribution of results. Stock samples were approximately 500, 1500, 8000, 20,000, 30,000, 100,000, 600,000, and 3,000,000 molecules/mL. The confidence intervals (CI) for the combined system (solid curves) indicate where 95% of the experiments should fall. CI curves for the individual volumes (dashed curves) are also provided to indicate over what range of concentration each volume contributes.

A multivolume device was designed with 160 wells each at volumes of 125, 25, 5, and 1 nL (FIG. 15). A radial layout of wells (FIG. 14) provides an efficient use of space when wells of significantly different volumes are used. In the initial orientation of the radial multivolume device, the wells are aligned to create a continuous fluidic path that allows all of the sample wells to be filled in one step using dead end filling. The components of the device can then be rotationally slipped or translated (by ~8°) to simultaneously isolate each well and also overlap the well with an optional corresponding thermal expansion well (FIG. 14). This device has a LDL of 120 molecules/mL and a dynamic range where at least 3-fold resolution is achieved from 520 to 3,980,000 molecules/mL (FIG. 15). A control 631 bp sequence of DNA was used to validate the MV digital PCR approach. The initial concentration of this stock solution was determined by UV-vis, and the stock was then diluted to levels required for testing of the chip. Concentrations were tested across the entire dynamic range of the device: approximately 500, 1500, 8000, 20,000, 30,000, 100,000, 600,000, and 3,000,000 molecules/mL. A total of 80 experiments and 29 additional controls were performed, and the observed concentrations showed excellent agreement with the expected concentrations and demonstrated the accuracy of the device performance over the entire dynamic range (FIG. 16). The experimental results consist of a "digital" pattern of positive and negative wells. At an input concentration of 1500 molecules/mL (FIG. 3*a*), the larger 125 and 25 nL wells provide the majority of the information to determine the concentration. As expected, at a higher concentration of 600,000 molecules/mL, positives were found in the smaller 5 and 1 nL wells also (FIG. 16*b*), and these smaller wells provide the majority of the information used to determine the concentration. Excellent agreement was found between the input concentration and the measured concentration over 4 orders of magnitude (FIG. 16*c, d*). In this multivolume design, the 95% confidence interval is narrow at a consistent level over a very large range of concentrations: the CI is within 13.8-15% of the expected value from 9500 to 680,000 molecules/mL and within 13.8-17.5% from 5400 to 1,700,000 molecules/mL. The experimental data closely tracked the theoretically predicted CI (FIG. 16*d*).

Figure 17:
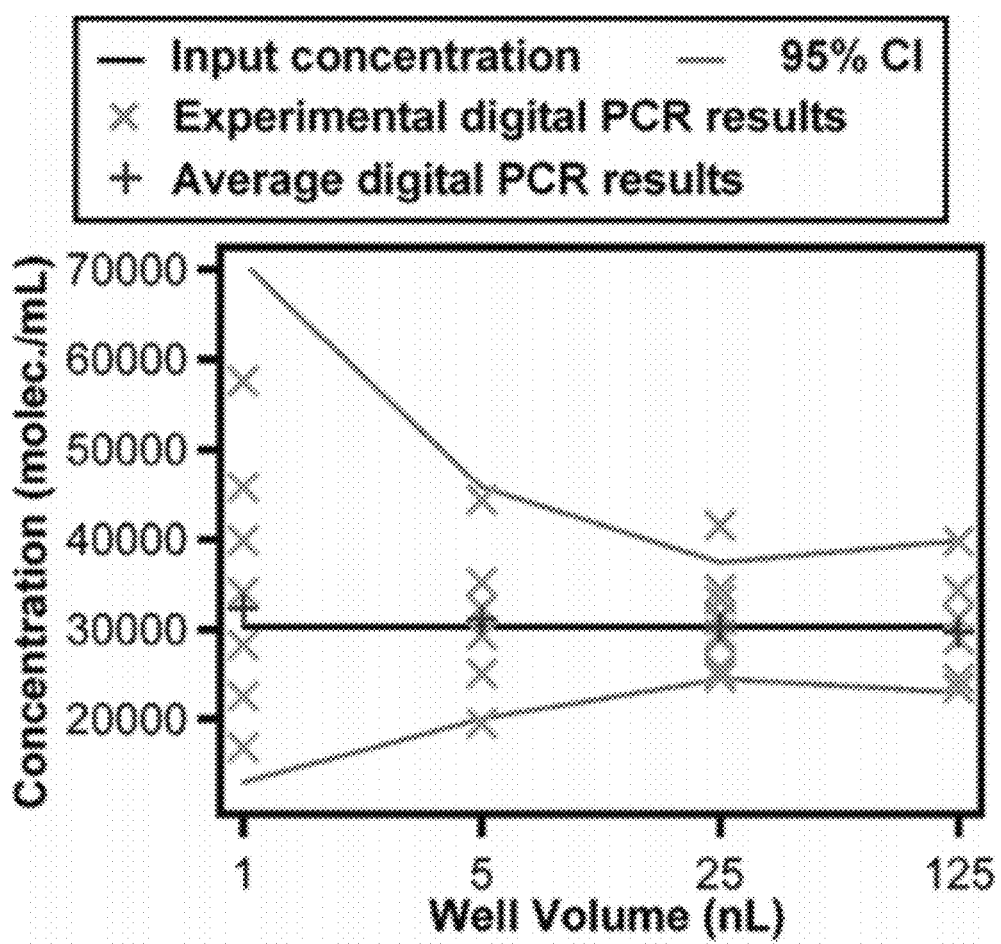
FIG. 17 illustrates a separate analysis of 10 experimental results for different well volumes with an input concentration of 30,000 molecules/mL, showing distribution of measured concentrations for each volume and the overall agreement of results.

As expected, the largest wells (125 nL) provided the largest contribution to the overall confidence interval for samples in the $10^2$-$10^4$ molecules/mL range while the use of smaller and smaller wells down to 1 nL in volume extended the dynamic range with a 95% confidence interval above $10^6$ molecules/mL (FIG. 16*c, d*). For each concentration, there was excellent agreement among the individual results obtained from the wells of different volumes, consistent with the accuracy of the overall device. This agreement is illustrated for an input concentration of 30,000 molecules/mL (FIG. 17). At this concentration, the wells of all volumes provided a reasonable number of positives and negatives for quantification, and we found that the concentration calculated from the results fell within the 95% confidence intervals for individual volumes of wells (38 of 40 results), and also, the averages from wells of each volumes were internally consistent (FIG. 17).

The estimation may, in some embodiments, have a lower detection limit, at a 95% confidence value, in the range of between about 40 molecules/mL sample to about 120 molecules/mL of sample. The methods may suitably be capable of resolving a three-fold difference in viral load of the biological sample based on an estimate of the level of the one or more nucleic acids.

In other embodiments, the methods include estimating the level, presence, or both of a protein in the biological sample. This estimation may be effected by (a) contacting the sample with a detection moiety capable of binding to the protein so as to give rise to a population of labeled proteins, the detection moiety comprising the one or more nucleic acids, (b) disposing the labeled proteins into two or more wells of different volumes, (c) amplifying the one or more nucleic acids of the detection moiety in the two or more wells of different volumes, and (d) correlating an estimated presence or absence of the one or more nucleic acids in the two or more wells of different volumes to a level of the protein in the biological sample.

As one example, anti-PSA capture antibody coated fluorescent magnetic beads are used to capture the target PSA molecule. The concentration of PSA may be controlled so there was less than one molecule on one bead. A dsDNA tag is attached to an anti-PSA detection antibody and used as signal probe. After incubation between antibodies and antigen, magnetic beads with captured/labeled PSA are loaded into pL wells with PCR supermix. Each well contains either one or no bead. After amplification, only wells containing beads are counted. The ratio between "on" wells and the total number of wells is used to determine the concentration of target.

As explained above, relative motion between first and second components effects distribution of any contents of the population of first wells between the first population of wells and an additional population of wells. The relative motion may effect distribution of any contents of the population of second wells between the second population of wells and an additional population of wells.

It should be understood that the methods may include one, two, or more applications of relative motion between components. For example, a first relative motion (e.g., rotation) may be applied so as to place first and second sets of wells into fluid communication with one another. After the contents of the first and second wells contact one another, additional rotation may be applied to place the wells with mixed contents into fluid communication with another set of wells with different contents, which in turns enables the user to effect processes that require separate and/or sequential mixing steps of two, three, or more sample volumes. This may be done, for example, to (1) mix materials in well A and well B in well A; and then (2) to contact the mixed materials in well A with a buffer in well C so as to dilute the contents of well A. Alternatively, the mixed contents of well A may be contacted (via relative motion of components) with well C such that the contents of well C may react with the contents of well A (which well included the contents of well A and well B).

Also provided are kits. The kits suitably include device as set forth elsewhere herein, and also a supply of a reagent selected to participate in nucleic acid amplification. The reagent may be disposed in a container adapted to engage with a the conduit of the first component, the conduit of the second component, or both. Such a container may be a pipette, a syringe, and the like.

The disclosed devices and kits may also include a device capable of supplying or removing heat from the first and second components. Such devices include heaters, refrigeration devices, infrared or visible light lamps, and the like. The kits may also include a device capable of collecting an image of at least some of the first population of wells, the second population of wells, or both.

Amplification Techniques

A non-exclusive listing of suitable isothermal amplification techniques are provided below. These techniques are illustrative only, and do not limit the present disclosure.

A first set of suitable isothermal amplification technologies includes NASBA, and RT-RPA. These amplification techniques can operate at 40 deg. C. (a lower temperature preferred for certain POC devices): NASBA (product: RNA), RT-RPA (product: DNA), RT-LAMP using one of LAMP HIV-RNA 6-primer sets, transcription-mediated amplification (TMA, 41 deg. C.), helicase dependent amplification (HAD, 65 deg. C.), and strand-displacement amplification (SDA, 37 deg. C.), In addition to standard PCR techniques, the disclosed methods and devices are also compatible with isothermal amplification techniques such as loop-mediated amplification (LAMP), Recombinase polymerase amplification (RPA), nucleic acid sequence based amplification (NASBA), transcription-mediated amplification (TMA), helicase-dependent amplification (HAD), rolling circle amplification (RCA), and strand-displacement amplification (SDA). The disclosed multivolume devices can be used to digitize such platforms.

Other isothermal amplification methods are also suitable. Isothermal exponential amplification reaction (EXPAR) may amplify a 10-20 bp trigger oligonucleotide generated from a genomic target more than 106 times in less than 10 minutes at 55 deg. C. by repeating cycles of polymerase and endonuclease activity, and has been coupled with DNA-functionalized gold nanospheres for the detection of herpes simplex virus. Isothermal and chimeric primer-initiated amplification of nucleic acids (ICANs) amplify target DNA at 55 deg. C. using a pair of 50-DNA-RNA-30 primers and the activity of RNase H and strand displacing polymerase.

Signal-mediated amplification of RNA technology (SMART) produces copies of an RNA signal at 41 deg. C. in the presence of an RNA or DNA target by way of the three-way junction formed between the target and two probes, one of which contains the RNA signal sequence and a T7 promoter sequence for T7 RNA polymerase. The single stranded RNA product may be detected by hybridization-based methods and because the signal is independent of the target, SMART may be used for detection of different target sequences. Cyclic enzymatic amplification method (CEAM) detects nucleic acids in the picomolar range in less than 20 minutes at 37 deg. C. using a displacing probe and Exonuclease III (Exo III) to generate amplification of fluorescent signal in the presence of a target. Isothermal target and signaling probe amplification (iTPA) combines the principle of ICAN and the inner-outer probe concept of LAMP along with fluorescence resonance energy transfer cycling probe technology (FRET CPT) for simultaneous target and signal amplification in 90 minutes at 60 deg. C., and has been shown to detect *Chlamydia trachomatis* at single copy level.

Other suitable amplification methods include ligase chain reaction (LCR); amplification methods based on the use of Q-beta replicase or template-dependent polymerase; helicase-dependent isothermal amplification; strand displacement amplification (SDA); thermophilic SDA nucleic acid sequence based amplification (3SR or NASBA) and transcription-associated amplification (TAA).

Non-limiting examples of PCR amplification methods include standard PCR, AFLP-PCR, Allele-specific PCR, Alu-PCR, Asymmetric PCR, Biased Allele-Specific (BAS) Amplification, Colony PCR, Hot start PCR, Inverse PCR (IPCR), In situ PCR (ISH), Intersequence-specific PCR (ISSR-PCR), Long PCR, Multiplex PCR, Nested PCR, Quantitative PCR, Reverse Transcription PCR (RT-PCR), Real Time PCR, Single cell PCR, Solid phase PCR, Universal Size-Specific (USS-PCR), branched-DNA technology, and the like Further amplification techniques are described below. Each of these techniques is suitably performed by the disclosed devices and methods. Allele-specific PCR is a diagnostic or cloning technique based on single-nucleotide polymorphisms (SNPs) (single-base differences in DNA). It requires some knowledge of a DNA sequence, including differences between alleles, and uses primers whose 3' ends encompass the SNP. PCR amplification may be less efficient in the presence of a mismatch between template and primer, so successful amplification with an SNP-specific primer signals presence of the specific SNP in a sequence.

Assembly PCR or Polymerase Cycling Assembly (PCA) is an artificial synthesis of long DNA sequences by performing PCR on a pool of long oligonucleotides with short overlapping segments. The oligonucleotides alternate between sense and antisense directions, and the overlapping segments determine the order of the PCR fragments, thereby selectively producing the final long DNA product.

Asymmetric PCR preferentially amplifies one DNA strand in a double-stranded DNA template. It is used in sequencing and hybridization probing where amplification of only one of the two complementary strands is required. PCR is carried out as usual, but with a great excess of the primer for the strand targeted for amplification. Because of the slow (arithmetic) amplification later in the reaction after the limiting primer has been used up, extra cycles of PCR are required. A recent modification on this process, known as Linear-After-The-Exponential-PCR (LATE-PCR), uses a limiting primer with a higher melting temperature (Tm) than the excess primer to maintain reaction efficiency as the limiting primer concentration decreases mid-reaction.

Helicase-dependent amplification is similar to traditional PCR, but uses a constant temperature rather than cycling through denaturation and annealing/extension cycles. DNA helicase, an enzyme that unwinds DNA, is used in place of thermal denaturation.

Hot start PCR is a technique that reduces non-specific amplification during the initial set up stages of the PCR. It may be performed manually by heating the reaction components to the denaturation temperature (e.g., 95° C.) before adding the polymerase. Specialized enzyme systems have been developed that inhibit the polymerase's activity at ambient temperature, either by the binding of an antibody or by the presence of covalently bound inhibitors that dissociate only after a high-temperature activation step. Hot-start/cold-finish PCR is achieved with new hybrid polymerases that are inactive at ambient temperature and are activated at elongation temperature.

Inter-sequence-specific PCR (ISSR) is a PCR method for DNA fingerprinting that amplifies regions between simple sequence repeats to produce a unique fingerprint of amplified fragment lengths.

Inverse PCR is commonly used to identify the flanking sequences around genomic inserts. It involves a series of DNA digestions and self-ligation, resulting in known sequences at either end of the unknown sequence.

Ligation-mediated PCR: uses small DNA linkers ligated to the DNA of interest and multiple primers annealing to the DNA linkers; it has been used for DNA sequencing, genome walking, and DNA footprinting.

Methylation-specific PCR (MSP) is used to detect methylation of CpG islands in genomic DNA. DNA is first treated with sodium bisulfite, which converts unmethylated cytosine bases to uracil, which is in turn recognized by PCR primers as thymine Two PCRs are then carried out on the modified DNA, using primer sets identical except at any CpG islands within the primer sequences. At these points, one primer set recognizes DNA with cytosines to amplify methylated DNA, and one set recognizes DNA with uracil or thymine to amplify unmethylated DNA. MSP using qPCR can also be performed to obtain quantitative rather than qualitative information about methylation.

Miniprimer PCR uses a thermostable polymerase (S-Tbr) that can extend from short primers ("smalligos") as short as 9 or 10 nucleotides. This method permits PCR targeting to smaller primer binding regions, and is used to amplify conserved DNA sequences, such as the 16S (or eukaryotic 18S) rRNA gene.

Multiplex Ligation-dependent Probe Amplification (MLPA) permits multiple targets to be amplified with only a single primer pair, as distinct from multiplex-PCR.

Multiplex-PCR: consists of multiple primer sets within a single PCR mixture to produce amplicons of varying sizes that are specific to different DNA sequences. By targeting multiple genes at once, additional information may be gained from a single test-run that otherwise would require several times the reagents and more time to perform. Annealing temperatures for each of the primer sets may be optimized to work correctly within a single reaction, and amplicon sizes. That is, their base pair length may be different enough to form distinct bands when visualized by gel electrophoresis.

Nested PCR: increases the specificity of DNA amplification, by reducing background due to non-specific amplification of DNA. Two sets of primers are used in two successive PCRs. In the first reaction, one pair of primers is used to generate DNA products, which besides the intended target, may still consist of non-specifically amplified DNA fragments. The product(s) are then used in a second PCR with a set of primers whose binding sites are completely or partially different from and located 3' of each of the primers used in the first reaction.

Overlap-extension PCR or Splicing by overlap extension (SOE): a genetic engineering technique that is used to splice together two or more DNA fragments that contain complementary sequences. The technique is used to join DNA pieces containing genes, regulatory sequences, or mutations; the technique enables creation of specific and long DNA constructs.

Quantitative PCR (Q-PCR): used to measure the quantity of a PCR product (commonly in real-time). It quantitatively measures starting amounts of DNA, cDNA, or RNA. Q-PCR is commonly used to determine whether a DNA sequence is present in a sample and the number of its copies in the sample. Quantitative real-time PCR can have a high degree of precision. QRT-PCR (or QF-PCR) methods use fluorescent dyes, such as Sybr Green, EvaGreen or fluorophore-containing DNA probes, such as TaqMan, to measure the amount of amplified product in real time. It is also sometimes abbreviated to RT-PCR (Real Time PCR) or RQ-PCR. QRT-PCR or RTQ-PCR are more appropriate contractions, as RT-PCR commonly refers to reverse transcription PCR (see below), often used in conjunction with Q-PCR.

Reverse Transcription PCR(RT-PCR): for amplifying DNA from RNA. Reverse transcriptase reverse transcribes RNA into cDNA, which is then amplified by PCR. RT-PCR is widely used in expression profiling, to determine the expression of a gene or to identify the sequence of an RNA transcript, including transcription start and termination sites. If the genomic DNA sequence of a gene is known, RT-PCR can be used to map the location of exons and introns in the gene. The 5' end of a gene (corresponding to the transcription start site) is typically identified by RACE-PCR (Rapid Amplification of cDNA Ends).

Solid Phase PCR: encompasses multiple meanings, including Polony Amplification (where PCR colonies are derived in a gel matrix, for example), Bridge PCR (primers are covalently linked to a solid-support surface), conventional Solid Phase PCR (where Asymmetric PCR is applied in the presence of solid support bearing primer with sequence matching one of the aqueous primers) and Enhanced Solid Phase PCR (where conventional Solid Phase PCR can be improved by employing high Tm and nested solid support primer with optional application of a thermal step to favor solid support priming).

Thermal asymmetric interlaced PCR (TAIL-PCR) may be useful for isolation of an unknown sequence flanking a known sequence. Within the known sequence, TAIL-PCR uses a nested pair of primers with differing annealing temperatures; a degenerate primer is used to amplify in the other direction from the unknown sequence.

Touchdown PCR (Step-down PCR) is a variant of PCR that aims to reduce nonspecific background by gradually lowering the annealing temperature as PCR cycling progresses. The annealing temperature at the initial cycles is usually a few degrees (3-5° C.) above the Tm of the primers used, while at the later cycles, it is a few degrees (3-5° C.) below the primer Tm. The higher temperatures give greater specificity for primer binding, and the lower temperatures permit more efficient amplification from the specific products formed during the initial cycles.

PAN-AC uses isothermal conditions for amplification, and may be used in living cells.

Universal Fast Walking is useful for genome walking and genetic fingerprinting using a more specific two-sided PCR than conventional one-sided approaches (using only one gene-specific primer and one general primer) by virtue of a mechanism involving lariat structure formation. Streamlined derivatives of UFW are LaNe RAGE (lariat-dependent nested PCR for rapid amplification of genomic DNA ends), 5' RACE LaNe, and 3' RACE LaNe.

COLD-PCR (co-amplification at lower denaturation temperature-PCR) is a modified Polymerase Chain Reaction (PCR) protocol that enriches variant alleles from a mixture of wildtype and mutation-containing DNA.

Another alternative isothermal amplification and detection method that is isothermal in nature is described at http://www.invaderchemistry.com/ (Invader Chemistry™). This method may be performed by the disclosed devices and methods. Another alternative amplification technique (so-called qPCR) is disclosed by MNAzyme (http://www.speedx.com.au/MNAzymeqPCR.html), which technique is also suitable for the presently disclosed devices and methods.

One may also effect amplification based on nucleic acid circuits (which circuits may be enzyme-free). The following references (all of which are incorporated herein by reference in their entireties) describe exemplary circuits; all of the following are suitable for use in the disclosed devices and methods: Li et al., "Rational, modular adaptation of enzyme-free DNA circuits to multiple detection methods," Nucl. Acids Res. (2011) doi: 10.1093/nar/gkr504; Seelig et al., "Enzyme-Free Nucleic Acid Logic Circuits," Science (Dec. 8, 2006), 1585-1588; Genot et al, "Remote Toehold: A Mechanism for Flexible Control of DNA Hybridization Kinetics," JACS 2011, 133 (7), pp 2177-2182; Choi et al., "Programmable in situ amplification for multiplexed imaging of mRNA expression," Nature Biotechnol, 28:1208-1212, 2010; Benner, Steven A., and A. Michael Sismour. "Synthetic Biology." Nat Rev Genet. 6, no. 7 (2005): 533-543; Dirks, R. M., and N. A. Pierce. "Triggered Amplification by Hybridization Chain Reaction." Proceedings of the National Academy of Sciences of the United States of America 101, no. 43 (2004): 15275; Graugnard, E., A. Cox, J. Lee, C. Jorcyk, B. Yurke, and W. L. Hughes. "Kinetics of DNA and Rna Hybridization in Serum and Serum-Sds." Nanotechnology, IEEE Transactions on 9, no. 5 (2010): 603-609; Li, Bingling, Andrew D. Ellington, and Xi Chen. "Rational, Modular Adaptation of Enzyme-Free DNA Circuits to Multiple Detection Methods." Nucleic Acids Research, (2011); Li, Q., G. Luan, Q. Guo, and J. Liang. "A New Class of Homogeneous Nucleic Acid Probes Based on Specific Displacement Hybridization." Nucleic Acids Research 30, no. 2 (2002): e5-e5; Picuri, J. M., B. M. Frezza, and M. R. Ghadiri. "Universal Translators for Nucleic Acid Diagnosis." Journal of the American Chemical Society 131, no. 26 (2009): 9368-9377; Qian, Lulu, and Erik Winfree. "Scaling up Digital Circuit Computation with DNA Strand Displacement Cascades." Science 332, no. 6034 (2011): 1196-1201; Tsongalis, G. J. "Branched DNA Technology in Molecular Diagnostics." American journal of clinical pathology 126, no. 3 (2006): 448-453; Van Ness, Jeffrey, Lori K. Van Ness, and David J. Galas. "Isothermal Reactions for the Amplification of Oligonucleotides." Proceedings of the National Academy of Sciences 100, no. 8 (2003): 4504-4509; Yin, Peng, Harry M. T. Choi, Colby R. Calvert, and Niles A. Pierce. "Programming Biomolecular Self-Assembly Pathways." Nature 451, no. 7176 (2008): 318-322; Zhang, D. Y., and E. Winfree. "Control of DNA Strand Displacement Kinetics Using Toehold Exchange." Journal of the American Chemical Society 131, no. 47 (2009): 17303-17314; Zhang, David Yu, Andrew J. Turberfield, Bernard Yurke, and Erik Winfree. "Engineering Entropy-Driven Reactions and Networks Catalyzed by DNA." Science 318, no. 5853 (2007): 1121-1125; Zhang, Z., D. Zeng, H. Ma, G. Feng, J. Hu, L. He, C. Li, and C. Fan. "A DNA-Origami Chip Platform for Label-Free SNP Genotyping Using Toehold-Mediated Strand Displacement." Small 6, no. 17 (2010): 1854-1858.

It should also be understood that the present disclosure is not limited to application to molecules, as the disclosed devices and methods may be applied to organisms (e.g., those described in paragraph 0133 of priority application PCT/US2010/028316 and also elsewhere in that application), single cells, single biological particles (e.g., bacteria), single vesicles, single exosomes, single viruses, single spores, lipoprotein particles, and the like, and single non-biological particles. One exemplary analysis of lipoprotein particles may be found at www.liposcience.com. Furthermore, it should also be understood that the disclosed devices and methods may be applied to stochastic confinement (described in, for example, "Stochastic Confinement to Detect, Manipulate, And Utilize Molecules and Organisms," patent application PCT/US2008/071374), and reactions and manipulations of stochastically confined objects. As one non-limiting example, biological samples may be assessed for the presence or level of certain bacteria, such as those organisms that serve as markers for bacterial vaginosis. This assessment may be performed by amplifying nucleic acids that may be present in the sample and correlating the levels of those nucleic acids to the presence or absence of the marker organisms. One exemplary analysis is found at http://www.viromed.com/client/cats/BV %20LAB.pdf.

It should be understood that "nucleic acid" is not limited to DNA. "Nucleic acid" should be understood as referring to RNA and/or a DNA. Exemplary RNAs include, but are not limited to, mRNAs, tRNAs,snRNAs, rRNAs, retroviruses, small non-coding RNA, microRNAs, ploysomal RNAs, pre-mRNAs, intromic RNA, and viral RNA. Exemplary DNAs include, but are not limited to, genomic DNA, plasmid DNA, phage DNA, nucleolar DNA, mitochondrial DNA, chloroplast DNA, cDNA, synthetic DNA, yeast artificial chromosomal DNA, bacterial artificial chromosomal DNA, other extrachromosomal DNA, and primer extension products.

In some embodiments, a nucleic acid comprises PNA and/or LNA (locked nucleic acid). In still other embodiments, a nucleic acid comprises one or more aptamers that can be in the form of single stranded DNA, RNA, or modified nucleic acids. Nucleic acid aptamers may be single stranded or double stranded. In some embodiments, nucleic acid contains nucleotides with modified synthetic or unnatural bases, including any modification to the base, sugar or backbone. Further information is found in U.S. Pat. No. 7,790,385 and also in United States patent application publications US2008/0032310, US2008/0050721, and US2005/0089864, all of which are incorporated herein by reference in their entireties for any and all purposes.

It should also be understood that in some embodiments, the disclosed devices and methods provide for detection of target molecules with or without quantification (or estimated quantification) of the target molecules. Accordingly, it is not necessary for a user to estimate the concentration or level of a target in a sample; the disclosed devices and methods may be used to detect the presence of a target in a yes/no fashion. This is especially useful in applications where the user may desire only to know whether a particular target (e.g., a virus) is present; in such cases, the precise level of the target is of lesser importance.

Such detection can be carried out by physical, chemical, and biological reactions, such as hybridization, nucleic acid amplification, immunoassays, and enzymatic reaction. In some embodiments, this detection method can be used for qualitative analysis of one or more target molecules. As describe above, in some embodiments material may, after a reaction, processing, or even a detection step, be transferred to another device, or even transferred to another region of the same device. In some embodiments, recovered material may be removed from the device. In some embodiments, material after detection may be recovered from device and further analyzed. Such recovery may be carried out, in some embodiments, by accessing individual wells of a device, e.g., by a pipettor. In some embodiments, recovery may be achieved by combining material from multiple wells, for example by actuating a device to the loading position and using a carrier fluid to expel the material from the device.

Exemplary Embodiments

The following illustrates an exemplary embodiment of the disclosed devices. The embodiment comprises a rotationally-configured device for quantifying RNA with a large dynamic range by using multivolume digital RT-PCR (MV digital RT-PCR).

Quantitative detection of RNA provides valuable information for study of gene expression, and has the potential to improve evaluation of diseases (including stroke, leukemia, and prostate cancer), analysis of graft rejection in transplantation, and vaccine development. Quantification of viral RNA has also become useful for monitoring the progression of viral infection and efficacy of applied treatment.

One such instance is in the treatment of HIV. More than 33 million people worldwide are living with HIV, and a large number of them are in developing countries and resource-limited areas. First-line antiretroviral treatment is becoming widely available, and it greatly increases both the duration and quality of life of HIV patients. However, this first-line treatment can fail as the virus mutates and develops drug resistance. In order to stop the global spread of drug resistance and provide proper treatment for patients, it is critical to evaluate the HIV viral load at regular intervals (every 3 to 4 months) after initial treatment is shown to be effective. HIV viral load measurement is a particularly useful tool for diagnosing and evaluating the status of HIV infection in children under age 18 months.

The hepatitis C virus (HCV) infection is also a significant global healthcare burden, as it has been identified as one of the major causes of liver disease and is one of the most common co-infections of HIV. HCV viral load may also need to be monitored to determine the effectiveness of treatment.

The viral load for chronic HCV can range from about 50,000 to about 5 million international units per mL (IU/mL), while for patients responding to antiviral treatment the load will be lower. Successful treatment should result in essentially undetectable levels of HCV viral RNA, and the assessment of such treatment may require HCV viral load measurements capable of a wide dynamic range.

As explained previously, real time quantitative RT-PCR is one standard for monitoring viral load for HIV, HCV, and other viral infections. However, this test is cost-prohibitive under resource-limited settings and usually requires multiple instruments, highly skilled technicians, and isolated rooms to prevent contamination. Moreover, the efficiency of RT-PCR, the quality of sample and selection of targets, and the methods for interpretation of the data present concerns for the accuracy of quantifying RNA using RT-PCR.

While a dipstick device has been developed that provides semiquantitative measurements of HIV viral load after amplification in resource limited settings, no quantitative test exists to resolve a 3-fold ($0.5 \log^{10}$) change in HIV RNA viral load, which is considered to be clinically significant. Digital PCR is one method that performs quantitative analysis of nucleic acids by detecting single molecule of DNA or RNA and can provide an absolute count of the nucleic acid copy number with potentially higher accuracy compared to real time PCR. Existing applications of digital PCT, however, require significant skill and resource commitments.

The exemplary, disclosed devices present a microfluidic platform that can manipulate liquid samples from picoliter-to-microliter scales by relative movement of different plates without the need for complex control systems. These devices may be used for multiplex PCR, digital PCR, and digital isothermal amplification (RPA).

In place of using wells of uniform size, using wells of multiple volumes to achieve the same dynamic range can reduce the total number of wells and increase the spacing among wells to simplify imaging and downstream analysis. A mathematical approach for experimental design and statistical analysis for multivolume digital PCR (MV digital PCR) has been characterized using DNA in Kreutz et al., Anal. Chem. 2011, DOI 10.1021/ac201658s, incorporated herein by reference for all purposes.

A disclosed devices was applied, as set forth below, to quantitative analysis of RNA with large dynamic range by MV digital RT-PCR. This device was characterized with a serial dilution of a synthetic control RNA molecule of 906 nucleotides (906 nt). Also described is a second design of the platform that maintains a large dynamic range for five samples simultaneously, allowing for multiplexed experiments. This system was validated by using HCV control viral RNA and HIV viral RNA together with internal controls. The system also displayed the use of multivolume designs to quantify HIV viral load at a large dynamic range by quantifying purified HIV viral RNA from clinical patients' samples.

Results

First characterized was a multivolume digital device (Design 1, Table 1, FIG. 11) with a large dynamic range suitable for viral load testing. This device contained four different volumes (1 nL, 5 nL, 25 nL, 125 nL) with 160 wells each (FIG. 1A) for a theoretical dynamic range (lower dynamic range, LDR, to upper limit of quantification, ULQ) of $5.2 \times 10^2$ to $4.0 \times 10^6$ molecules/mL at 3-fold resolution and a lower detection limit (LDL) of $1.2 \times 10^2$ molecules/mL in the final RT-PCR mixture. The LDR corresponds to the lowest concentration that can be resolved from a 3- or 5-fold higher concentration; the ULQ is the concentration that has a 95% chance of generating at least one negative well and is equal to the concentration calculated from three negative wells; the LDL is the concentration that has a 95% chance of generating at least one positive well and is equal to the concentration calculated from three positive wells.

Continuous fluidic paths are generated by partially overlapping the wells in the top plate and the wells in the bottom plate (e.g., FIG. 1B, FIG. 1E; FIG. 15). The design of this device follows the general principles of dead-end filling for complete filling of aqueous reagents (FIG. 1C,F). After complete loading, the top plate is slipped (rotated) clockwise by ~8° to break the fluidic path and overlay the wells filled with solution with the wells in the facing plate used to control thermal expansion (FIG. 1D, FIG. 1G). The device is then placed on a flat in situ adaptor for thermal cycling.

The theory for design and analysis of this multivolume device are described in detail and validated by using digital PCR for DNA. Briefly, concentrations were calculated based on Most Probable Number (MPN) theory by combining the results from each volume (i=1, 2, 3, 4) in the first equation below and solving for λ (concentration, molecules/mL), where $n_i$ is the total number of wells at each volume, $b_i$ is the number of negative wells at that volume, and $v_i$ is the well volume (mL). Combining results allows for more precise identification of the "most probable" concentration and also improves the confidence interval. To find the confidence interval, the standard deviation, σ, for ln (λ) is determined using the second equation below, which was derived based on the Fisher information.

$$\sum_{i=1}^{m} n_i \cdot v_i = \sum_{i=1}^{m} \frac{(n_i - b_i) \cdot v_i}{1 - e^{-v_i \cdot \lambda}}$$

$$\sigma = \frac{1}{\sqrt{\lambda^2 \cdot \Sigma \frac{v_i^2 \cdot n_i}{e^{v_i \lambda} - 1}}}$$

To validate the performance of the multivolume device with RNA, digital RT-PCR ws performed using a six order-of magnitude serial dilution of synthetic control RNA template (906 nt). This control RNA was synthesized from a control plasmid and purified by using a commercial purification kit. The concentration of the stock solution of control RNA was measured spectrophotometrically by a Nano-Drop™ device to be ~1.8 ng/μL, corresponding to ~4.1× $10^{12}$ molecules/mL, which may contain some background signal.

Figure 2:
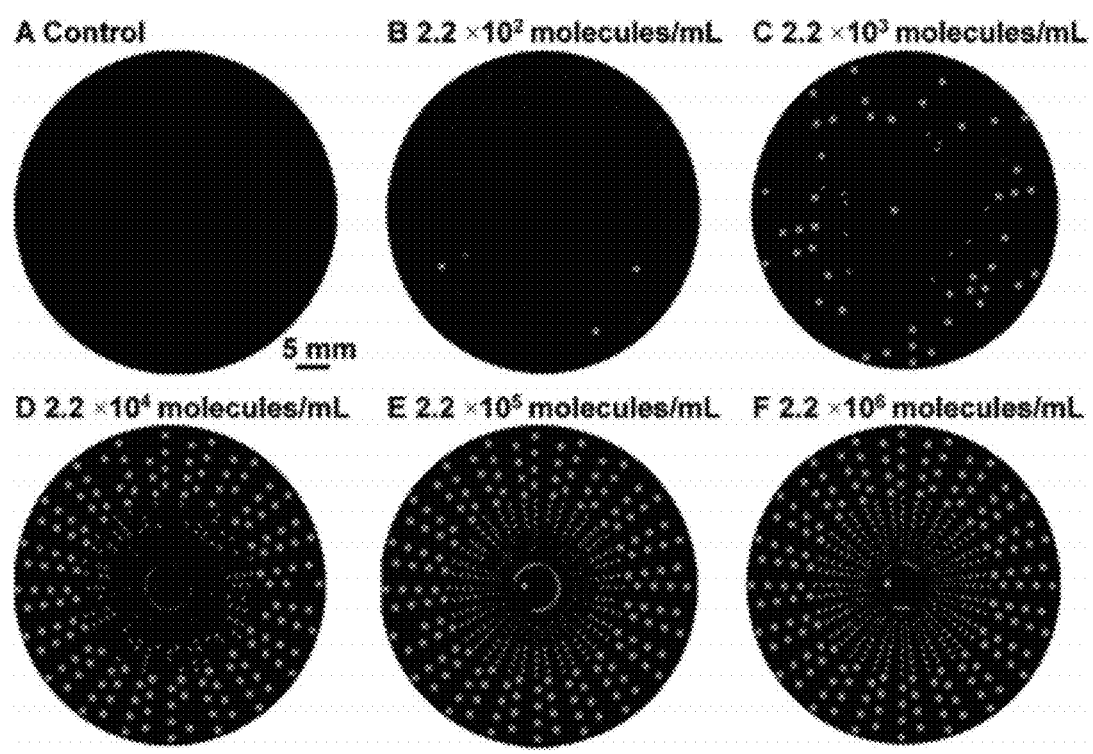
FIG. 2 illustrates end-point fluorescence images of multivolume digital RT-PCR performed on a rotational device according to the present disclosure.
Figure 3:
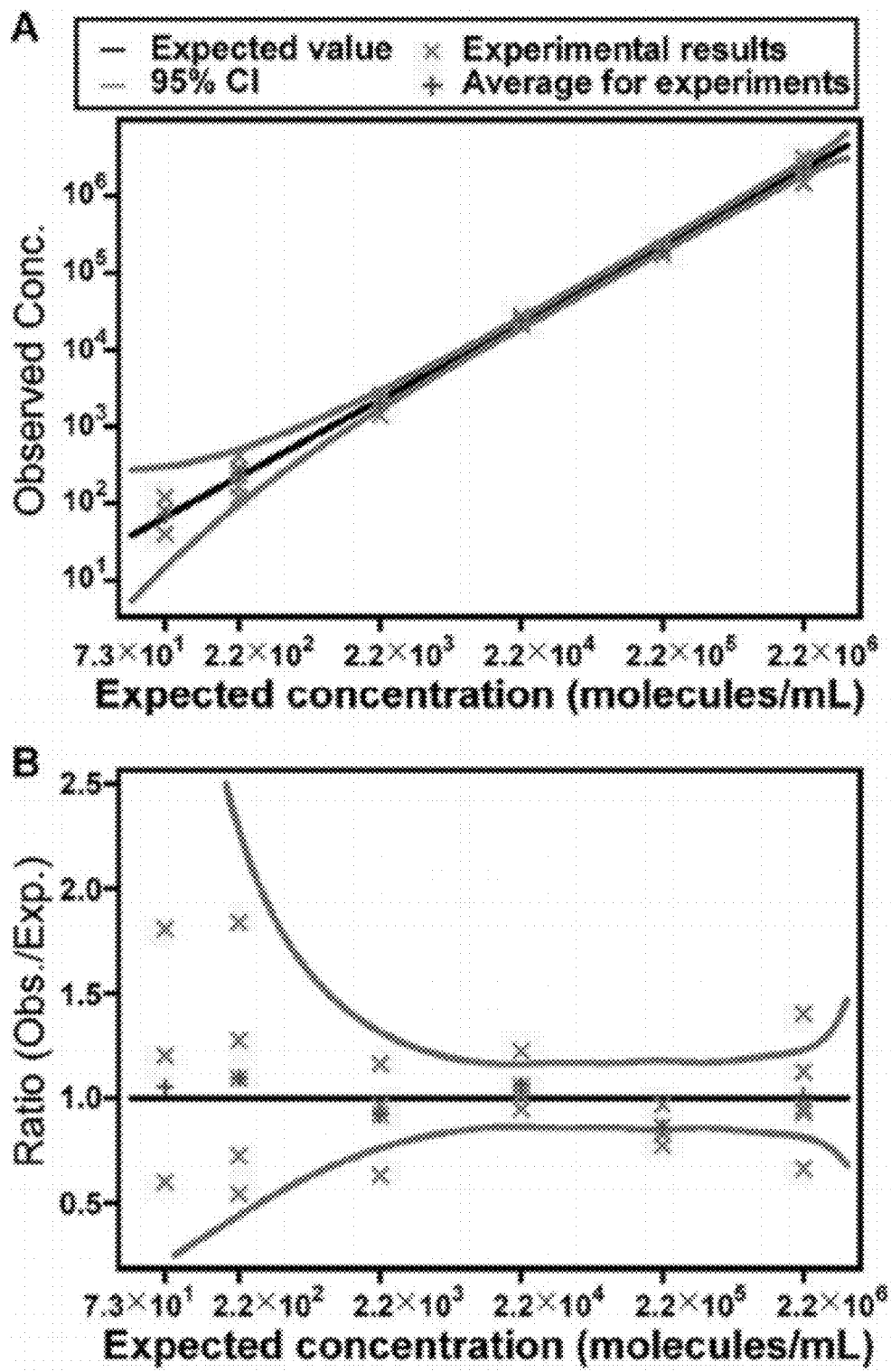
FIG. 3 illustrates performance of digital RT-PCR with synthetic RNA template on an exemplary multivolume device over a 4 $\log_{10}$ dynamic range.

Using the device and through statistical analysis of all MV digital RT-PCR results (FIG. 3), a nominal real concentration of the control RNA in solution was obtained, 2.2×$10^{12}$ molecules/mL, which value was used as the true concentration of all MV digital RT-PCR results reported in FIG. 3. A RT-PCR master mix containing EvaGreen Super-Mix, RT-transcriptase, bovine serum albumin (BSA), and primers was mixed with the RNA template solution. EvaGreen, an intercalating dye, was used for end-point fluorescent imaging after thermal cycling (FIG. 2).

FIG. 1 illustrates a rotational multivolume device (well volumes: 1 nL, 5 nL, 25 nL, 125 nL). (A) Bright field image of the rotational device after slipping to form isolated compartments, shown next to a U.S. quarter. (B-D) Schematics and (E-G) bright field microphotograph show (B, E) the assembled rotational device. (C, F) The device filled with food dye after dead-end filling. (D, G) The device after rotational slipping: 640 aqueous droplets of four different volumes (160 wells with volumes of 1 nL, 5 nL, 25 nL, 125 nL each) were formed simultaneously. In the schematics, dotted lines indicate features in the top plate, and black solid lines represent the features in the bottom plate.

FIG. 2 shows end-point fluorescence images of multivolume digital RTPCR performed on a rotational device for synthetic RNA template at five different concentrations. (A) Control, containing no RNA template. (B-F) Serial dilution of 906 nt RNA template from 2.2×$10^2$ to 2.2×$10^6$ molecules/mL in the RT-PCR mix.

No false positives were observed after amplification in four negative control experiments, as there was no significant increase of fluorescent intensity in wells (FIG. 2A). As the concentration of RNA template increased (the dilution factor decreased), the fraction of positive wells in each set of individual volumes was counted and the concentration of template in the RT-PCR mix was calculated as described above (FIG. 2B-F). The glass device was reused after being thoroughly cleaned with piranha acid (3:1 sulfuric acid: hydrogen peroxide), plasma cleaned, and resilanized with dichlorodimethylsilane. Four to five experiments were performed for each concentration of template, and the calculated concentration of template RNA showed good agreement within the expected statistical distribution at each concentration and scaled linearly with the expected concentration (FIG. 3A). The results at the concentrations of 2.2×$10^6$, 2.2×$10^5$, 2.2×$10^4$, 2.2×$10^3$, 2.2×$10^2$, and 7.3×$10^1$ molecules/mL in the RT-PCR mix were used to estimate an initial stock concentration of control RNA of approximately 2.2×$10^{12}$ molecules/mL. The experimental results across the concentrations agree well with the theoretically predicted distribution (FIG. 3A,B). Of the 26 experiments, 19 fall within the 95% confidence interval and 22 fall within the 99% confidence interval.

FIG. 3 presents the performance of digital RT-PCR with synthetic RNA template on the multivolume device over a 4 $\log_{10}$ dynamic range, comparing the expected concentration of RNA in RT-PCR mix to (A) the observed concentration, and (B) the ratio of the observed/expected concentration. Individual experimental results (crosses) and average results (crosses) for concentration were plotted against the dilution level of the RNA stock solution. Four to five experiments were performed at each concentration, and some experimental results are overlapping. The experimental results show a linear relationship with the dilution level and fit within the expected distribution. The experimental results were used to estimate an initial stock concentration, whose distribution was then fit to the dilution level to provide the expected value (black curve) and 95% confidence interval (gray curves).

Over the dynamic range of the device, the contribution of wells with different volumes to the calculated concentration varies, approximated in FIG. 4A. As the concentration of control RNA template increases (the dilution decreases), the major contribution to the calculated final concentration shifts from wells of large volume (125 nL) to wells of medium volume (25 nL and 5 nL) and then to wells of small volume (1 nL). The percent that the result from each volume contributes to σ serves as an estimate of the relative contribution of that volume to the concentration determined by all volumes on the entire chip. In FIG. 4A, the data bars for the 125 nL volume are for (left to right) 2.2×$10^2$ molecules/mL, 2.2×$10^3$ molecules/mL, and 2.2×$10^4$ molecules/mL. For 25 nL, data bars are (left to right) 2.2×$10^2$ molecules/mL, $2.2\times10^3$ molecules/mL, $2.2\times10^4$ molecules/mL, $2.2\times10^5$ molecules/mL, and $2.2\times10^6$ molecules/mL. For 5 nL volumes, the data bars are (left to right) $2.2\times10^2$ molecules/mL, $2.2\times10^3$ molecules/mL, $2.2\times10^4$ molecules/mL, $2.2\times10^5$ molecules/mL, and $2.2\times10^6$ molecules/mL. For 1 nL volumes, the data bars are (left to right) $2.2\times10^4$ molecules/mL, $2.2\times10^5$ molecules/mL, and $2.2\times10^6$ molecules/mL. The concentration calculated from analysis of positive and negative wells of each of the volumes on the individual device was selfconsistent and was consistent with the calculated concentration determined by combining all wells with different volumes (FIG. 4B). This result indicates that multivolume digital approach is fully compatible with analysis of RNA by RT-PCR.

FIG. 4A shows that for each dilution, the approximate contributions of the results from each well volume toward calculating the final concentration were calculated based on the contributions of each volume to the standard deviation, $\sigma$. FIG. 4(B), showing the concentration of RNA template calculated from the overall chip (combining all well volumes, solid bars) and individual volumes (patterned bars) is self-consistent on the MV digital RT-PCR device. Four experiments were performed with $2.2\times10^4$ molecules/mL of control RNA template (906 nt) in the RT-PCR mix.

To illustrate incorporation of multiplexing into the device while maintaining the high dynamic range, the design of the multivolume device was modified by adding two additional volumes (FIG. 11, Design 2A): 0.2 nL (160 wells) and 625 nL (80 wells). When the rotational chip is split into five sections to quantify five different analytes, the 0.2 nL wells extend the upper limit of quantification with 3-fold resolution to $1.2\times10^7$ molecules/mL in the RT-PCR mix, and the 625 nL wells maintain a reasonable lower detection limit of $2.0\times10^2$ molecules/mL and lower dynamic range with 3-fold resolution at $1.8\times10^3$ molecules/mL in the RT-PCR mix (FIG. 5A). The higher upper limit of quantification is required to quantify HCV viral RNA, and the lower dynamic range and lower detection limit are required for the HIV viral load test. Five different solutions can be introduced into the device simultaneously (FIG. 5A) for multiplexed analysis.

As HCV is one of the most common co-infections for HIV patients, validation was performed on the multiplexed device with a five-plex panel: measurement of HIV viral RNA, measurement of HCV control viral RNA, a negative control for HIV, a negative control for HCV, and measurement of 906 nt control RNA in HCV sample for quantification of sample recovery rate (FIG. 5B,C). The 906 nt control RNA was the same one characterized by using digital RT-PCR on the device (design 1; see FIGS. 1 and 11). HIV viral RNA was purified from an archived sample of plasma containing HIV (viral RNA estimated to be ~$1.5\times10^6$ molecules/mL) from a de-identified patient sample, and HCV control viral RNA was purified from a commercial sample containing control HCV virus (25 million IU/mL, OptiQuant-S HCV Quantification Panel, Acrometrix) using the iPrep purification instrument, as described elsewhere herein. As the final elution volume of purified nucleic acid is generally smaller than the starting volume of plasma, there is a concentrating effect on viral RNA after sample purification. To characterize this concentrating effect, the 906 nt control RNA with known concentration was added to the lysed plasma and was quantified again after sample preparation. The ratio of the concentration of 906 nt control RNA after/before sample preparation is defined as the concentrating factor. The concentrating factors after sample purification were approximately 6.6 for HIV viral RNA and approximately 4.5 for HCV control viral RNA. Primers for HIV and HCV were selected. Only one pair of primers was added to each sample, and the experiment was repeated six times. In those six experiments, no false positives were observed in either HIV or HCV negative control panels after thermal cycling, and no crosscontamination was observed among different panels. From these six experiments, the average calculated concentration of HIV viral RNA after purification was $7.9\times10^6$ molecules/mL with standard deviation of $2.5\times10^6$ molecules/mL, corresponding to $1.2\times10^6$ molecules/mL with standard deviation of $3.7\times10^5$ molecules/mL in the original plasma sample. The average concentration of HCV control viral RNA after purification was $1.0\times10^8$ molecules/mL with standard deviation of $4.4\times10^7$ molecules/mL, corresponding to $2.3\times10^7$ molecules/mL with standard deviation of $9.7\times10^6$ molecules/mL in the original control plasma sample. (Additional information may be found in "Multiplexed Quantification of Nucleic Acids," Shen et al., JACS 2011.)

There is no universal conversion factor from international units to copy number for HCV viral load; it is a value that depends on the detection platform, including the protocols and equipment used. Because the HCV concentration in the original commercial sample was stated to be $2.5\times10^7$ IU/mL, the conversion factor from international units to copy number for HCV viral load in the test is approximately 0.9. The same conversion number (0.9) was published for the Roche Amplicor HCV Monitor v2.0 test when using a manual purification procedure.

FIG. 5 illustrates a device for multiplexed, multivolume digital RT-PCR with high dynamic range. (A) A photograph of a multiplex device for up to five samples corresponding to designs 2A and 2B in Table 1 (FIG. 11) with a total of 80 wells of 625 nL, 160 wells of 125 nL, 160 wells of 25 nL, 160 wells of 5 nL, 160 wells of 1 nL, and 160 wells of 0.2 nL. (B) Fluorescent photograph of a multiplexed digital RT-PCR detection panel: (I) measurement of internal control of 906 nt RNA template in HCV sample; (II) HCV control viral RNA measurement; (III) negative control for HIV (HIV primers with no loaded HIV RNA template); (IV) HIV viral RNA measurement; (V) negative control for HCV (HCV primers with no loaded HCV RNA template). Inset shows an amplified area from HCV viral load test.

Figure 6:
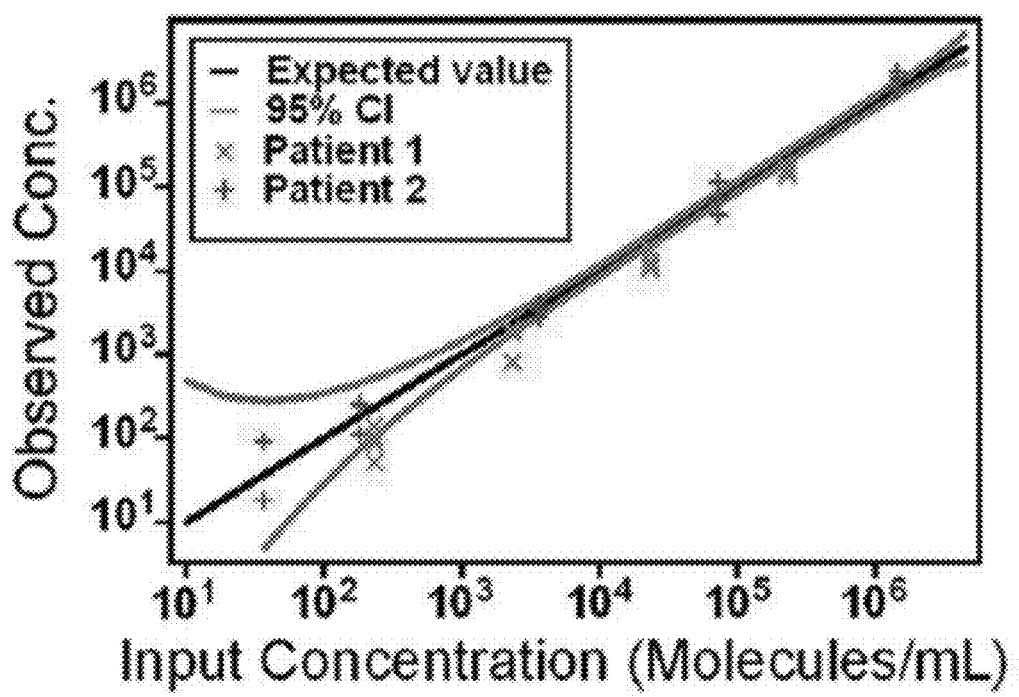
FIG. 6 illustrates representative multivolume digital RT-PCR for quantification of HIV viral load in two patients' samples.

FIG. 6 shows multivolume digital RT-PCR for quantification of HIV viral load in two patients' samples. Input concentration was calculated from a single clinical measurement for each patient using the Roche CAP/CTM v2.0 system and was assumed to be the true concentration. Each concentration was measured at least four times, and each individual experiment is plotted as single point on the graph. The black solid line is the predicted concentration based on the assumption that the clinical measurement gave a true concentration. The gray solid lines were calculated using MPN theory and represent the 95% confidence interval for the predicted concentration.

The tabular summary in FIG. 9 present the detection and quantification data and dynamic range for the two designs investigated here. Without being bound to any single theory, the dynamic range of design 1 can be easily extended by adding a set of wells smaller than 1 nL in volume and a set of wells larger than 125 nL in volume. Therefore, if a larger dynamic range is required, the multiplexed design (Design 2A, FIG. 11) may be used for a single sample (Design 2B, FIG. 11). When using the entire chip for one sample, the 160 smallest wells (0.2 nL in volume) extend the upper limit of quantification with 3-fold resolution to $2.0\times10^7$ molecules/mL in the RT-PCR mix and the 80 largest wells (625 nL in volume) extend the lower detection limit to 40 molecules/mL and lower dynamic range with 3-fold resolution to $1.7 \times 10^2$ molecules/mL in the RT-PCR mix (Table 1, Design 2B, FIG. 11). This large dynamic range is useful for quantification of viral load.

Figure 11:
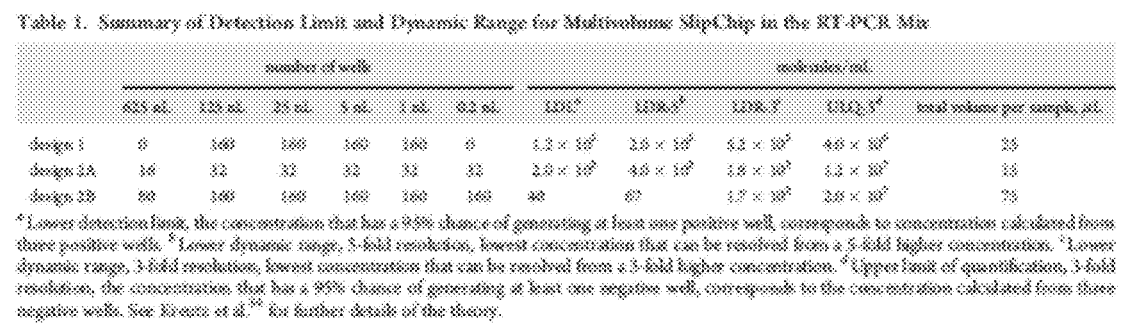

A RT-PCR mix containing an HIV viral RNA sample (prepared as described above and then serially diluted) with an expected concentration of 51 molecules/mL was used to test the lower detection limit of design 2B (FIG. 11). Three negative control experiments were performed (without HIV viral RNA) in parallel, and no false positives were observed. Six experiments were performed to quantify the viral RNA concentration (see FIG. 7), and the average calculated HIV viral RNA concentration in the RT-PCR mix was 70 molecules/mL with standard deviation of 20 molecules/mL, corresponding to 32 molecules/mL with standard deviation of 9 molecules/mL in the original plasma sample.

To further validate the feasibility of using a rotational multivolume device to quantify HIV viral load, Design 1 (FIG. 11) was used to measure HIV viral RNA purified from two archived samples of HIV-infected blood plasma from two different anonymous patients. The HIV viral RNA from each patient sample was extracted and purified automatically using the iPrep purification instrument, and concentrating factors of 7.1 and 6.6 were achieved for the two different patient samples. Each patient sample of purified HIV viral RNA was serially diluted and characterized by MV digital RT-PCR on the device using previously published primers, and each experiment was repeated at least four times (FIG. 6). The same plasma samples were characterized in a single experiment using the Roche COBAS AmpliPrep/COBAS TaqMan HIV-1 Test, v2.0 (CAP/CTM v2.0) according to the manufacturer's recommendation, and these values were treated as the standard for characterization. The data from device were self-consistent for both patients (FIG. 6). Three negative control experiments using the same primers but no HIV template did not show false positive, as no increase of fluorescent intensity was observed (see FIG. 10).

Figure 7:
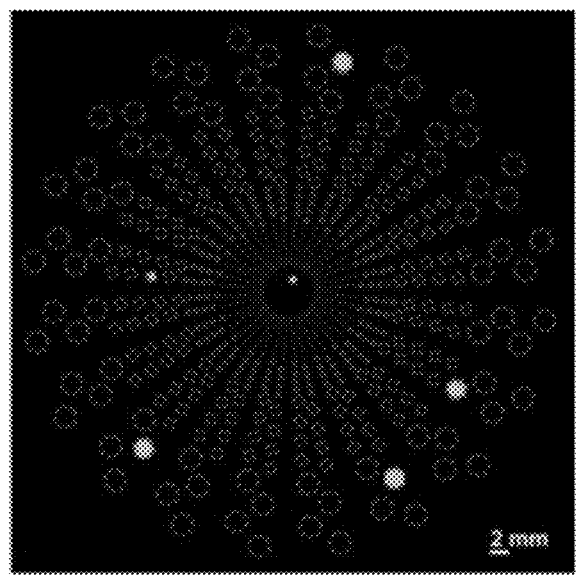
FIG. 7 illustrates a representative experiment performing RT-PCR of HIV viral RNA at an expected concentration of 51 molecules/mL in a RT-PCR mix.

For patient 1, the results (FIG. 6, crosses) were on average approximately 40% lower than that predicted by the single-point measurement of the HIV viral load using Roche CAP/CTM v2.0 (see FIG. 7). There were differences in the test designs: while the present experiment targets a single LTR region of HIV RNA, the Roche CAP/CTM v2.0 test includes two HIV sequences: one in gag and another in LTR region. Further, the two tests use different detection methods (EvaGreen in the present experiment vs TaqMan probes in the Roche CAP/CTM v2.0 test) and different internal controls. For patient 2, excellent agreement with the Roche clinical measurement was observed over the entire range (FIG. 6, plus marks; see also FIG. 10 (tabular summary). Without being bound to any single theory, this difference in agreement between the two methods for the two samples is not surprising, given that each patient has a unique HIV viral genome, and the primers, internal controls, and detection method used in one method may be better suited to detect one patient's viral genome than another's. Overall, taking into consideration the concentrating effect during sample preparation, the lowest concentration of serially diluted HIV viral RNA detected on the device corresponded to 37 molecules/mL in the patient plasma, and the highest concentration corresponded to 1.7 million molecules/mL in the patient plasma.

Results Summary

Figure 4:
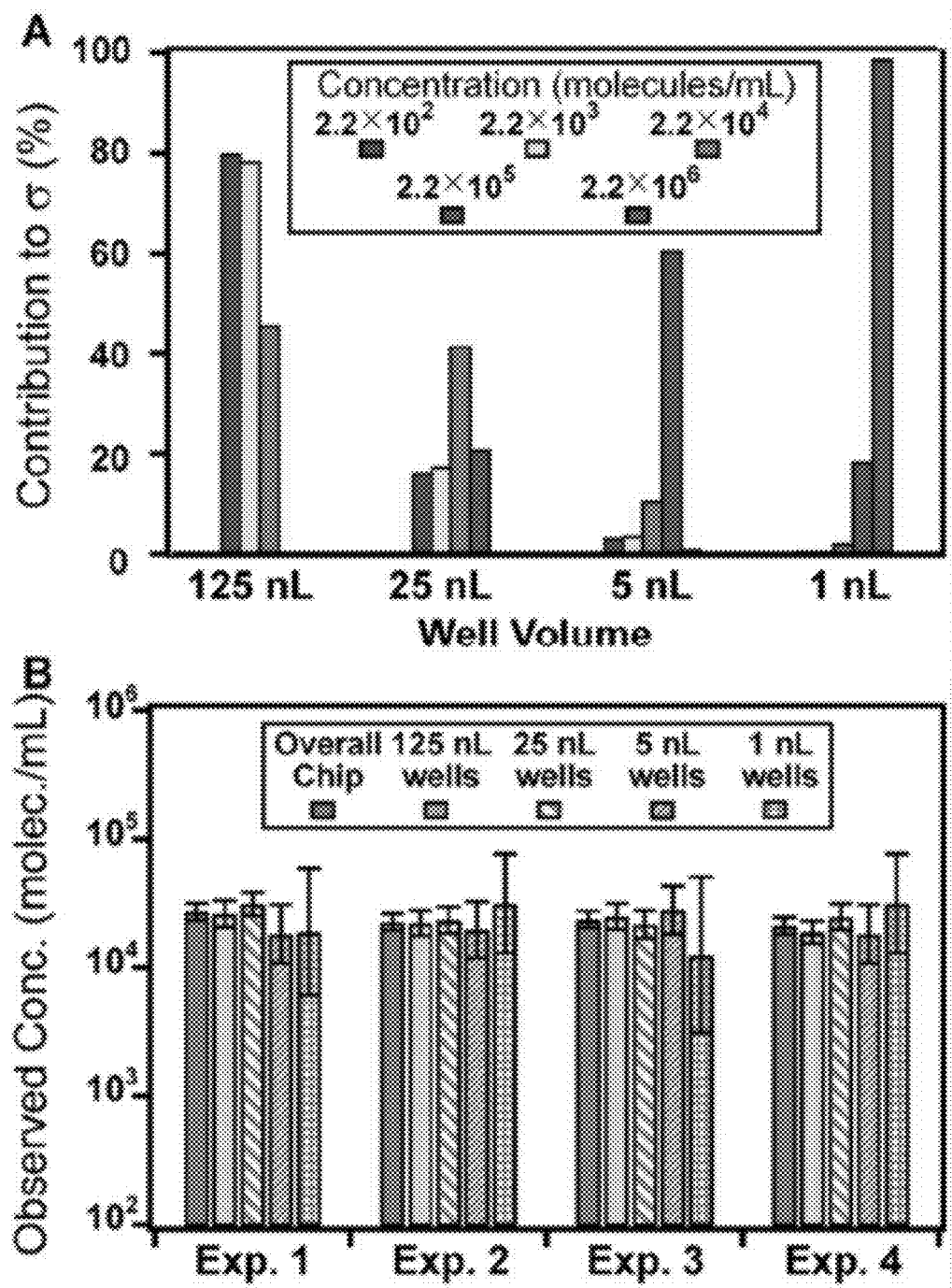
FIG. 4 illustrates performance of an exemplary device.

Motivated by the problem of quantifying viral load under point-of-care and resource-limited settings, here is shown successful testing of the applicability of multivolume digital assays to quantitative analysis of RNA over wide dynamic range via digital RT-PCR on two rotational devices (Table 1). The first device has a dynamic range (at 95% CI) of $5.2 \times 10^2$ to $4.0 \times 10^6$ molecules/mL with 3-fold resolution and lower detection limit of $1.2 \times 10^2$ molecules/mL. The device was characterized using synthetic control RNA, demonstrating that MV digital RT-PCR performs in agreement with theoretical predictions over the entire dynamic range (FIG. 3). Results from wells of different volumes were mutually consistent and enabled quantification over a wide dynamic range using only 640 total wells (FIG. 4). This chip was also validated with viral RNA from two HIV patients (FIG. 6), demonstrating good agreement with single-point measurements performed on a Roche CAP/CTM v2.0 clinical instrument. Using this chip, positive wells were detected that corresponded to a concentration of 81 molecules/mL HIV viral RNA purified from patient plasma in the RT-PCR mix, which corresponds to around 37 molecules/mL in the original plasma samples. While below the detection limit at 95% confidence interval, this concentration should give at least one positive well 86% of the time, so it is not surprising that all four of the experiments had at least one positive well at this concentration.

A second chip was used to test the scalability and flexibility of the multivolume approach by introducing both multiplexed and higher-range quantification. Additional wells were added with volumes of 0.2 nL and 625 nL and divided the device into five individual regions. There was no evidence of cross-contamination among samples on this rotational design, in agreement with previous results on a translational device. This multiplexed device was designed to test five samples, each at a dynamic range (3-fold resolution) from $1.8 \times 10^3$ to $1.2 \times 10^7$ molecules/mL with a lower detection limit of $2.0 \times 10^2$ molecules/mL. Multiplexing capability (FIG. 5) enables a number of features on the same chip, including (i) incorporating negative controls, (ii) measuring levels of control RNA to quantify the quality of sample preparation, (iii) monitoring co-infections, (iv) designing customized arrays for multiple targets, i.e. for nucleic acid targets that require measurements with different dynamic ranges and resolution, using wells of different sizes with customized numbers of wells at each size for each target, and (v) allowing for flexibility depending on technical and economic constraints by using the same device to perform either more analyses of lower quality, but at proportionally lower cost, or a single analysis of high quality including wider dynamic range and higher resolution. If this multiplexed device is used for a single sample, the dynamic range of the device with 3-fold resolution is designed to be $1.7 \times 10^2$ to $2.0 \times 10^7$ molecules/mL with a lower detection limit of 40 molecules/mL. Even with only a modest concentrating effect during sample preparation, this device would enable detecting targets at 10-20 molecules/mL in the original sample.

The high sensitivity of the this MV digital RT-PCR platform is valuable for a number of applications beyond viral load, including detecting rare cells and rare mutations, prenatal diagnostics, and monitoring residual disease. Besides monitoring the HIV viral load of patients on antiretroviral treatments, this approach is a method to screen newborns whose mothers are carrying HIV, where maternal HIV antibodies would potentially interfere with the antibody test. In addition, similar molecular diagnostics methods may be used to measure proviral DNA in infants. This approach can also be applied to investigation of copy number variation and gene expression, both for both for research and diagnostic settings.

The rotational format of the device is useful for resource-limited settings because the movement is easy to control even manually; for a chip with a 2 in. (50 mm) diameter, a 8° rotation moves the outer edge of the chip by ~3.5 mm, a distance that is easily done by hand, especially with internal stoppers and guides. At the same time, that rotation moves the wells which are 2.8 mm from the center by 0.39 mm. This feature is ideal for multivolume formats but also can be taken advantage of in single-volume formats. The devices are also particularly attractive for multivolume formats due to its lack of valves and ease of operation. A number of additional developments will increase the usefulness this chip. The considerations among resolution, dynamic range, and the extent of multiplexing of the multivolume device are described (Kreutz et al., Anal. Chem. 2011, DOI 10.1021/ac201658s). The exemplary designs presented here were fabricated in glass, and a functional device of a different design made from plastic by hot embossing was previously demonstrated.

For applications to resource-limited settings, devices made with inexpensive materials such as plastics are suitable. The disclosed devices are compatible with other amplification chemistries, including polymerization and depolymerization methods, toe-hold initiated hybridization-based amplification, and other amplifications including silver-based amplification. When combined with isothermal amplification methods, such as recombinase polymerase amplification, loop-mediated amplification, strand-displacement amplification, helicase-dependent amplification, rolling circle amplification, and visual readout methods, the MV digital RT-PCR device makes quantitative molecular diagnostics accessible in resource-limited settings.

Chemicals and Materials

All solvents and salts obtained from commercial sources were used as received unless otherwise stated. SsoFast EvaGreen SuperMix (2X) was purchased from Bio-Rad Laboratories (Hercules, Calif.). One-Step SuperScript® III Reverse Transcriptase, iPrep™ purification instrument, and iPrep™ PureLink™ virus kit were purchased from Invitrogen Corporation (Carlsbad, Calif.). All primers were purchased from Integrated DNA Technologies (Coralville, Iowa). Bovine serum albumin (20 mg/mL) was ordered from Roche Diagnostics (Indianapolis, Ind.). Mineral oil, tetradecane, and DEPC-treated nuclease-free water were purchased from Fisher Scientific (Hanover Park, Ill.). Dichlorodimethylsilane was ordered from Sigma-Aldrich (St. Louis, Mo.). PCR Mastercycler and in situ adapter were purchased from Eppendorf (Hamburg, Germany) Spectrum food color was purchased from August Thomsen Corp (Glen Cove, N.Y.). Soda-lime glass plates coated with layers of chromium and photoresist were ordered from Telic Company (Valencia, Calif.). Photomasks were designed using AutoCAD (San Rafael, Calif.) and ordered from CAD/Art Services, Inc. (Bandon, Oreg.). Microposit™ MF™-CD-26 developer was purchased from Rohm and Hass Electronic Materials LLC (Marlborough, Mass.). Amorphous diamond coated drill bits were purchased from Harvey Tool (0.030 inch cutter diameter, Rowley, Mass.). Adhesive PDMS film (0.063 inch thick) was purchased from McMaster (Atlanta, Ga.). The MinElute PCR purification kit and QJAamp Viral RNA mini kit were purchased from Qiagen Inc. (Valencia, Calif.). The OptiQuant®-S HCV RNA quantification panel was purchased from AcroMetrix (Benicia, Calif.).

Fabrication of Devices for Multivolume Digital RT-PCR

The procedure for fabricating the devices from soda lime glass was based on procedures described in previous work. To fabricate devices for multivolume digital RT-PCR, wells of two different depths were etched using a two-step exposing-etching protocol. The soda lime glass plate pre-coated with chromium and photoresist was first aligned with a photomask containing the design for wells of 25 nL and 125 nL for Design 1 (Table 1, FIG. 11). For Design 2, this photomask also contained the designs of the additional wells of 625 nL. The glass plate was then exposed to UV light using standard exposure protocols. After exposure, the glass plate was detached from the photomask and immersed in developer to immediately remove the photoresist that was exposed to UV light. The underlying chromium layer that was exposed was removed by applying a chromium etchant (a solution of 0.6:0.365 mol/L $HClO_4/(NH_4)_2Ce(NO_3)_6$). The glass plate was thoroughly rinsed with water and dried with nitrogen gas. The glass plate was then aligned with a second photomask containing the designs of wells of 1 nL and 5 nL for Design 1 (Table 1, FIG. 11) by using a mask aligner. For Design 2 (FIG. 11), this second photomask also contained the designs of the additional wells of 0.2 nL. The glass plate was then exposed to UV light a second time. After the second exposure, the photomask was detached from the glass plate, and the back side of the glass plate was protected with PVC sealing tape. The taped glass plate was then immersed in a glass etching solution (1:0.5:0.75 mol/L $HF/NH_4F/HNO_3$) to etch the glass surface where chromium coating was removed in the previous step (areas containing wells of 25 nL, 125 nL, and 625 nL), and the etching depth was measured by a profilometer. After the larger features were etched to a depth of 70 µm, the glass plate was placed in the developer again to remove the previously exposed photoresist in areas containing the patterns for the smaller features (1 nL and 5 nL wells, and the additional wells of 0.2 nL for Design 2, FIG. 11). The underlying chromium layer was removed by using the chromium etchant as describe above, and a second glass etching step was performed to etch all features to a further depth of 30 µm. The final device contained wells of depths of 100 µm and 30 µm was fabricated.

After the two-step etching, the glass plate was thoroughly rinsed with Millipore water and ethanol and then dried with nitrogen gas. The glass plate was oxidized using a plasma cleaner and immediately placed in a desicator with dichlorodimethylsilane for gas-phase silanization. For Design 2A (FIG. 11), circular inlet reservoirs (4 mm inner diameter and 6 mm outer diameter) were made by cutting adhesive PDMS film, then fixing the reservoirs around the five inlets before plasma cleaning. After one hour, the silanized glass plate was thoroughly rinsed with chloroform, acetone, and ethanol, and then dried with nitrogen gas.

To re-use the glass devices, each device was thoroughly cleaned with piranha acid (3:1 sulfuric acid: hydrogen peroxide), then oxidized using a plasma cleaner and silanized as described above.

Device Assembly

Devices were assembled under de-gassed oil (mineral oil:tetradecane 1:4 v/v). The bottom plate was immersed into the oil phase with the patterned wells facing up, and the top plate was then immersed into the oil phase and placed on top of the bottom plate with the patterned side facing down. The two plates were aligned under a stereoscope (Leica, Germany) as shown in FIG. 1A and stabilized using binder clips.

Device Loading

A through-hole was drilled in the center of the top plate to serve as the solution inlet for Design 1 and Design 2B. The reagent solution was loaded through the inlet by pipetting. For Design 2A, five through-holes were drilled at the top left corner of the top plate to serve as fluid inlets (FIG. 5A). For multiplex experiments, five different reaction solutions were placed in the inlet reservoirs, and a dead-end filling adapter was placed on top of the devices to cover all the inlets. A pressure of 18 mmHg was applied to load all the solutions simultaneously. The principle and detailed method for dead-end filling are described in a previous work.[3] Reservoirs were removed after the solution was loaded.

Synthesis and Purification of Control RNA (906 nt)

The control RNA (906 nucleotide) was synthesized from the LITMUS 28iMal Control Plasmid using a HiScribe™ T7 In Vitro Transcription Kit with the manufacture's recommended procedures (New England Biolabs, Ipswich, Mass.) and purified using MinElute PCR purification kit with manufacture recommended protocols.

Automatic Viral RNA Purification from Plasma Sample

Plasma samples containing the HIV virus were obtained from deidentified patients at the University of Chicago Hospital. Plasma containing a modified HCV virus as a control (25 million IU/mL, part of OptiQuant-S HCV Quantification Panel) was purchased from AcroMetrix (Benicia, Calif.). A plasma sample of 400 µL was mixed with 400 µL lysis buffer (Invitrogen Corporation, Carlsbad, Calif.) to lyse the virus. Then 2 µL of control RNA (906 nt) was added to characterize the purification efficiency and concentrating factor. The mixed sample was then transferred into the iPrep™ PureLink™ virus cartridge. The cartridge was placed in the iPrep™ purification instrument and the purification protocol was performed according to the manufacturer's instructions. The final elution volume was 50 µL, therefore a theoretical eight-fold concentrating factor was expected. The initial concentration of control RNA and the concentration of control RNA in the purified sample after preparation were characterized on the device (Design 1). The final concentrating factor was 4.5 for HCV and 6.6 for HIV in the multiplex RT-PCR amplification (FIG. 5). The concentrating factors for the two HIV samples were 7.1 and 6.6 for the experiments in FIG. 6.

Primer Sequences for RT-PCR Amplification

Primers for the control RNA (906 nt) were: GAA GAG TTG GCG AAA GAT CCA CG (SEQ ID NO: 1) and CGA GCT CGA ATT AGT CTG CGC (SEQ ID NO: 2). The control RNA template was serially diluted in 1 mg/mL BSA solution. The RT-PCR mix contained the following: 30 µL of 2× EvaGreen SuperMix, 1 µL of each primer (10 µmol/L), 3 µL of BSA solution (20 mg/mL), 1.5 µL of SuperScript® III Reverse Transcriptase, 17.5 µL of nuclease-free water, and 6 µL of template solution.

Primer sequences for HIV viral RNA was selected from a previous publication:[4] GRA ACC CAC TGC TTA ASS CTC AA (SEQ OD NO: 3); GAG GGA TCT CTA GNY ACC AGA GT (SEQ ID NO: 4). Primer sequences for control HCV viral RNA were selected from a previous publication:[5] GAG TAG TGT TGG GTC GCG AA (SEQ ID NO: 5); GTG CAC GGT CTA CGA GAC CTC (SEQ ID NO: 6).

RT-PCR Amplification on the Devices

To amplify HIV viral RNA in FIG. 5, the RT-PCR mix contained the following: 15 µL of 2× EvaGreen SuperMix, 0.6 µL of each primer (10 µmol/L), 1.5 µL of BSA solution (20 mg/mL), 0.75 µL of SuperScript® III Reverse Transcriptase, 10.05 µL of nuclease-free water, and 1.5 µL of template solution. The template solution used here was diluted 250-fold from the original HIV viral RNA stock solution purified from Patient sample 2 using 1 mg/mL BSA solution.

To amplify control HCV viral RNA in FIG. 5, the RT-PCR mix contained the following: 15 µL of 2× EvaGreen SuperMix, 0.25 µL of each primer (10 µmol/L), 1.5 µL of BSA solution (20 mg/mL), 0.75 µL of SuperScript® III Reverse Transcriptase, 10.25 µL of nuclease-free water, and 2 µL of template solution. The template solution was diluted 5-fold from the original control HCV viral RNA stock solution purified from OptiQuant-S HCV Quantification Panel.

To amplify the control RNA (906 nt) in FIG. 5, the RT-PCR mix contained the following: 15 µL of 2× EvaGreen SuperMix, 0.25 µL of each primer (10 µmol/L), 1.5 µL of BSA solution (20 mg/mL), 0.75 µL of SuperScript® III Reverse Transcriptase, 10.25 µL of nuclease-free water, and 2 µL of template solution. The template solution was diluted 5-fold from the original control HCV viral RNA stock solution purified from OptiQuant-S HCV Quantification Panel.

The experiment in FIG. 5 was repeated six times, and the resultant data were used to calculate the target concentration.

To amplify HIV viral RNA with expected final concentration above 1000 molecules/mL in the RT-PCR mix in FIG. 6, the RT-PCR mix contained the following: 20 µL of 2× EvaGreen SuperMix, 1 µL of each primer (10 µmol/L), 2 µL of BSA solution (20 mg/mL), 1 µL of SuperScript® III Reverse Transcriptase, 13 µL of nuclease-free water, and 2 µL of template solution. The template was serially diluted in 1 mg/mL BSA solution. For experiments with HIV viral RNA concentration below 1000 molecules/mL in the final RT-PCR mix, the RT-PCR mix contained the following: 30 µL of 2× EvaGreen SuperMix, 1.5 µL of each primer (10 µmol/L), 2 µL of BSA solution (20 mg/mL), 1.5 µL of SuperScript® III Reverse Transcriptase, 3.5 µL of nuclease-free water, and 20 µL of template solution.

To amplify the control RNA (906 nt) in the HIV sample in FIG. 5 and FIG. 6, the RT-PCR mix contained the following: 20 µL of 2× EvaGreen SuperMix, 1 µL of each primer (10 µmol/L), 2 µL of BSA solution (20 mg/mL), 1 µL of SuperScript® III Reverse Transcriptase, 13 µL of nuclease-free water, and 2 µL of HIV viral RNA stock solution after sample preparation.

The concentration of control RNA (906 nt) before sample preparation was characterized on device Design 1 (FIG. 11) with the RT-PCR mix contained the following: 20 µL of 2× EvaGreen SuperMix, 1 µL of each primer (10 µmol/L), 2 µL of BSA solution (20 mg/mL), 1 µL of SuperScript® III Reverse Transcriptase, 13 µL of nuclease-free water, and 2 µL of template solution. The template was prepared by diluting 2 µL of stock control RNA (906 nt) solution into 400 µL of 1 mg/mL BSA solution.

To amplify HIV viral RNA in FIG. 7, the RT-PCR mix for HIV viral RNA contained the following: 90 µL of 2× EvaGreen SuperMix, 3.6 µL of each primer (10 µmol/L), 6 µL of BSA solution (20 mg/mL), 4.5 µL of SuperScript® III Reverse Transcriptase, 12.3 µL of nuclease-free water, and 60 µL of template solution. The template solution used here was diluted 62500-fold from the original HIV viral RNA stock solution purified from Patient sample 2 using 1 mg/mL BSA solution. This experiment was repeated six times and all data was used to calculate HIV viral RNA concentration. Three negative control experiments were performed with the same primer pairs but no HIV viral RNA, and showed no false positives.

The amplifications were performed using a PCR master-cycler machine (Eppendorf). To amplify the RNA, an initial 30 min at 50° C. was applied for reverse transcription, then 2 min at 95° C. for enzyme activation, followed by 35 cycles of 1 min at 95° C., 30 sec at 55° C. and 45 sec at 72° C. After the final cycle, a final elongation step was applied for 5 min at 72° C. This thermal cycling program was applied to all experiments except for those in FIG. 7, where 39 cycles were adapted instead of 35 cycles.

Image Acquisition and Analysis

Bright-field images in FIG. 1 and FIG. 5 were acquired using a Canon EOS Rebel XS digital SLR camera (Lake Success, N.Y.). Other bright-field images were acquired using a Leica stereoscope. All fluorescence images were acquired by Leica DMI 6000 B epi-fluorescence microscope with a 5×/0.15 NA objective and L5 filter at room temperature. All fluorescence images were corrected for background by using an image acquired with a standard fluorescent control slide. All the images were then stitched together using MetaMorph software (Molecular Devices, Sunnyvale, Calif.).

FIG. 7 shows a representative experiment performing RT-PCR of HIV viral RNA at an expected concentration of 51 molecules/mL in RT-PCR mix on the Design 2B device to test the lower detection limit of the device. This experiment was repeated six times to quantify the viral RNA concentration.

Figure 8:
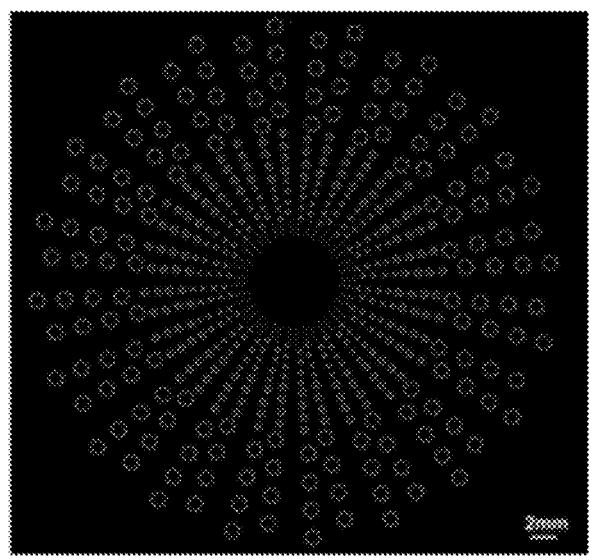
FIG. 8 illustrates a representative negative control for HIV viral load.

FIG. 8 shows a representative negative control for HIV viral load (HIV primers with no loaded HIV RNA template) on device Design 1, corresponding to experiments shown in FIG. 6.

FIG. 9 (table) presents performance of quantification of HIV viral RNA concentration from patient 1 on device comparing to Roche COBAS® AmpliPrep/COBAS® TaqMan® HIV-1 Test, v2.0 system (CAP/CTM v2.0). Each experiment was repeated at least four times on device. Only 2 significant digits are shown. The expected HIV concentration of patient plasma was calculated based on dilution factors and a single result from Roche CAP/CTM v2.0. The results from device are obtained with serial diluted purified patient HIV viral RNA and are converted to the original concentration in patient plasma (with or without dilutions) using the purification concentrating factor.

FIG. 10 (table) shows performance of quantification of HIV viral RNA concentration from patient 2 on device comparing to Roche COBAS® AmpliPrep/COBAS® TaqMan® HIV-1 Test, v2.0 system (CAP/CTM v2.0). Each experiment was repeated at least four times on device. Only 2 significant digits are shown. The expected HIV concentration of patient plasma was calculated based on dilution factors and a single result from Roche CAP/CTM v2.0. The results from device are obtained with serial diluted purified patient HIV viral RNA and are converted to the original concentration in patient plasma (with or without dilutions) using the purification concentrating factor.

LAMP Amplification

Digital reverse transcription loop mediated isothermal amplification (RT-LAMP) can be performed on a device according to the present disclosure. In some embodiments, digital RT-LAMP is performed on a multivolume device. In one embodiment, one-step digital RT-LAMP is carried out by mixing template, primers, detection reagent, reaction mix and enzyme, then loading the solution onto a device and heating up the device to a proper temperature for a period of time.

For example, the following mixture of reagents has been used: 20 μL reaction mix, 2 μL enzyme mix (Loopamp RNA Amplification Kit from Eiken Chemical Co,. LTD.), 2 μL detection reagent (Eiken Chemical Co,. LTD.), 2 μL 20 mg/mL BSA, 8 μL RNase free water, 4 uL primer mix and 2 μL HIV RNA purified from AcroMetrix® HIV-1 Panel 1E6. The final concentration of primers was 2 μM for BIP/FIP, 1 μM for LOOP primers, 0.25 μM for B3/F3. All solutions were operated on ice.

The solution was loaded onto a multivolume device (design published in Shen et al., JACS 2011 133: 17705) and the relative position of the plates of the device were fixed by wax. The whole device was heated on a thermal cycler block (Eppendorf) for about 1 hour then terminated at 95° C. for 2 minutes. The fluorescence image was acquired by Leica DMI 6000 B epi-fluorescence microscope with a 5×/0.15 NA objective and L5 filter at room temperature. The measured concentration of digital RT-LAMP was 10% of that from digital RT-PCR using B3/F3 as primers.

In another embodiment, two-step digital RT-LAMP is carried out in two separate steps. Reverse Transcription is done by mixing template, BIP/FIP primers, reverse transcriptase, and reaction mix in a tube, and heating to a proper temperature. Digital LAMP is performed by mixing cDNA solution with all other components, loading the solution onto a device, and heating the device at a proper temperature for a period of time.

In another embodiment, digital RT-LAMP is performed by running the reverse transcription step on the device in a digital format, mixing the product with other components of LAMP on-chip and heating the device. The result of this protocol has been experimentally observed to be the same as when performing the RT step in a test tube.

In one set of experiments performed with two-step digital RT-LAMP, 10 μL reaction mix, 1 μL 20 mg/mL BSA, 0.5 μL Superscript III reverse transcriptase (Invitrogen), 6 μL RNase free water, 0.5 uL BIP/FIP primer mix (10 μM) and 2 μL HIV RNA purified from AcroMetrix® HIV-1 Panel 1E6 were mixed together in a test tube. All solutions were operated on ice. The solution was heated to 50° C. for 15 min for reverse transcription.

All other components of LAMP mixture (2 μL enzyme mix, 2 μL detection reagent, 10 μL reaction mix, 1 μL 20 mg/mL BSA, all other primers and RNase free water to make up the volume to 20 μL.) were mixed together with the solution obtained from reverse transcription and loaded on a device immediately. The whole device was heated on a thermal cycler block (Eppendorf) for about 1 hour then terminated at 95° C. for 2 minutes. Imaging settings were the same as described for the one-step RT-LAMP experimental protocol above. The measured concentration obtained after performing digital RT-LAMP was found to be 30% of that from digital RT-PCR using B3/F3 as primers.

In another set of experiments, the efficiency of two-step digital RT-LAMP was found to be improved by adding only BIP/FIP primer in the RT step, adding RNase H after the RT step and removing B3 from the primer mixture.

For example, 10 μL reaction mix, 1 μL 20 mg/mL BSA, 0.5 μL Superscript III reverse transcriptase (Invitrogen), 6 μL RNase free water, 0.5 uL BIP/FIP primer mix (10 μM) and 2 μL HIV RNA purified from AcroMetrix® HIV-1 Panel 1E6 were mixed together. All solutions were operated on ice. The solution was heated to 50° C. for 15 min for reverse transcription then followed by the addition of 0.5 μL RNase H (NEB) and incubation at 37° C. for 10 minutes.

All other components of LAMP mixture (2 μL enzyme mix, 2 μL detection reagent, 10 μL reaction mix, 1 μL 20 mg/mL BSA, all other primers except for B3 and RNase free water to make up the volume to 20 μL) were mixed together with the solution obtained from reverse transcription and loaded on a device immediately. Heating and imaging settings were the same as described for the two-step RT-LAMP experimental protocol above. The measured concentration after performing digital RT-LAMP was found to be 60% of that obtained via digital RT-PCR using B3/F3 as primers.

In another set of experiments, the efficiency of two-step digital RT-LAMP was found to be improved by adding only BIP/FIP primer in the RT step, adding thermostable RNase H into the LAMP mixture and removing B3 from the primer mixture.

For example, 10 μL reaction mix, 1 μL 20 mg/mL BSA, 0.5 μL Superscript III reverse transcriptase (Invitrogen), 6 μL RNase free water, 0.5 uL BIP/FIP primer mix (10 μM) and 2 μL HIV RNA purified from AcroMetrix® HIV-1 Panel 1E6 were mixed together. All solutions were operated on ice. The solution was heated to 50° C. for 15 min for reverse transcription.

All other components of LAMP mixture (2 μL enzyme mix, 2 μL detection reagent, 10 μL reaction mix, 1 μL 20 mg/mL BSA, all other primers except for B3 and RNase free water to make up the volume to 20 μL) and 0.5 uL Hybridase™ Thermostable RNase H (Epicenter) were mixed together with the solution obtained from reverse transcription and loaded on a device immediately. The heating and imaging settings were the same as described for the two-step RT-LAMP experimental protocols above. The measured concentration after performing digital RT-LAMP was found to be 60% of that obtained from digital RT-PCR using B3/F3 as primers.

Imaging with Mobile Device Camera

In one embodiment, an imaging device with wireless communication capability may be used to capture the results of both isothermal and non-isothermal methods such as digital LAMP and digital NASBA performed on a microfluidic device as disclosed herein.

As one example, an iPhone 4S™ is used to capture results on a disclosed device. The fluorescence readout is achieved by a standard iPhone 4S™ 8 MP camera equipped with a yellow dichroic long-pass filter 10CGA-530 (Newport, Franklin, Mass.). Fluorescence excitation was achieved by shining blue light on a device at an oblique angle of approximately 30°. The light source was a blue LED (LIU003) equipped with a blue short-pass dichroic filter FD1B (Thorlabs, Newton, N.J.). Excitation light reached the sample in two ways: by direct illumination and by multiple reflections between the device plates.

A device of a design described in a previous publication (Shen et al., JACS 2011 133: 17705) was imaged in the experiments. Soda-lime glass plates with chromium and photoresist coating (Telic Company, Valencia, Calif.) were used to fabricate devices. The method for making a glass device described in a previous publication (Du, *Lab Chip* 2009, 2286-2292), was used. Briefly, the photoresist-coated glass plate was exposed to ultraviolet light covered by a photomask with designs of the wells and ducts. Following removal of the photoresist using 0.1 M NaOH solution, the exposed chromium coating was removed by a chromium-etching solution. The patterns were then etched in glass etching solution in a 40° C. shaker. After glass etching, the remaining photoresist and chromium coatings were removed by ethanol and chromium-etching solution, respectively. The surfaces of the etched glass plates were cleaned and subjected to an oxygen plasma treatment, and then the surfaces were rendered hydrophobic by silanization in a vacuum desiccator as previously described (Roach, *Analytical Chemistry* 2005, 785-796). Inlet holes were drilled with a diamond drill bit 0.035 inch in diameter.

A fluorescent reaction mix for digital LAMP was prepared, loaded in the device, and allowed to react, as described elsewhere in this application.

An image was produced using an iPhone application, Camera+™ (obtained via taptaptap.com) in automatic mode; no tripod was used. The excitation light was shined from one side of the device under an oblique angle of approximately 30°. The resulting illumination was relatively uniform, suggesting that light spreads by multiple reflections inside the analysis device.

FIG. 12 shows an image of a multivolume device filled with LAMP reaction mix obtained with a iPhone 4S™ camera. Image size is 8 MP. The total number of wells of each kind is 160. In total there are 122 positive largest wells, 42 of the second largest positive wells, 5 of the second smallest positive wells and 2 of the smallest positive wells. Well count was done automatically using Metamorph software. The signal/noise ratio is over 20 even for the smallest wells.

FIG. 13 shows a magnified portion of the image in FIG. 12. In this image, the smallest wells in the image are approximately 15-20 pixels wide and the signal/noise ratio is over 20.

Additional information may be found in the following references, each of which is incorporated by reference in its entirety.

(1) Marcus, J. S.; Anderson, W. F.; Quake, S. R. Anal. Chem. 2006, 78, 3084-3089.

(2) Stahlberg, A.; Bengtsson, M. Methods 2010, 50, 282-288.

(3) Grond-Ginsbach, C.; Hummel, M.; Wiest, T.; Horstmann, S.; Pfleger, K.; Hergenhahn, M.; Hollstein, M.; Mansmann, U.; Grau, A. J.; Wagner, S. J. Neurol. 2008, 255, 723-731.

(4) Kern, W.; Schoch, C.; Haferlach, T.; Schnittger, S. Crit. Rev. Oncol./Hematol. 2005, 56, 283-309.

(5) Schmidt, U.; Fuessel, S.; Koch, R.; Baretton, G. B.; Lohse, A.; Tomasetti, S.; Unversucht, S.; Froehner, M.; Wirth, M. P.; Meye, A. Prostate 2006, 66, 1521-1534.

(6) Anglicheau, D.; Suthanthiran, M. Transplantation 2008, 86, 192-199.

(7) Whitney, J. B.; Luedemann, C.; Bao, S.; Miura, A.; Rao, S. S.; Mascola, J. R.; Letvin, N. L. Aids 2009, 23, 1453-1460.

(8) Gurunathan, S.; El Habib, R.; Baglyos, L.; Meric, C.; Plotkin, S.; Dodet, B.; Corey, L.; Tartaglia, J. Vaccine 2009, 27, 1997-2015.

(9) UNAIDS/WHO. 2008 Report on the Global AIDS Epidemic, 2008.

(10) Calmy, A.; Ford, N.; Hirschel, B.; Reynolds, S. J.; Lynen, L.; Goemaere, E.; de la Vega, F. G.; Perrin, L.; Rodriguez, W. Clin. Infect. Dis. 2007, 44, 128-134.

(11) Shepard, C. W.; Finelli, L.; Alter, M. Lancet Infect. Dis. 2005, 5, 558-567.

(12) US Food and Drug Administration. FDA approves Incivek for hepatitis C, 2011 http://www.fda.gov/NewsEvents/Newsroom/Press-Announcements/ucm256299.htm.

(13) US Food and Drug Administration. FDA approves Victrelis for Hepatitis C, 2011 http://www.fda.gov/NewsEvents/Newsroom/Press-Announcements/ucm255390.htm.

(14) Ferguson, M. C. Pharmacotherapy 2011, 31, 92-111.

(15) Poordad, F.; et al. New Engl. J. Med. 2011, 364, 1195-1206.

(16) Bustin, S. A. Biomark. Med. 2008, 2, 201-207.

(17) Murphy, J.; Bustin, S. A. Expert Rev. Mol. Diagn. 2009, 9, 187-197.

(18) Lee, H. H.; Dineva, M. A.; Chua, Y. L.; Ritchie, A. V.; Ushiro-Lumb, I.; Wisniewski, C. A. J. Infect. Dis. 2010, 201, S65-S72.

(19) Department of Human Health and Human Services. Panel on Antiretroviral Guidelines for Adults and Adolescents. Guidelines for the use of antiretroviral agents in HIV-1-infected adults and adolescents, Jan. 10, 2011 http://www.aidsinfo.nih.gov/contentfiles/adultandadolescentgl.pdf.

(20) World Health Organization. Clinical and Laboratory Monitoring of Antiretroviral Therapy in Resource-Limited and Unlimited Settings, 2000 http://www.phclab.com/images/WHO%20Aids%20N1.pdf.

(21) Sykes, P. J.; Neoh, S. H.; Brisco, M. J.; Hughes, E.; Condon, J.; Morley, A. A. Biotechniques 1992, 13, 444-449.

(22) Vogelstein, B.; Kinzler, K. W. Proc. Natl. Acad. Sci. U.S.A. 1999, 96, 9236-9241.

(23) Ottesen, E. A.; Hong, J. W.; Quake, S. R.; Leadbetter, J. R. Science 2006, 314, 1464-1467.

(24) Fan, H. C.; Quake, S. R. Anal. Chem. 2007, 79, 7576-7579.

(25) Beer, N. R.; Hindson, B. J.; Wheeler, E. K.; Hall, S. B.; Rose, K. A.; Kennedy, I. M.; Colston, B. W. Anal. Chem. 2007, 79, 8471-8475.

(26) Leng, X. F.; Zhang, W. H.; Wang, C. M.; Cui, L. A.; Yang, C. J. Lab Chip 2010, 10, 2841-2843.

(27) Pekin, D.; Skhiri, Y.; Baret, J.; Cone, D. L.; Mazutis, L.; Salem, C. B.; Millot, F.; Harrak, A. E.; Hutchison, J. B.; Larson, J. W.; Link, D. R.; Laurent-Puig, P.; Griffiths, A. D.; Taly, V. Lab Chip 2011, 2156-2166.

(28) Sundberg, S. O.; Wittwer, C. T.; Gao, C.; Gale, B. K. Anal. Chem. 2010, 82, 1546-1550.

(29) Applied Biosystems, Life Technologies. TaqManÒ OpenArrayÒ Digital PCR Plates, 2010 https://products.appliedbiosystems.com/ab/en/US/adirect/ab?cmd=catNavigate2&catID=607965.

(30) Du, W. B.; Li, L.; Nichols, K. P.; Ismagilov, R. F. Lab Chip 2009, 9, 2286-2292.

(31) Shen, F.; Du, W. B.; Davydova, E. K.; Karymov, M. A.; Pandey, J.; Ismagilov, R. F. Anal. Chem. 2010, 82, 4606-4612.

(32) Shen, F.; Du, W. B.; Kreutz, J. E.; Fok, A.; Ismagilov, R. F. Lab Chip 2010, 10, 2666-2672.

(33) Shen, F.; Davydova, E. K.; Du, W. B.; Kreutz, J. E.; Piepenburg, O.; Ismagilov, R. F. Anal. Chem. 2011, 83, 3533-3540.

(34) Kreutz, J. E.; Munson, T.; Huynh, T.; Shen, F.; Du, W.; Ismagilov, R. F. Anal. Chem. 2011, DOI: 10.1021/ac201658s.

(35) Li, L. A.; Karymov, M. A.; Nichols, K. P.; Ismagilov, R. F. Langmuir 2010, 26, 12465-12471.

(36) Du, W. B.; Li, L.; Nichols, K. P.; Ismagilov, R. F. Lab Chip 2009, 9, 2286-2292.

(37) Shen, F.; Davydova, E. K.; Du, W. B.; Kreutz, J. E.; Piepenburg, O.; Ismagilov, R. F. Anal. Chem. 2011, 83, 3533-3540.

(38) Li, L. A.; Karymov, M. A.; Nichols, K. P.; Ismagilov, R. F. Langmuir 2010, 26, 12465-12471.

(39) McBreen, S.; Imlach, S.; Shirafuji, T.; Scott, G. R.; Leen, C.; Bell, J. E.; Simmonds, P. J. Virol. 2001, 75, 4091-4102.

(40) Meng, S. A.; Li, J. M. Virol. J. 2010, 7, Article No: 117.

---

What is claimed:

1. A device, comprising:
a first component and a second component;
a first population of areas disposed in said first component and said second component;
a second population of areas disposed in said first component and said second component; and
an inlet,
wherein the first component and the second component are engageable with one another such that a plurality of the first population of areas disposed in said first component and a plurality of the first population of areas disposed in said second component are in fluidic communication with the inlet via a continuous fluidic path within said first and second components, wherein relative motion between the first component and the second component isolates the plurality of the first population of areas disposed in said first component from the plurality of the first population of areas disposed in said second component and exposes at least some of the first population of areas to at least some of the second population of areas so as to form a plurality of analysis regions, at least some of the analysis regions differing in volume from others of the analysis regions, and wherein the first component and the second component are engaged with each other before and after the relative motion.

2. The device of claim 1, wherein the first and second components are engaged so as to permit rotational motion of one component relative to the other component.

3. The device of claim 1, wherein the first and second components are engaged so as to permit linear movement of one component relative to the other component.

4. The device of claim 1, wherein at least one of the first or second components has a thickness in the range of from about 10 micrometers to about 5000 micrometers.

5. The device of claim 1, wherein at least one first area defines a well having a volume in the range of from about 0.1 picoliter to about 10 microliters.

6. The device of claim 1, wherein at least one second area defines a well having a volume in the range of from about 0.1 picoliter to about 10 microliters.

7. The device of claim 1, wherein at least one analysis region defines a volume in the range of from about 0.1 picoliter to about 20 microliters.

8. The device of claim 1, wherein the ratio of the volumes defined by two analysis regions is in the range of from about 1:1 to about 1:1,000,000.

9. The device of claim 1, further comprising an imager configured to capture at least one image of an analysis region.

10. The device of claim 1, wherein the device is configured to display an image of an analysis region for capture of at least one image by an imager.

11. The device of claim 10, wherein the imager is a mobile phone camera.

12. The device of claim 9, further comprising a processor configured to estimate a concentration of an analyte residing in one or more analysis regions.

13. The device of claim 1, wherein at least one first area defines a volume that differs from the volume defined by at least one second area.

14. The device of claim 1, wherein the device is adapted so as to be capable of placing at least about 10 first areas into pairwise exposure with at least 10 second areas.

15. The device of claim 14, wherein the device is adapted so as to be capable of placing at least about 100 first areas into pairwise exposure with at least 100 second areas.

16. The device of claim 15, wherein the device is adapted so as to be capable of placing at least about 200 first areas into pairwise exposure with at least 200 second areas.

17. The device of claim 1, further comprising a quantity of a reagent disposed within the device.

18. The device of claim 17, wherein the reagent is useful in an amplification reaction.

19. A device, comprising:
a first component and a second component
a first population of wells disposed in a surface of the first component and in a surface of the second component, the first population of wells arranged in each surface in a radial pattern;
a second population of wells disposed in said surface of the first component and in the surface of the second component, the second population of wells arranged in each surface in a radial pattern; and
an inlet,
the first component and the second components being engageable with one another such that a plurality of the first population of wells disposed in said first component and a plurality of the first population of wells disposed in said second component are in fluidic communication with the inlet via a continuous fluidic path within said first and second components, wherein relative rotational motion between the first component and the second component isolates the plurality of the first population of wells disposed in said first component from the plurality of the first population of wells disposed in said second component and exposes at least some of the first population of wells to at least some of the second population of wells so as to form a plurality of analysis regions, an analysis region comprising a first well and a second well being in pairwise exposure with one another, and wherein the first component and the second component are engaged with each other before and after the relative rotational motion.

20. The device of claim 19, wherein at least two analysis regions have volumes that differ from one another.

21. The device of claim 19, wherein the first component comprises a channel having the inlet, the channel configured so as to place at least some of the first wells into fluidic communication with the environment exterior to the channel.

22. The device of claim 21, wherein the inlet resides in a surface of the first component other than the surface of the first component in which the first wells are formed.

23. The device of claim 19, wherein the device comprises from about 10 to about 10,000 first wells.

24. The device of claim 19, wherein the device comprises from about 10 to about 10,000 second wells.

* * * * *

UNITED STATES PATENT AND TRADEMARK OFFICE
CERTIFICATE OF CORRECTION

PATENT NO. : 9,464,319 B2
APPLICATION NO. : 13/467482
DATED : October 11, 2016
INVENTOR(S) : Rustem F. Ismagilov et al.

Page 1 of 1

It is certified that error appears in the above-identified patent and that said Letters Patent is hereby corrected as shown below:

On Column 1, after the heading STATEMENT OF GOVERNMENT RIGHTS, replace the paragraph on Lines 42-47 with the following paragraph:
-- This invention was made with government support under grant number OD 003584 awarded by the National Institutes of Health, and grant number GM074961 awarded by the National Institutes of Health, and grant number CHE 0526693 awarded by the National Science Foundation, and grant number R01 EB012946 awarded by the National Institutes of Health. The government has certain rights in the invention. --

Signed and Sealed this
Twenty-fifth Day of September, 2018

Andrei Iancu
*Director of the United States Patent and Trademark Office*

SEQUENCE LISTING

```
<160> NUMBER OF SEQ ID NOS: 6

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaagagttgg cgaaagatcc acg                                              23

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cgagctcgaa ttagtctgcg c                                                21

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
graacccact gcttaassct caa                                              23
```

```
<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(14)
<223> OTHER INFORMATION: a, c, t, g, unknown or other

<400> SEQUENCE: 4
gagggatctc tagnyaccag agt                                           23

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gagtagtgtt gggtcgcgaa                                               20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtgcacggtc tacgagacct c                                             21
```